US009505828B2

(12) United States Patent
Mechali et al.

(10) Patent No.: US 9,505,828 B2
(45) Date of Patent: Nov. 29, 2016

(54) USE OF A NEW GENE CODING FOR A NEW MEMBER OF THE MCM2-8 FAMILY IN PHARMACEUTICAL COMPOSITIONS

(71) Applicant: CENTRE NATIONAL DE LA RECHERCHE SCIENTIFIQUE, Paris 16 (FR)

(72) Inventors: Marcel Mechali, Montferrier sur Lez (FR); Domenico Maiorano, Saint-Martin de Londres (FR); Malik Lutzmann, Montpellier (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 13/927,944

(22) Filed: Jun. 26, 2013

(65) Prior Publication Data

US 2013/0289237 A1 Oct. 31, 2013

Related U.S. Application Data

(62) Division of application No. 11/914,374, filed as application No. PCT/EP2006/004509 on May 12, 2006, now Pat. No. 8,497,101.

(60) Provisional application No. 60/680,480, filed on May 13, 2005.

(51) Int. Cl.
*C07K 16/40* (2006.01)
*C07K 16/18* (2006.01)
*C07K 14/47* (2006.01)

(52) U.S. Cl.
CPC .......... *C07K 16/18* (2013.01); *C07K 14/4738* (2013.01); *C07K 16/40* (2013.01)

(58) Field of Classification Search
None
See application file for complete search history.

(56) References Cited

U.S. PATENT DOCUMENTS

2013/0303395 A1* 11/2013 Lueking et al. .................. 506/9

FOREIGN PATENT DOCUMENTS

WO WO 01/55312 A2 * 8/2001
WO WO 03/038052 A2 * 5/2003

OTHER PUBLICATIONS

Sequence search, result 2, Jan. 23, 2015 (provided in body of enclosed Office Action).*

Klein et al., Genetic and genomic tools for Xenopus research: The NIH Xenopus initiative., Developmental Dynamics., 2002, vol. 225, pp. 384-391.

The MGC Project Team, The status, quality, and expansion of the NIH full-length cDNA project: the Mammalian Gene Collection (MGC)., Genome Res., Oct. 14, 2004 vol. 10B, pp. 2121-2127.

Mungall et al., The DNA sequence and analysis of human chromosome 6., Nature, 2003, vol. 425, pp. 805-811.

Guo et al., Protein tolerance to random amino acid change, 2004, Proc. Natl. Acad. Sci. USA 101: 9205-9210.

Lazar et al., Transforming Growth Factor a: Mutation of Aspartic Acid 47 and Leucine 48 Results in Different Biological Activity, 1988, Mol. Cell. Biol. 8:1247-1252.

Hill et al., Functional Analysis of conserved Histidines in ADP-Glucose Pyrophosphorylase from *Escherichia coli*, 1998, Biochem. Biophys. Res. Comm. 244:573-577.

Wacey et al., Disentangling the perturbational effects of amino acid substitutions in the DNA-binding domain of p53., Hum Genet, 1999, vol. 104, pp. 15-22.

Yoshida, K., "Identification of a novel cell-cycle-induced MCM family protein MCM9", Biochemical and Biophysical Research Communication, Academic Press Inc. Orlando, FL, US, vol. 331, No. 2, Apr. 9, 2005, pp. 669-674.

Lutzmann et al "Indentification on full genes and proteins of MCM9, a novel vertebrate-specific member of the MCM2-8 protein family" Gene: An International Journal of Genes and Genomes, Elsevier, Amsterdam, NL, vol. 362, Dec. 5, 2005, pp. 51-56, XP005162054 ISSN: 0378-119.

Maiorano D. et al., "MCM8 is an MCM2-7-related protein that functions as a DNA helicase during replication elongation and not initiation" Cell, Cell Press, Cambridge, NA, US, vol. 120, No. 3, Feb. 10, 2005, pp. 315-328, XP002375862, ISSN: 0092-8674.

Freeman, A et al., "Minichromosome maintenance proteins as biological markers of dysplasia and malignancy", Clinical Cancer Research: An Official Journal of the American Association for the Cancer Research, Aug. 1999, vol. 5, No. 8, pp. 2121-2132, XP002399767, ISSN: 1078-0432.

Forsburg S. L "Eukaryotic MCM proteins: Beyond replication initiation" Microbiology and Molecular Biology Reviews, American Society for Microbiology, US, vol. 68, No. 1, Mar. 2004, pg. 109-131, X002393215, ISSN: 1092-2172.

* cited by examiner

*Primary Examiner* — Ron Schwadron
(74) *Attorney, Agent, or Firm* — Young & Thompson

(57) ABSTRACT

An isolated antibody specifically binding the C-terminus part of the MCM9 protein, the C-terminus part of the MCM9 protein is one of the following sequences: the amino acids sequence from the position 391 to the position 1143 of the MCM9 proteins of the sequence as set forth in SEQ ID NO: 2 or 16, or the amino acids sequence from the position 391 to the position 1143 of the MCM9 protein of the sequence as set forth in SEQ ID NO: 8.

1 Claim, 11 Drawing Sheets

```
Human    ------------------------------------------------------------
Mouse    MDQRTTRNGKYCDVEPVSRSNPAPCLRDPPLRRLVRPKPRLQLPESRLSPCSRLPLADSS 60
Chicken  ------------------------------------------------------------
Xenopus  ------------------------------------------------------------

Human    ------------------------------------------------------------
Mouse    VRPGARPPASAPGRSPSGRKVEAVRGSGSAGSSSPSEAEREQREEACAPPRKAAPSSGRA 120
Chicken  ------------------------------------------------------------
Xenopus  ------------------------------------------------------------

Human    ------------------------------------MNSDQVTLVGQVFESYVSEYHKND 24
Mouse    HAPPPPTPRGSGWGDHGRSAVPATKTVRVEPYPPFKMNSEQVTLVGQVFESYVSEYHKND 180
Chicken  ----------------------------------MALRADQVSLIGQVFESYLLQHHRDD 26
Xenopus  ----------------------------------MYLGFEQVALVGQVFESFVLEHHKNE 26
                                            :  :**:*:******:: ::*:::

Human    ILLILKERDEDAHYPVVVNAMTLFETNMEIGEYFNMFPSEVLTIFDSALRRSALTILQSL 84
Mouse    ILLILKERDEDAHYPVVVNAMSLFETNMEIGDYFTVFPNEVLTVFDSALRRSALAILQSL 240
Chicken  ILGILRQGDDEAHYPVLVDALTLFETNMEIGEYFNAFPSQVLPIFDGALRRAAMAVLQAA 86
Xenopus  IAQILTEKEEHAHYSLVVNAMTLFEANMEIGEYFNAFPNEVLPVFDNALRCAAMSFLQSC 86
         *  ** : ::.***.::*:*::***:*****:**. **.:**.:**.*** :*::.**:

Human    SQPEAVSMKQNLHARISGLPVCPELVREHIPKTKDVGHFLSVTGTVIRTSLVKVLEFERD 144
Mouse    PETEGLSMKQNLHARISGLPVCPELVREHIPKTKDVGHFLSVTGTVIRTSLVKVLEFERD 300
Chicken  TPSPELRMKPNLHARISGLPICPELTREHIPKTRDVGHFLSVTGTVIRTSLVKVLEFERS 146
Xenopus  SEKYTFLMKQNLHARITGLPVCPELTREHIPRTRDVGHFLSVTGTVIRTSLVKVLEYEQD 146
         .    . ** ******:***:****.****:*:**********************:*:.

Human    YMCNKCKHVFVIKADFEQYYTFCRPSSCPSLESCDSSKFTCLSGLSSSPTRCRDYQEIKI 204
Mouse    YMCNKCKHVFMVEADFEQYYTFSRPSSCPSLASCDSSKFSCLSDLSSSPARCRDYQEIKI 360
Chicken  YICNKCKHVFVAKADFEQYYAFCRPSACLNEEGCNSTKFTCLSGTSSSPSSCRDYQEIKI 206
Xenopus  FMCNKCKHVVTVKADFEQHYTFKPPIACSNEEGCNSTKFTCLSD-SSSPASCRDYQEIKI 205
         ::*******.  :*****:*:*  * :*  .   .*:*:**:***. ****: ********

Human    QEQVQRLSVGSIPRSMKVILEDDLVDSCKSGDDLTIYGIVMQRWKPFQQDVRCEVEIVLK 264
Mouse    QEQVQRLSVGSIPRSMKVILEDDLVDSCKSGDDLTIYGVVMQRWKPFQRDVRCEVEIVLK 420
Chicken  QEQVQRLSVGSIPRCMVVVLEDDLVDSCKSGDDITVYGVVMQRWKPFHQDARCDLELVLK 266
Xenopus  QEQVQRLSVGSIPRSMIVVLEDDLVDSCKSGDDITVYGVVMQRWKPLYIDMRCDLEIVLK 265
         **************.* *:***************:*:**:*******:  * **::*:***

Human    ANYIQVNNEQSSGIIMDEEVQKEFEDFWEYYKSDPFAGRNVILASLCPQVFGMYLVKLAV 324
Mouse    ANYVQVNNEQSSGMVMDEDTRKEFEDFWEHYKSDPFAGRNEILASLCPQVFGMYLVKLAV 480
Chicken  ANYVKVNNEQLAGVTIDEEVRKEFEDFWEKHRNNPLAGRNEILASLCPQVFGLYLVKLAV 326
Xenopus  ANYISVNNEQPCGVVINEEVRKEYEDFWVKYRNNPLEGRNEILASLCPQVFGMFVVKLAV 325
         ***:.***** .*: ::*:.:**:****  :.:*: *** ***********:::*****

Human    AMVLAGGIQRTDATGTRVRGESHLLLVGDPGTGKSQFLKYAAKITPRSVLTTGIGSTSAG 384
Mouse    AMVLAGGIQRTDAAGTRVRGESHLLLVGDPGTGKSQFLKYAAKITPRSVLTTGIGSTSAG 540
Chicken  AMVLAGGVQRIDATGTRIRGESHLLLVGDPGTGKSQFLKYAVKITPRSVLTAGIGSTSAG 386
Xenopus  AMVLAGGVQRIDSAGTRVRGESHLLLVGDPGTGKSQFLKYAAKITPRSVLTAGIGSTSAG 385
         *******:** *::***:*************************.*********:********

Human    LTVTAVKDSGEWNLEAGALVLADAGLCCIDEFNSLKEHDRTSIHEAMEQQTISVAKAGLV 444
Mouse    LTVTAVKDSGEWNLEAGALVLADAGLCCIDEFNSLKEHDRTSIHEAMEQQTISVAKAGLV 600
Chicken  LTVTAVKDFGEWNLEAGALVLADGGLCCIDEFNSIKEHDRTSIHEAMEQQTISVAKAGLV 446
Xenopus  LTVTAVKDSGEWNLEAGALVLADGGLCCIDEFNSIKEHDRTSIHEAMEQQTISVAKAGLV 445
         ******** ***************.**********:*************************

Human    CKLNTRTTILAATNPKGQYDPQESVSVNIALGSPLLSRFDLILVLLDTKNEDWDRIISSF 504
Mouse    CKLNTRTTILAATNPKGQYDPKESVSVNIALGSPLLSRFDLVLVLLDTRNEDWDRIISSF 660
Chicken  CKLNTRTTILAATNPKGHYDPAESVSVNIALGSPLLSRFDLVLVLLDTKNEEWDRIISSF 506
Xenopus  CKLNTRTTILAATNPKGQYDPDESISVNVALASPLLSRFDLVLVLLDTKNEDWDRIISSF 505
         *****************:*** **:***:**.*********:******:**:********
```

Figure 2A

```
Human      ILENKGYPSKSEKLWSMEKMKTYFCLIRNLQPTLSDVGNQVLLRYYQMQRQSDCRNAART 564
Mouse      ILENKGYPSKSENLWSMEKMKTYFCLIRNLHPTLSEVSNQVLLRYYQMQRQSDSRNAART 720
Chicken    ILQNKGCPSKSEKLWSMEKMKTYFCLIKRIQPKLSDESNLILVRYYQMQRQSDCRNAART 566
Xenopus    ILESKGCPRKSDKLWSMEKMKTYFCLIKNLQPKMSQDANVILVRYYQLQRQSSCRNAART 565
           **:.** * **::**************:.::*.:*: .* :*:****:****..******

Human      TIRLLESLIRLAEAHARLMFRDTVTLEDAITVVSVMESSMQGGALLGGVNALHTSFPENP 624
Mouse      TIRLLESLIRLAEAHARLMFRSAVTLEDAVTAVSVMESSMQGGALLGGVNALHTSFPENP 780
Chicken    TIRLLESLIRLAEAHARLMFRDTVTLEDAVTVVSVMESSMQGGALLGAINALHTSFPENP 626
Xenopus    TIRLLESLIRLAEAHARTMYRDVVTTEDAITVVSIMESSMQGGALLGGVNALHTSFPENP 625
           *****************:*:*..** ***:*.**:************.:**********
```

Figure 2A (cont'd)

```
MCM3 KK--FCKAHSK DIFEH LSKSL APSIHG HEYIK KAILC MLLGG NEKVL EN--G TRIRG DIN
MCM7 EE--LRQITEE DFYEK LAASI APEIYG HEDVK KALLL LLVGG VDNSP R---G MKIRG NIN
MCM5 EEEFRR LAAKP DIYET VAKSI APSIYG SSDIK KAIAC LLFGG SRKRL PD--G LTRRG DVN
MCM2 IV---ALSKDE RIGER IFASI APSIYG HEDIK RGLAL ALFGG EAKNP GG--K HKVRG DIN
MCM4 VEKIQQ VSKRD DIYDI LSRSL APSIYE MDDVK KGLLL QLFGG TNKSF HKGAS PRYRG DIN
MCM6 WEKVFE MSQDK NLYHN LCTSL FPTIHG NDEIK RGVLL MLFGG VPKTT MEG-- TSLRG DIN
MCM8 LYAIQE IQSQE NLFQL IVNSL CPTIYG HELVK AGLSL ALFGG CQKYA DDKNR IPIRG DPH
MCM9 DFWVKYRNNPLEGRNE ILASL CPQVFG MFVVK LAVAM VLAGG VQRID SAG-- TRVRG ESH
                     . :  *: * .:.    :* .:   * **  .             **: :

MCM3 VLLIGDPSVAK SQLLRYVL HTAPR AIPTT GRGSS GVGLT AAVTTD QETGE RRLEA GAMVL
MCM7 ICLMGDPGVAK SQLLSYID RLAPR SQYTT GRGSS GVGLT AAVMKD PVTGE MTLEG GALVL
MCM5 LLMLGDPGTAK SQLLKFVE RCSPI GVYTS GKGSS AAGLT ASVMRD PVSRN FIMEG GAMVL
MCM2 VLLCGDPGTAK SQFLKYVE KVASR AVFTT GQGAS AVGLT AYVQRH PVTKE WTLEA GALVF
MCM4 ILMCGDPSTSK SQILKYVH KIAPR GVYTS GKGSS AVGLT AYITRD QDTKQ LVLES GALVL
MCM6 VCIVGDPSTSK SQFLKHVE EFSPR AVYTS GKASS AAGLT AAVVKD EESHE FVIEA GALML
MCM8 ILVVGDPGLGK SQMLQAVC NVAPR GVYVC GNTTT TSGLT VTLSRD TTTGD FGLEA GALVL
MCM9 LLLVGDPGTGK SQFLKYAA KITPR SVLTA GIGST SAGLT VTAVKD --SGE WNLEA GALVL
     : : ***. .***:*       . :. .  . *   ::   ***.      .  : :  :*.*.:::

MCM3 ADRGVV CIDEFDKMSDMDR TAIHE VMEQG RVTIA KAGIQ ARLNAR CSVLA AANPV YGRYD
MCM7 ADQGVC CIDEFDKMMDTDR TAIHE VMEQQ TISIA KAGIM TTLNAR CSILA AANPA YGRYN
MCM5 ADGGVV CIDEFDKMREDDR VAIHE AMEQQ TISIA KAGIT TTLNSR CSVLA AANSV YGRWD
MCM2 ADRGVC LIDEFDKMNDQDR TSIHE AMEQQ SISIS KAGIV TSLQAR CTVIA ASNPI GGRYD
MCM4 SDGGIC CIDEFDKMSDATR SILHE VMEQQ TVTVA KAGII TTLNAR TSILA SANPI GSKYN
MCM6 ADNGVC CIDEFDKMDLKDQ VAIHE AMEQQ TISIT KAGVK ATLNAR TSILA AANPV GGRYE
MCM8 GDQGIC GIDEFDKMGN-QH QALLE AMEQQ SISLA KAGIV CSLPAR TSIIA AANPV GGHYN
MCM9 ADGGLC CIDEFNSIKEHDR TSIHE AMEQQ TISVA KAGLV CKLNTR TTILA ATNPK -GQYD
     .* *:  ****:.:     :  : *.***  :::::***:    * :* :::*::*.   .:::

MCM3 QYRTPM ENIGL QDSLL SRFDL LFIVLD KMDAD NDQEI ADHVL RMHRY RTPGE QDGYA LPL
MCM7 PKKTVE QNIQL PAALL SRFDV LWLIQD KPDRD NDLRL AQHIT YVHQH SK--- ----- ---
MCM5 DTK-GE ENIDF MPTIL SRFDM IFIVKD EHNEQ RDMTL AKHVM NVHLS AR--- ----- ---
MCM2 PSLTFS ENVDL TEPIV SRFDI LCVVRD TVDPV QDEML ARFVV SSHIK HHP-- ----- ---
MCM4 PDLPVT KNIDL PPTLL SRFDL VYLILD RVDET LDRKL ANHIV SMYME DTP-- ----- ---
MCM6 RSKSLK HNVNL SAPIM SRFDL FFILVD ECNEV TDYAI ARRIV DLHAR NEE-- ----- ---
MCM8 KGKTVS ENLKM GSALL SRFDL VFILVD TPNED HDHLL SEHVM AMRSG AKEIQ SVDIT RIN
MCM9 PDESIS VNVAL ASPLL SRFDL VLVLLD TKNED WDRII SSFIL ESKGC PR--- ----- ---
              *: :  .::****:. :: *  :    *  ::  :
```

Figure 2B

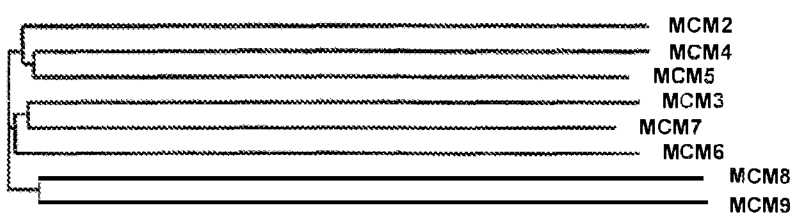

Figure 2C

```
Xenopus     -----LQRLERQQSEDSLESDLGESATNLVGHKVVHS--ECVMEETFSTFEASSLPDETH
Chicken     ----ELQRLDRLQKETYCQLQPEETSFSTITGCLNKNTFESKQKSQSEPSDQQKINSYPQ
Mouse       LLQEELRRLERLQNESVHQCQSHSLEEEVAPGSCRN---DPRDKPRLRTSTQQEQSCS--
Human       ------RRLERLQNQSVHQSQPRVLEVETTPGSLRN---GPGEESNFRTSSQQEINYSTH
                  :**:* *.:   : :     .      :      :     .  ..

Xenopus     LGVTGSAAFIQTPKKTISDMTKSDDTIRKGTITPAEQNRGISTDAESSLKQGNAQPLAGG
Chicken     PSLPKSNCEGDKHPEALRNPTPGNNISTKRLSRLNKRSDDGSLGWFDRLEDRNTDAEETF
Mouse       -WS---STERS-GADSPPGPGL-NRPTSCNNSAENRDGRGDGLDWLDPTSSPEIAP-EST
Human       IFSPGGSPEGSPVLDPPPHLEP-NRSTSRKHSAQHKNNRDDSLDWFDFMATHQSEPKNTV
                    .   ..        .          . . . . .  .     :  .

Xenopus     HLSENNLTKCTDNSLGWFDTLQSIQMSPITKQREGCTAEKLQQEVLPVSTESSCHPADKK
Chicken     WKTSPLPKTSPDN---MALKTMSKSSCSEEGNSSVPRKEDGMRGSLR-TVTLCAPLEQDK
Mouse       IVS-PNVKTTEKN---VNLKISNNKSQGKEKHGPQQRSKLLEAGHLPSSGAMNAPLRSHG
Human       VVS-PHPKTSGEN---MASKISNSTSQGKEKSEPGQRSK-VDIGLLPSPGETGVPWRADN
              :     .. .*     . .               :       *  .          .

Xenopus     VVNLGGRNK------LEVLQASGSSPGGNGRDLSNHTVTCGSSPERNKRDLSNHIVTEHV
Chicken     VSEISSKRTEERKCFSSEANIQDPTSASASVQESVITQRVSKSLQRLHTEKSHRFFTSTQ
Mouse       VKRTKASQ----------AVVVSEAGR-GDEEDS-----VPRRLPKLLKEGSQNVCRST-
Human       VESNKKKR----------LALDSEAAVSADKPDSVLTHHVPRNLQKLCKERAQKLCRNS-
            *      .               . :     .    *              :   : ::..   .

Xenopus     SKKWRRINKDSLCGKNVPSFQPQSENTDSAPVCSSVPLHSTPDVAQRRKRIIAQVEKQSK
Chicken     NSEANALPSVLPVSGLLDLSSDTDSVVGDESNSASAAVKHAVISMRKRSKGQAEKEAKAV
Mouse       -TRVRPLPPTVPLS---------------LSIPSPGSGKRSGTPKRKRRKS-AQVEEPEP
Human       -TRVPAQCTVPSHP---------------QSTPVHSPDRRLDSPKRKRPKSLAQVEEPAI
             ..                             .     . :        ::* :   *: *

Xenopus     AEVEDPDTKAR---LAQLAKFSFKRHSKLVHS--------PAGDTDTASNAQKHDHPVQK
Chicken     SSHEPEITDGESPPAAKLAKFSFRPRTKLDDSSEKKNAEFPLFPSENTVKPGEQPQGEQL
Mouse       EGMETP--------TVKLAKFTFKQKTKLTHSPEGQ-GPIPPSASEIAVDSSKIPQQRTR
Human       ENVKPPGS-----PVAKLAKFTFKQKSKLIHSFEDH-SHVSPGATKIAVHSPKISQRRTR
                :          .:****:*: ::** .*          .    :. : .. :   :

Xenopus     ITLSEKLNNLGRTVNNVDK-------------SSNSVNGSKQQKHVENTSKQTVITQKSN
Chicken     QKDCCPPEKRKMTLTCLGRKGLEK-----QSIGSKGNEEQLSQALGKEMGGNALIHSDVT
Mouse       REAAVPVVAPGKSTSTSGDRCSDQLHGKTKELSRQPPDSNPPREEREQGPKRRVIQPKPE
Human       RDAALPVKRPGKLTSTPGNQISSQPQGETKEVSQQPPEKHGPREKVMCAPEKRIIQPELE
                .        . .                    . :   :      :          . :*  .

Xenopus     FESNTLNAPVHETKLN-----EGCDSRKVSSSTLAKLARFSFSPPPENQAAETSKET---
Chicken     LDVVS--PPPTEKRREGEEKLGGPSTVRVCSSTLENLSKFCFASRPDSKSEAPPTIKTDT
Mouse       LGNQAGHSHLACEKDRKEGVSCGNKSSKVHAGTIARLASFSFTSPSESKSESLPPERKDS
Human       LGNETGCAHLTCEGDKKEEVSGSNKSGKVHACTLARLANFCFTPPSESKSKSPPPERKNR
            :   :  .          .          . .: :* : *: .*: *.*:. .:.::     .

Xenopus     ---------------LILPRAVAPGSKRKCFELNPSTDKTTMSSKSLFSTTDLDDEELDV
Chicken     NNKESH--------SPLLKVHVSNPNKRKSFALGNASKDSVVTRKSLFSIAELDDATLDF
Mouse       RDSRDSRDSRDRCHSPPATTAPVLGQQRQTFQLQQPTERANLSTLSLFTLSELDDEALDF
Human       GERGPS--------SPPTTTAPMRVSKRKSFQLRGSTEKLIVSKESLFTLPELGDEAFDC
                                          .:*: * *  .:.    ::  ***: .:*.*  :*

Xenopus     DWEAEIKGNQRIAT
Chicken     DWD-----------
Mouse       DWEEEMRKKP----
Human       DWDEEMRKKS----
            **:
```

Figure 2D

USE OF A NEW GENE CODING FOR A NEW MEMBER OF THE MCM2-8 FAMILY IN PHARMACEUTICAL COMPOSITIONS

CROSS REFERENCE TO RELATED APPLICATIONS

This application is a division of copending application Ser. No. 11/914,374 filed on Sep. 17, 2008now U.S. Pat No. 8,497,101; which is the 35 U.S.C. 371 national stage of International application PCT/EP2006/004509 filed on May 12, 2006; which claims the benefit of U.S. provisional application Ser. No. 60/680,480 filed May 13, 2005. The entire contents of each of the above-identified applications are hereby incorporated by reference.

FIELD OF THE INVENTION

The present invention relates to the use of a new gene coding for a new member of the MCM2-8 family in pharmaceutical compositions.

BACKGROUND OF THE INVENTION

The Minichromosome maintenance family (MCM2-7) comprises a group of six structurally related proteins required to initiate DNA synthesis in eukaryotes (Kearsey et al., 1998). These proteins function in a complex very likely as a DNA helicase in promoting the opening of the DNA double helix at replication origins. ATP binding (Walker A) and hydrolysis (Walker B) motifs are present in all MCM2-7 members, embedded in a region which is highly conserved in this protein family, also known as the MCM2-7 signature domain (Koonin, 1993). Recently, this protein family has expanded by the identification of a novel member, the MCM8 protein (Gozuacik et al., 2003, Johnson et al., 2003, Maiorano et al., 2005). Unlike MCM2-7, which are widely conserved in eukaryotes, MCM8 is present only in higher multicellular organisms, being absent in worms and yeast.

Very recently, another new member of the MCM protein family, the MCM9 protein, has been identified in humans (Yoshida, 2005). Intriguingly, the predicted human protein (HsMCM9) has been reported to be a rather short homolog of MCM proteins (391 aa against an average of 800 aa in MCM2-7 and MCM8 proteins) and the function of this protein is not known.

Anomalies during DNA replication process are involved in different pathologies such as brains diseases, haematological disorders and cancers. Thus, means to control cellular division would be useful tools for the treatment of pathologies linked to a dysfunction of DNA replication or for pathologies linked to an excessive cellular proliferation.

One of the aims of the invention is to provide a pharmaceutical composition for treating pathologies linked to a dysfunction of DNA replication or to an excessive cell proliferation.

One of the aims of the invention is to provide a method for inhibiting cell proliferation or enhancing DNA replication.

One of the aims of the invention is to provide a method for screening drugs useful in the treatment of pathologies linked to a dysfunction of the replication or to an excessive cell proliferation.

Another aspect of the invention relates to the identification of a MCM2-8 family protein, for which only a truncated form was known, and its specific function.

All these aspects have been obtained by the identification of the full-length MCM9 gene and MCM9 protein.

SUMMARY OF THE INVENTION

The invention relates to the use of the human or animal MCM9 gene, or parts of said gene, or transcripts thereof, or antisense nucleic acids able to hybridize with part of said transcripts, or silencing RNA derived from parts of said transcripts and able to repress said MCM9 gene, or proteins or peptidic fragments translated from said transcripts, or antibodies directed against said proteins or peptidic fragments for the preparation of a pharmaceutical composition for the treatment of a human or animal pathology linked to a dysfunction of the expression of the MCM9 gene, or of human or animal cancers.

The Inventors have performed the complete identification of a novel member of the MCM2-8 family represented by the members MCM2-7 and MCM8, the MCM9 protein. Like MCM8, MCM9 is only present in the genome of higher eukaryotes. This protein contains an MCM8-like ATP binding and -hydrolysis motif implicated in helicase activity. Strikingly, in addition, MCM9 contains a unique carboxy-terminal domain which has only weak homology to MCM2-7 and MCM8, but stretches of amino acids, ranging from 4 to 10 amino acids, are highly conserved within MCM9 homologs. The Inventors have also shown that the very recently reported human MCM9 protein, which resembles a truncated MCM-like protein missing a part of the MCM2-7 signature domain, is an incomplete form of the full length human MCM9 protein hMCM9 described here. Searching the human genome with either the newly identified human MCM9 or other MCM protein sequences, The Inventors have not detected further additional members of this DNA helicase family and suggest that it is constituted of eight members, falling into two different groups, one constituted by the MCM2-7 complex and the other by MCM8 and MCM9, which are present only in higher eukaryotes.

The term "MCM2-7" refers to proteins MCM2, MCM3, MCM4, MCM5, MCM6 and MCM7.

The term "MCM2-8" refers to proteins MCM2, MCM3, MCM4, MCM5, MCM6 MCM7 and MCM8.

DNA helicases have essential roles in nucleic acid metabolism, particularly during DNA replication, also called DNA duplication. Helicases are involved in unwinding DNA at replication origins, allowing DNA synthesis by recruiting DNA polymerases and they are also involved in the whole process of the elongation and termination phases of DNA synthesis when DNA has to be continuously and efficiently unwound. DNA helicases bind to single strand DNA either naked or coated with the single strand DNA binding protein RPA (Replication Protein A) as oligomeric complexes and catalyze the melting of the DNA double helix. This reaction is catalyzed by ATP hydrolysis. ATP binds the helicase at the ATP binding site (Walker A) and ATP hydrolysis occurs at the ATP hydrolysis motif (Walker B).

The helicase activity of a protein can be for example determined by the following test: the protein to test is incubated with a single-stranded DNA substrate annealed to a 40-mer oligonucleotide for 1 hour. The reaction products are then separated on an acrylamide gel. The helicase activity is revealed by the presence of single strand DNA, due to the unwinding of the dimer single-stranded DNA/oligonucleotide.

The ATPase activity can be monitored as described in Maiorano et al. (2005, Cell. 120, 315-28) or alternatively using acidic molybdate and malachite green as follows: the protein to be tested is incubated for 10 minutes at 37.degree. C. in ATPase buffer (50 mM TrisHCl, pH 7.5; 2 mM MgCl.sub.2; 1.5 mM DTT; 0.05% Tween-20; and 0.25% .mu.g/ml BSA) with a dT.sub.25 oligonucleotide or 500 ng of heat-denaturated ssDNA. The reaction is started by the addition of ATP and incubation at 37.degree. C. for up to 25 minutes. The reaction mixture is then transferred into the molybdate/malachite green solution and the absorbance is immediately read at 630 nMm (OD.sub.360) to determine the amount of inorganic phosphate produced during the reaction.

The expression "dysfunction of the expression of the MCM9 gene" relates to an overexpression, a repression or an inhibition of the expression of the MCM9 gene, or relates to the expression of a protein coded by the MCM9 gene, which is not active or only partially active. A dysfunction of the MCM9 gene expression can particularly induce disorders in DNA replication.

A MCM9 protein is active or is an active form when said MCM9 protein has an helicase activity and an ATPase activity and stimulates the formation of a pre-replication complex by loading MCM2-7 onto chromatin. The pre-replication complex is a large protein complex made of the ORC1-6 proteins, Cdc6, Cdt1 and MCM2-7 proteins.

A MCM9 protein is partially active when said MCM9 protein has an helicase activity and/or an ATPase activity lower than the active form.

The helicase activity is lower than the helicase activity of the active form when it represents at least 30%, particularly at least 60%, and more particularly at least 90% of the helicase activity of the active form.

The ATPase activity is lower than the ATPase activity of the active form when it represents at least 30%, particularly at least 60%, and more particularly at least 90% of the ATPase activity of the active form.

A MCM9 protein is not active or is an inactive form when said MCM9 protein has no helicase and/or ATPase activity, or has an helicase activity lower than 30% of the helicase activity of the active form and/or has an ATPase activity lower than 30% of the ATPase activity of the active form, and/or poorly stimulates the formation of a pre-replication complex by loading MCM2-7 onto chromatin.

The dysfunction of the expression of the MCM9 gene can be assayed by the determination of the amount of MCM9 mRNA produced in the cell either by hybridization of total cellular RNA with either a DNA or RNA probe derived from the sequence of the MCM9 gene (Northern blot) or by PCR amplification of the MCM9 mRNA, following its conversion into cDNA by the use of a Reverse Transcriptase (RT-PCR), or by in situ hybridization with either DNA or RNA probes derived from the sequence of the MCM9 gene after fluorescent labelling of these probes. MCM9-specific antibodies can be also used to determine the levels of the MCM9 protein present in cells and/or tissues by western or by in situ hybridization on fixed tissues slices of isolated cells and/or nuclei.

The expression "pathologies linked to a dysfunction of the expression of the MCM9 gene" means that these pathologies result from disorders in helicase activity of the MCM9 gene.

The expression "parts of said gene" means fragments of the MCM9 gene.

The invention also relates to the use of transcripts of the MCM9 gene or of parts of the MCM9 gene. The translation of these transcripts, also called mRNAs, will produce the MCM9 protein, or peptidic fragments of said protein. The proteins or peptidic fragments can be purified from cells expressing said compounds. The peptidic fragments according to the invention can also be synthesized by any method of chemistry well-known in the art.

The invention further relates to the use of antisense nucleic acids. Antisense nucleic acids, also called antisense-oligonucleotides (AS-ONs) pair (hybridize) with their complementary mRNA target, thus blocking the translation of said mRNA or inducing the cleavage by RNase H of said mRNA inside the DNA/RNA complex. In both cases, the use of antisense nucleic acids induces a specific blocking of RNA translation. The antisense nucleic acids according to the invention comprise preferentially 10 to 30 nucleotides. The use of antisense nucleic acids able to hybridize with transcripts of the MCM9 gene thus allows inhibiting the expression of the MCM9 gene.

The expression "antisense nucleic acids able to hybridize with part of said transcripts" means that antisense nucleic acids will pair with part of said transcripts that are complementary under specific hybridation conditions.

Specific hybridation conditions may be determined according to "Molecular cloning", third edition, Sambrook and Russel, CSHL press, 2001.

The invention also relates to the use of silencing RNA, also called interfering RNA, derived from parts of transcripts of the MCM9 gene. RNA interference is a process initiated by double-strand RNA molecules (dsRNAs), which are cut by the cell machinery into 21-23 nucleotides long RNAs, called small interfering RNAs (siRNAs). In the cell, said siRNAs are then incorporated into RNA-Induced Silencing Complex (RISC), in which they guide a nuclease to degrade the target simple strand RNA. The use of silencing RNAs, which are complementary to parts of MCM9 transcripts, allows the specific inhibition of the MCM9 expression.

The invention further relates to the use of MCM9 proteins or peptidic fragments of said protein, which are translated from the transcripts of the MCM9 gene or fragments of said gene, respectively.

The invention also relates to the use of antibodies directed against MCM9 proteins or peptidic fragments of said protein. These antibodies thus bind to the MCM9 protein in the cell, thus inhibiting its helicase function.

The invention relates in particular to the use as defined above for the preparation of a pharmaceutical composition for the treatment of cancers, wherein the helicase activity of MCM9 and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 is inactivated in tumoral cells of the human or animal body by using silencing RNAi according to RNA interference, such as double-stranded RNA (dsRNA) for post-transcriptional gene silencing, or short interfering RNA (siRNA) or short hairpin RNA (shRNA) to induce specific gene suppression, or antisense DNA or RNA, or antibodies, in order to curb the proliferation of said tumoral cells.

In a particular embodiment, the invention aims at inhibiting the proliferation of cancer cells. For that purpose, the helicase activity in tumoral cells is inactivated by specifically blocking MCM9 expression using RNA interference or antisense nucleotides, or by blocking the MCM9 protein with specific antibodies. The level of active MCM9 and consequently the level of helicase activity are decreased and the DNA replication is curbed. The proliferation of the tumoral cells is thus inhibited and a stop of the DNA replication process may also induce apoptosis of the tumoral cells.

Blocking the MCM9 protein or its expression in a cell or in a specific tissue allows blocking of the cell cycle, even before DNA becomes licensed to replicate, which is before the MCM2-7 complex is loaded onto chromatin and DNA synthesis has been initiated. Such cells, which are blocked in this early state of the cell cycle, in particular at the M to G1 phase transition, can not proceed aberrantly in the cell cycle, but will either rest quiescent or be eliminated by apoptosis. In contrast, cells which are blocked or delayed after the licensing of their DNA for replication or even after replication has started, have a high risk to proliferate unfaithfully, to accumulate mutations and to inherit an unstable genome. The term "unstable genome" means that said cells have rearranged the structure of their genome, e.g. by accumulation of chromosomal abnormalities, so that they have a high probability to proliferate abnormally and to generate cancers.

Moreover, blocking MCM9 protein or its expression in a cell constitutes a more efficient treatment against cancer than current drugs that target cells in later phases of the cell cycle, such as the S and G2 phases. In these phases of the cell cycle, DNA replication has already been initiated and therefore cells can rearrange their genome, for example by homologous and/or non-homologous recombination, and therefore have a higher probability to develop resistance to the said drugs. Thus, using a drug that targets MCM9 overcomes the resistance of cancer cells to the said drugs, as the cell cycle is blocked before cancer cells have the possibility to adapt their genome.

The invention particularly relates to antibodies that block the binding of MCM9 on Cdt1 and/or on the chromatin. The inactivation of MCM9 assembly with Cdt1 or with the chromatin allows blocking the entry in the cell cycle before the loading of MCM2-7 onto chromatin, that is to say before licensing.

The term "licensing" means giving to the chromosomes the competence to replicate through the formation of pre-replication complexes onto DNA replication origins.

The pre-replication complex is a large protein complex made of the ORC1-6 proteins, Cdc6, Cdt1 and MCM2-7 proteins.

The protein Cdt is involved in the formation of pre-replication complexes.

The helicase activity in tumoral cells is particularly inactivated by specifically blocking the polypeptides represented by SEQ ID NO 2 or SEQ ID NO 4 or SEQ ID NO 6 or SEQ ID NO 8 or SEQ ID NO 10 or SEQ ID NO 12 SEQ ID NO 14 or SEQ ID NO 16 or SEQ ID NO 18, or their expression.

The polypeptide represented by SEQ ID NO 2 corresponds to the human MCM9 protein (1143 amino acids). The human MCM9 protein contains an ATP binding site (Walker A) and an ATP hydrolysis motif (Walker B).

The polypeptide represented by SEQ ID NO 4 corresponds to the fragment of the human MCM9 protein represented by SEQ ID NO 2, which extends from amino acid 385 to 1143.

The polypeptide represented by SEQ ID NO 6 corresponds to the truncated form of the human MCM9 protein described by Yoshida (2005), which extends from amino acid 1 to 384 of the human MCM9 protein represented by SEQ ID NO 2.

Alignment of the truncated human MCM9 protein described by Yoshida (2005) with the other MCM proteins suggested that this protein might be a truncated MCM like protein missing the carboxy-terminal half of the MCM2-7 signature domain. Within the truncated domain, the ATP binding site is present but the ATP hydrolysis motif is absent. Thus, this truncated form does not contain an ATP hydrolysis motif which is essential for DNA helicase activity (see example 1).

The polypeptide represented by SEQ ID NO 8 corresponds to the murine MCM9 protein (1290 amino acids).

The polypeptide represented by SEQ ID NO 10 corresponds to the fragment of the murine MCM9 protein represented by SEQ ID NO 8, which extends from amino acid 540 to 1290.

The polypeptide represented by SEQ ID NO 12 corresponds to the fragment of the murine MCM9 protein represented by SEQ ID NO 8, which extends from amino acid 1 to 539.

The polypeptide represented by SEQ ID NO 14 corresponds to the *Xenopus* MCM9 protein (1143 amino acids).

The polypeptide represented by SEQ ID NO 16 corresponds to the fragment of the *Xenopus* MCM9 protein represented by SEQ ID NO 14, which extends from amino acid 385 to 1143.

The polypeptide represented by SEQ ID NO 18 corresponds to the fragment of the *Xenopus* MCM9 protein represented by SEQ ID NO 14, which extends from amino acid 1 to 384.

The efficiency of inhibition of the helicase activity, obtained by specifically blocking MCM9 protein or its expression, can be determined by cell proliferation test. For example, classical tests based on BrdU incorporation during DNA synthesis can be used or other tests such as analysis of the DNA content of a cell population by Fluorescence Activated Cell Sorter (FACS), or by incorporation of either a radioactively labelled DNA precursor, or H.sup.3 (tritium) into thrichloroaceticacid (TCA) insoluble materiel, or by scoring the mitotic index of a cell population, or by scoring the increase in the total mass of a cell population (growth curve), or the increase in the rate of protein synthesis, or by scoring the number of Ki67-, PCNA-, MCM2-7- or Cdc6-positive cells.

For the purpose of the invention, the RNA interference is obtained by using interfering RNA chosen among double-strand RNA, short interfering RNA or short hairpin RNA. Interfering RNA can be obtained by chemical synthesis or by DNA-vector technology.

A short hairpin RNA is a simple strand RNA, characterized in that the two ends of said RNA are complementary and can hybridize together, thus forming an artificial double strand RNA with a loop between the two ends.

The invention further relates to the use as defined above for the preparation of a pharmaceutical composition for the treatment of neoplastic diseases such as choriocarcinoma, liver cancer induced by DNA damaging agents or by infection by Hepatitis B virus, skin melanotic melanoma, melanoma, premalignant actinic keratose, colon adenocarcinoma, basal cell carcinoma, squamous cell carcinoma, ocular cancer, non-Hodgkin's lymphoma, acute lymphocytic leukaemia, meningioma, soft tissue sarcoma, osteosarcoma, and muscle rhabdomyosarcoma or of brain diseases such as Alzheimer disease, neuron degenerative diseases and mental retardation, or of hematological disorders.

The above-mentioned pathologies are linked to an excessive proliferation of the cells. The invention particularly relates to the use of a pharmaceutical composition that allows the inhibition of the proliferation of said cells.

The invention also relates to the above-mentioned use, for the preparation of a pharmaceutical composition for the treatment of a human or animal pathology linked to a dysfunction of the expression of the MCM9 gene, wherein the number of functional MCM9 helicases is increased or the activity of MCM9 helicases in cells of the human or animal body is stimulated by administration of functional MCM9 proteins and in particular of polypeptides represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 or of fragments thereof or by gene or cell therapy.

In the above-mentioned use, the dysfunction of the expression of the MCM9 gene is linked to an inhibition or a repression of the expression of an active form of MCM9, or to the expression of an inactive form or a partially active form of the MCM9 protein.

The above-mentioned pathologies result from the absence or the small rate of helicase activity of the MCM9 protein, which may result from the expression of an inactive form of the MCM9 protein or from an expression of said protein which is between 1% to 60% smaller than the expression in normal cells.

The administration of said pharmaceutical composition enables to increase the number of functional MCM9 helicases or to stimulate the activity of MCM9 helicases.

The increased number of functional helicases can be determined by immunoblot with MCM9 specific antibodies on total cell lysates, or by in situ immunostaining on a given cell population or a tissue and/or by isolation of the MCM9 protein by immunopurification with MCM9-specific antibodies and determination of both helicase and ATPase activity in vitro compared to normal cells.

The stimulation of the MCM9 helicase activity is determined by performing an helicase test as described above in the presence of the single strand DNA annealed to an oligonucleotide, the single strand DNA binding trimeric complex RPA, or with DNA polymerases, PCNA, RF-C and/or other replication fork accessory proteins.

The expression "trimeric complex" means a protein complex made of three polypeptides.

The term "gene therapy" refers to the use of DNA as a drug. According to the invention, said DNA comprises the MCM9 gene and is introduced in the cells so that they can express the MCM9 protein. Gene transfer methods are well-known by the man skilled in the art. They comprise physical methods, such as naked DNA, microinjection, shotgun or electrotransfer, and vectorization using non-viral or viral vectors for the gene transfer.

According to the invention, the term "cell therapy" refers to the use of cells having a normal helicase activity to replace or repair cells that present a dysfunction in helicase activity.

According to another embodiment, the present invention relates to the use as defined above for the preparation of a pharmaceutical composition for the treatment of pathologies characterized by a predisposition towards cancer or premature aging and being notably caused by a defect of the helicase function and being particularly selected among Bloom's syndrome, Werner's syndrome, ataxia-telangectasia, xerodermia pigmentosum, Cockayne's syndrome and Rothmund-Thomson's syndrome.

The pathologies characterized by a predisposition towards cancer or premature aging are linked to an inhibition or a repression of the helicase activity, or to an aberrant helicase activity.

The expression "aberrant helicase activity" refers to cases wherein the DNA strand is not entirely synthesized or wherein mistakes are introduced in the new synthesized DNA strand.

The expression "predisposition towards cancer" refers to pathologies wherein the inhibition or the repression of the helicase activity or the aberrant helicase activity can lead to aberrant new synthesized DNA strand that may be responsible of an abnormally proliferation of the cells and then of the induction of cancers.

The expression "defect of the helicase function" refers to an inhibition or a repression of the helicase activity and particularly leads to a cell replication rate that is lower than 20%, by comparison with the replication rate in normal (healthy) cells.

The invention relates to pharmaceutical compositions that enable to restore an helicase activity, particularly by increasing the number of functional MCM9 helicases or to stimulating the activity of MCM9 helicases.

The present invention also relates to a peptide or polypeptide of one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9), or derived from one of the above-defined sequences by insertion, deletion, substitution of one or more amino-acids, or flanked by additional amino-acids at the N-terminus or at the C-terminus or at both termini, provided that the resulting sequence shares at least 55%, in particular at least 65%, in particular at least 80% identity with one of the above-defined sequences and provided that said peptide or polypeptide has substantially the same helicase and/or ATPase activity as the MCM9 protein, and in particular provided that the resulting sequence has a maximum length of 660 amino-acids and a minimum length of 300 amino-acids, or corresponding to a fragment thereof, provided that said fragment has substantially the same helicase and/or ATPase activity as the MCM9 protein.

The expression "peptide or polypeptide derived from one of the above-defined sequences" means that said peptide or polypeptide contains at least one mutation chosen among insertion (or addition) or deletion or substitution of one or more amino-acids, and/or that the peptide or polypeptide is flanked by additional amino-acids at the N-terminus or at the C-terminus or at both termini.

The mutation by substitution in the amino acid sequence can be a substitution by a conservative amino-acid or not.

The additional amino-acids can particularly be chosen among Walker A, Walker B and Zn-finger motifs.

The derived peptides or polypeptides of the invention may be more active forms than the native MCM9 protein and/or possess a modified helicase and/or ATPase activity, such as being able to metabolize other forms of ATP, for example N6-benzyl ATP, N6-cyclopentyl ATP.

The expression "the resulting sequence has a maximum length of 660 amino-acids and a minimum length of 300 amino-acids" particularly refers to peptides or polypeptides that are within the highly conserved MCM2-8-like N-terminus part of MCM9 protein and that comprise the MCM-2-8 family domain.

The highly conserved MCM2-8-like N-terminus part corresponds in the MCM9 protein to amino acids 1-650 for *Xenopus,* 1-805 for Mouse and 1-650 for Human.

The MCM-2-8 family domain corresponds in the MCM9 protein to amino acids 303-606 for *Xenopus,* 458-761 for Mouse and 302-605 for Human.

The expression "substantially the same helicase and/or ATPase activity as the MCM9 protein" means that the helicase and/or ATPase activity of the derived peptide or polypeptide is at least 60%, in particular at least 80% and more particularly at least 90% of the activity of the MCM9 protein.

The present invention also relates to a peptide or polypeptide derived from one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9), by at least one mutation located on a site of phosphorylation by CDKs, in particular said mutations being chosen among the followings:

modification of the conserved threonine (T) in the TP motif to alanine (A) or an equivalent amino acid and modification of the conserved serine (S) in the SP motif to alanine (A) or an equivalent amino acid, modification of the conserved threonine (T) in the TP motif to glutamate (E) or an equivalent amino acid and modification of the conserved serine (S) in the SP motif to glutamate (E) or an equivalent amino acid.

The potential SP phosphorylation sites in MCM9 proteins are located on amino acids 193-194, 478-479, 789-790, 841-842, 859-860, 965-966, 1070-1071 in *Xenopus*, amino acids 49-50, 75-76, 94-95, 348-349, 633-634, 865-866, 899-900, 910-911, 1024-1025, 1073-1074, 1204-1205, 1235-1236 in Mouse, and amino acids 192-193, 477-478, 703-704, 711-712, 762-763, 802-803, 883-884, 890-891, 915-916, 942-943, 952-953, 1073-1074, 1088-1089 in Human.

The potential TP phosphorylation sites in MCM9 proteins are located on amino acids 370-371, 714-715, 735-736, 917-918 in *Xenopus*, amino acids 127-128, 525-526, 1033-1034, 1054-1055 in Mouse, and amino acids 369-370, 673-674, 879-880, 977-978, 1064-1065 in Human.

CDKs (Cyclin-Dependent Kinases) are enzymes involved in the regulation of cell division cycle. CDKs activate and/or inactivate their substrate by phosphorylation. CDKs recognize specific sites, called "site of phosphorylation by CDK", particularly the amino-acids motifs TP and SP.

The mutated forms of MCM9 proteins obtained by mutations located on a site of phosphorylation by CDKs are either inactive, partially active, active or more active than the active non mutated form.

The expression "more active than the active non mutated form" means that the helicase activity of the mutated form represents at least 110%, particularly at least 150% and more particularly at least 200% of the helicase activity of the active non mutated form, and/or that the ATPase activity of the mutated form represents at least 110%, particularly at least 150% and more particularly at least 200% of the ATPase activity of the active non mutated form.

According to the invention, the mutated forms of MCM9 are tested as described above for their helicase and ATPase activity.

The invention further relates to a peptide or polypeptide derived from one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9), by at least one mutation located on a position which is essential for the helicase and/or ATPase activity of MCM9 protein, in particular said mutations being chosen among the followings:

modification of the conserved lysine (K) in the Walker A motif GxxGxGK to alanine (A) or threonine (T) or other non polar or polar neutral amino acids, modification of the conserved aspartic acid (D) in the Walker B motif DExx to alanine (A) or threonine (T) or other non polar or polar neutral amino acids.

The expression "position which is essential for the helicase and/or ATPase activity of MCM9 protein" particularly refers to Walker A and Walker B motifs.

According to the present invention, some mutated forms of the MCM9 protein may lose their helicase function or have an attenuated helicase activity and thus may be used to decrease the proliferation of cells, in particular of cancer cells.

The above modifications of the conserved lysine in the Walker A and/or the conserved aspartic acid in the Walker B lead to mutated forms of the MCM9 which have a highly decreased helicase activity (less than 80% of the helicase activity of the wild-type MCM9 protein), or no helicase activity.

The mutated forms of MCM9 which have a highly decreased helicase activity (less than 80% of the helicase activity of the wild-type MCM9 protein) or no helicase activity may be used in excess by comparison to the native active protein, to decrease the rate of cell proliferation.

The present invention further relates to a peptide or polypeptide containing 65 to 160 amino-acids and comprising a fragment which is essential for the helicase function of the MCM9 protein, said fragment containing in particular sequence SEQ ID NO 20 (amino-acids 300-450 of SEQ ID NO 2) or sequence SEQ ID NO 22 (amino-acids 310-430 of SEQ ID NO 2) or sequence SEQ ID NO 24 (amino-acids 352-417 of SEQ ID NO 2) (helicase region of hMCM9)

or sequence SEQ ID NO 26 (amino-acids 460-610 of SEQ ID NO 8) or sequence SEQ ID NO 28 (amino-acids 470-590 of SEQ ID NO 8) or sequence SEQ ID NO 30 (amino-acids 508-573 of SEQ ID NO 8) (helicase region of MmMCM9)

or sequence SEQ ID NO 32 (amino-acids 300-450 of SEQ ID NO 14) or sequence SEQ ID NO 34 (amino-acids 310-430 of SEQ ID NO 14) or sequence SEQ ID NO 36 (amino-acids 353-418 of SEQ ID NO 14) (helicase region of XMCM9)

or sequence SEQ ID NO 38 (amino-acids 352-359 of SEQ ID NO 2) (walker A motif of hMCM9)

or sequence SEQ ID NO 40 (amino-acids 414-417 of SEQ ID NO 2) (walker B motif of hMCM9)

or sequence SEQ ID NO 42 (amino-acids 508-515 of SEQ ID NO 8) (walker A motif of MmMCM9)

or sequence SEQ ID NO 44 (amino-acids 570-573 of SEQ ID NO 8) (walker B motif of MmMCM9)

or sequence SEQ ID NO 46 (amino-acids 353-360 of SEQ ID NO 14) (walker A motif of XMCM9)

or sequence SEQ ID NO 48 (amino-acids 415-418 of SEQ ID NO 14) (walker B motif of XMCM9), or any fragment derived therefrom by insertion, deletion, substitution of one or more amino acid or sharing at least 50%, in particular at least 65%, in particular at least 80% identity therewith, provided that the resulting fragment substantially retains at least part of the helicase and/or ATPase activity of the MCM9 protein.

The expression “fragment which is essential for the helicase function of MCM9 protein” refers to a fragment that particularly comprises or consists of the Walker A motif and/or the Walker B motif.

Walker A motif is involved in ATP binding. This motif forms a Glycin-rich flexible loop preceded by a .beta.-strand and followed by an .alpha.-helix. The Walker A motif of *Xenopus* and mammalian MCM9 homologs (Gozuacik et al., 2003; Johnson et al., 2003) is a canonical consensus sequence (GxxGxGKS/T).

Walker B motif is involved in ATP hydrolysis and has the following structure: hybrophobic stretch followed by the amino acids signature D[ED], where the presence of at least one negatively charged amino acid in this motif is crucial for its function.

The expression “helicase region” refers to a region of the MCM9 protein that possesses the helicase activity, particularly by comprising the Walker A motif and/or the Walker B motif.

The invention also relates to a nucleic acid encoding the peptides or polypeptides as defined above.

The term “nucleic acid” refers to DNA or RNA.

The invention relates to single stranded or double stranded nucleic acids.

The invention further relates to a nucleic acid of one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), or derived from one of the above-defined sequences by insertion, deletion, substitution of one or more nucleotide, or flanked by additional nucleotides at the 5' end or 3' end or at both ends, provided that the resulting sequence shares at least 40%, in particular at least 60%, in particular at least 80% identity with one of the above-defined sequences and provided that the resulting sequence encodes a peptide or polypeptide which has substantially the same helicase and/or ATPase activity as the MCM9 protein, and in particular provided that the resulting sequence has a maximum length of 1980 nucleotides and a minimum length of 900 nucleotides, or corresponding to a fragment thereof, provided that said fragment encodes a peptide or polypeptide which has substantially the same helicase and/or ATPase activity as the MCM9 protein.

The nucleotide sequence represented by SEQ ID NO 1 (nucleotides 1-4798) encodes the human MCM9 helicase represented by SEQ ID NO 1.

The nucleotide sequence represented by SEQ ID NO 3 corresponds to the nucleotides 1153-4798 of the human MCM9 sequence represented by SEQ ID NO 1 and encodes the polypeptide of sequence SEQ ID NO 4.

The nucleotide sequence represented by SEQ ID NO 5 corresponds to the nucleotides 1-1152 of the human MCM9 sequence represented by SEQ ID NO 1 and encodes the polypeptide of sequence SEQ ID NO 6.

The nucleotide sequence represented by SEQ ID NO 7 (nucleotides 1-3873) encodes the murine MCM9 helicase represented by SEQ ID NO 8.

The nucleotide sequence represented by SEQ ID NO 9 corresponds to the nucleotides 1618-3873 of the murine MCM9 sequence represented by SEQ ID NO 7 and encodes the polypeptide of sequence SEQ ID NO 10.

The nucleotide sequence represented by SEQ ID NO 11 corresponds to the nucleotides 1-1617 of the murine MCM9 sequence represented by SEQ ID NO 7 and encodes the polypeptide of sequence SEQ ID NO 12.

The nucleotide sequence represented by SEQ ID NO 13 (nucleotides 1-3432) encodes the *Xenopus* MCM9 helicase represented by SEQ ID NO 14.

The nucleotide sequence represented by SEQ ID NO 15 corresponds to the nucleotides 1153-3432 of the *Xenopus* MCM9 sequence represented by SEQ ID NO 13 and encodes the polypeptide of sequence SEQ ID NO 16.

The nucleotide sequence represented by SEQ ID NO 17 corresponds to the nucleotides 1-1152 of the *Xenopus* MCM9 sequence represented by SEQ ID NO 13 and encodes the polypeptide of sequence SEQ ID NO 18.

The expression “nucleic acid derived from one of the above-defined sequences” means that said nucleic acid contains at least one mutation chosen among insertion (or addition) or deletion or substitution of one or more nucleotide, and/or that the nucleic acid is flanked by additional nucleotides at the 5' end or at the 3' end or at both ends.

The mutation by deletion or by addition in the nucleic acid can eventually induce a shift in the opening reading frame of the MCM9 nucleotide sequence, in a way that the peptide or polypeptide encoded by said nucleic acid has substantially the same function as the MCM9 protein.

The mutation by substitution in the nucleotide sequence can lead to a silencing substitution due to the degeneracy of the genetic code, or to a substitution by a conservative amino-acid or a non conservative amino-acid in the peptide or polypeptide encoded by said nucleotide acid.

The additional nucleotides can particularly be chosen among nucleotides that encode Walker A, Walker B and Zn-finger motifs.

The expression “the resulting sequence has a maximum length of 1980 nucleotides and a minimum length of 900 nucleotides” particularly refers to nucleotide sequences encoding peptides or polypeptides that are within the highly conserved MCM2-8-like N-terminus part of MCM9 protein and that comprise the MCM-2-8 family domain.

The invention also relates to a nucleic acid derived from one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), by at least one mutation, the resulting sequence encoding a peptide or a polypeptide having at least a mutation located on a site of phosphorylation by CDKs, in particular chosen among the followings:

modification of the conserved threonine (T) in the TP motif to alanine (A) or an equivalent amino acid and modification of the conserved serine (S) in the SP motif to alanine (A) or an equivalent amino acid, modification of the conserved threonine (T) in the TP motif to glutamate (E) or an equivalent amino acid and modification of the conserved serine (S) in the SP motif to glutamate (E) or an equivalent amino acid.

The invention further relates to a nucleic acid derived from one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), by at least one mutation, the resulting sequence encoding a peptide or a polypeptide having at least a mutation located on a position which is essential for the helicase and/or ATPase activity of MCM9 protein, in particular said mutations being chosen among the followings:

modification of the conserved lysine (K) in the Walker A motif GxxGxGK to alanine (A) or threonine (T) or other non polar or polar neutral amino acids, modification of the conserved aspartic acid (D) in the Walker B motif DExx to alanine (A) or threonine (T) or other non polar or polar neutral amino acids.

The invention further relates to a nucleic acid which contains 180 to 480 nucleotides and which comprises a fragment which encodes a part of the MCM9 protein which is essential for its helicase function, said fragment containing in particular sequence SEQ ID NO 19 (nucleotides 898-1350 of SEQ ID NO 1) or sequence SEQ ID NO 21 (nucleotides 928-1290 of SEQ ID NO 1) or sequence SEQ ID NO 23 (nucleotides 1054-1251 of SEQ ID NO 1) (helicase region of hMCM9)

or sequence SEQ ID NO 25 (nucleotides 1387-1830 of SEQ ID NO 7) or sequence SEQ ID NO 27 (nucleotides 1408-1770 of SEQ ID NO 7) or sequence SEQ ID NO 29 (nucleotides 1522-1719 of SEQ ID NO 7) (helicase region of MmMCM9)

or sequence SEQ ID NO 31 (nucleotides 898-1350 of SEQ ID NO 13) or sequence SEQ ID NO 33 (nucleotides 928-1290 of SEQ ID NO 13) or sequence SEQ ID NO 35 (nucleotides 1057-1254 of SEQ ID NO 13) (helicase region of XMCM9)

or sequence SEQ ID NO 37 (nucleotides 1054-1077 of SEQ ID NO 1) (walker A motif of hMCM9)

or sequence SEQ ID NO 39 (nucleotides 1240-1251 of SEQ ID NO 1) (walker B motif of hMCM9)

or sequence SEQ ID NO 41 (nucleotides 1522-1545 of SEQ ID NO 7) (walker A motif of MmMCM9)

or sequence SEQ ID NO 43 (nucleotides 1708-1719 of SEQ ID NO 7) (walker B motif of MmMCM9)

or sequence SEQ ID NO 45 (nucleotides 1057-1080 of SEQ ID NO 13) (walker A motif of XMCM9)

or sequence SEQ ID NO 47 (nucleotides 1243-1254 of SEQ ID NO 13) (walker B motif of XMCM9)

or any fragment derived therefrom by insertion, deletion, substitution of one or more nucleotide or sharing at least 45%, in particular at least 60%, in particular at least 80% identity therewith, provided that the resulting fragment encodes a peptide or polypeptide which substantially retains at least part of the helicase and/or ATPase activity of the MCM9 protein.

The invention relates to a nucleic acid which is complementary to a nucleic acid as defined above.

The term "complementary" means that said nucleic acid is able to pair or hybridize to a nucleic acid by Watson and Crick or other base-pair interactions, thus being able to form a double-stranded structure with this nucleic acid.

The invention also relates to a nucleic acid which is capable of hybridizing with a nucleic acid as defined above under appropriate hybridizing conditions.

The "appropriate hybridizing conditions" may be determined according to "Molecular cloning", third edition, Sambrook and Russel, CSHL press, 2001.

The invention described herein also relates to an expression vector comprising a nucleic acid as described above and the elements which are necessary for its expression in a cell.

The expression "elements which are necessary for its expression" particularly refers to regulatory sequences to which the nuclei acid is operably linked.

The term "operably linked" means that the nucleotide sequence is linked to a regulatory sequence in a manner which allows the expression of the nucleic acid sequence. The regulatory sequences are well known by the man skilled in the art. They include promoters, enhancers and other expression control elements.

The invention also provides a cell transformed by a nucleic acid as defined above or by an expression vector as defined above.

The host cell according to the present invention includes prokaryotic host cells (bacterial cells), such as *E. coli, Streptomyces, Pseudomonas, Serratia marcescens* and *salmonella typhimurium* or eukaryotic cells such as insect cells, in particular baculovirus-infected Sft9 cells, or fungal cells, such as yeast cells, or plant cells or mammalian cells.

The invention further relates to a recombinant protein obtained by the expression of the expression vector as defined above.

The DNA vector containing the MCM9 gene or fragments thereof as defined above is used to produce a recombinant form of the protein by recombinant technology. Recombinant technology comprises the steps of ligating the nucleotide sequence into a gene construct such as an expression vector and transforming or transfecting said gene construct into host cells. The host cells that express the protein are then lysed and the recombinant protein is isolated and purified, for example by chromatography.

The present invention relates to an antibody or antigen-binding fragment which binds to an MCM9 protein or part of an MCM9 protein or to a modified active MCM9 protein, in particular to a peptide or polypeptide as defined above and in particular to the polypeptide represented by SEQ ID NO 2 or SEQ ID NO 4 (corresponding to amino-acids 1-1143 or 385-1143 of hMCM9).

The antibody can be polyclonal or monoclonal and the term "antibody" is intended to encompass both polyclonal and monoclonal antibodies. The terms "polyclonal" and "monoclonal" refer to the degree of homogeneity of an antibody preparation, and are not intended to be limited to a particular method of production.

The present invention relates to antibodies which bind to MCM9 protein or part of an MCM9 protein, or to a mutated form of the MCM9 protein or part thereof. A mammal, such as a rabbit, a mouse or a hamster, can be immunized with an immunogenic form of the protein, such as the entire protein or a part of it. The protein or part of it can be administered in the presence of an adjuvant.

The term "immunogenic" refers to the ability of a molecule to elicit an antibody response. Techniques for conferring immunogenicity to a protein or part of it which is not itself immunogenic include conjugation to carriers or other techniques well known in the art.

The immunization process can be monitored by detection of antibody titers in plasma or serum. Standard immunoassays, such as ELISA can be used with the immunogenic protein or peptide as antigen to assess the levels of antibody.

The invention relates in particular to a monoclonal or polyclonal antibody directed against an MCM9 protein or against a peptide or polypeptide comprising part of an MCM9 protein, and in particular against a peptide or polypeptide as defined above.

The invention also relates to a method for the in vitro or ex vivo production of catalytically active MCM9 helicase in foreign expression systems, such as bacteria (*E. coli*) or insect cells (Sf9), or equivalent or in vitro systems for coupled transcription/translation of the MCM9 cDNA, such as rabbit reticulocytes systems or lysate of *E. coli* cells or translation of the MCM9 mRNA into *xenopus* oocyte or egg extracts, possibly under form of a tagged recombinant protein, comprising the steps of:

lysis of cells expressing MCM9 proteins in the following buffer or equivalent, 20 mM TrisHCl pH 8.5, 100 mM KCl, 5 mM .beta.-mercaptoethanol, 5-10 mM imidazole, 10% glycerol (v/v) proteases inhibitors;

purification of the soluble MCM9 proteins by nickel affinity chromatography technology or equivalent or similar affinity chromatography technology;

elution of bound proteins in 10 mM TrisHCl pH 8.5; 100 mM KCl; 5 mM .beta.-mercaptoethanol; 100-250 mM imidazole, 10% glycerol (v/v) proteases inhibitors;

supplementation of purified MCM9 proteins, with or without cleaved tag, with 0.1 mg/ml of BSA;

desaltation on a Bio-spin P30 column (Biorad) equilibrated with 20 mM TrisHCl pH 7.4, 150 mM NaCl, 0.5 mM EDTA, 1 mM DTT, 0.01% Triton X-100 for helicase and ATPase activities, or in XB (100 mM KCl, 0.1 mM CaCl-.sub.2, 2 mM MgCl.sub.2, 10 mM Hepes-KOH, 50 mM sucrose, pH 7.7) for egg extracts reconstitution experiments; and supplementation of the protein with 25% glycerol and storage at −20.degree. C. mercaptoethanol; The rabbit reticulocytes systems and lysate of *E. coli* cells are ex vivo cell free extracts that can transcribe a given cDNA into mRNA and translate the mRNA into a protein. Such a system may be valuable to produce catalytically active protein to perform in vitro activity assays.

The recombinant proteins are tagged either at the N- or C-terminal with well-known sequence Tag, such as Hist-Tag, Myc-Tag, Flag-Tag, Tap-Tag, GST-tag, MAL-Tag, in order to facilitate the purification of the protein. Preferentially, the sequence tag can be removed by an enzymatic or chemical reaction involving the use of thrombin and/or TEV protease or similar enzymatic activities.

The expression "catalytically active" means that the corresponding recombinant protein can bind and hydrolyze continuously ATP resulting in helicase activity, such as displacement of an oligonucleotide annealed to single stranded DNA, or able to melt double stranded DNA in vitro, and/or that the protein can catalyze formation of pre-replication complexes in vitro and/or in vivo, determined by the ability of MCM2-7 proteins to associate with chromatin in vivo and/or in vitro.

According to another embodiment, the invention relates to a pharmaceutical composition comprising as active substance a peptide or polypeptide or a nucleic acid or an expression vector or a cell or an antibody or antigen-binding or a monoclonal or polyclonal antibody, as defined above, in association with a pharmaceutically acceptable vehicle.

The pharmaceutical preparation of the present invention can be formulated with a physiologically acceptable medium, such as water, buffered saline, polyols (glycerol, propylene glycol, liquid polyethylene glycol) or dextrose solutions. Preferentially, the pharmaceutical preparation is formulated in a vector which will allow the delivery of said preparation inside the target cells. The pharmaceutical preparation can be administered by intradermal, intramuscular, intraperitoneal, intravenous, subcutaneous or oral way.

The pharmaceutical preparation may also be administered as part of a combinatorial therapy with other agents, such as inhibitors or activators of cell proliferation. Inhibitors of cell proliferation can be chosen among aphidicoline, cis-platinum, etoposides, lovastatin, mimosine, nocodazole. Activators of cell proliferation can be chosen among growth factors such as EGF (Epidermal Growth Factor), FGF (Fibroblast Growth Factor), NGF (Nerve Growth Factor) and analogues, and lipopolysaccharides.

The invention relates to a method for the screening of drugs useful in the treatment of human or animal pathology linked to a dysfunction of the expression of the MCM9 gene, said method comprising contacting of the potential drugs with cells such as cancer cells or transformed cells and especially liver, brain, muscle, skin or gut cells wherein a decrease of the expression of the MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof, or of antisense nucleic acids able to hybridize with part of said gene or transcripts, or of silencing RNA derived from parts of said transcripts and able to repress said MCM9 gene, and screening the drugs able to inhibit the proliferation of said transformed cells.

According to another embodiment, the present invention relates to a method for the in vitro or ex vivo screening of drugs useful in the treatment of human or animal pathology linked to a dysfunction of the expression of the MCM9 gene, said method comprising contacting of the potential drugs with cells such as:

cancer cells or cells wherein recombinant and/or mutated active forms of MCM9 helicase, which is in particular represented by one of the following sequences: SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, or fragments thereof, are introduced to increase the helicase activity in said cells or transformed cells and especially liver, brain, muscle, skin or gut cells wherein an increase of the expression of an active form of MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof, and screening the drugs able to inhibit the proliferation of said cells.

The expression "to increase the helicase activity" means that the helicase activity is increased from 10% to 90%, in particular from 50% to 90%, by comparison with the basal helicase activity of wild-type MCM9 protein.

The expression "basal helicase activity" refers to the helicase activity in cells cultured in usual conditions, particularly according to the manufacturer protocol.

The expression "increase of the expression of an active form of MCM9 helicase" means that the number of active helicase is increased, thus increasing the helicase activity as defined above.

In the above embodiment, the term "drugs" refers to inhibitors of DNA replication whose target is the DNA helicase. The inhibitors of DNA replication can be chosen among dibenzothiepin and its analogues, non-hydrolysable NTPs such as .gamma.ATP, DNA-interacting ligands such as nogalamycin, daunorubicin, ethidium bromide, mitoxantrone, actinomycin, netropsin and cisplatin, 4,5,6,7-tetrabromo-1H-benzotriazole (TBBT), peptides binding DNA that inhibit the unwinding of the double helix by the helicase, bananins and its derivatives, the aminothiazolylphenyl-containing compounds BILS 179 BS and BILS 45 BS, 5'-O-(4-fluorosulphonylbenzoyl)-esters of ribavirin (FSBR), adenosine (FSBA), guanosine (FSBG) and inosine (FSBI), CDKs inhibitors such as staurosporines and its derivatives.

In order to screen potential drugs inhibiting cell proliferation, proliferation tests are carried out on the proliferative cells.

According to another embodiment, the present invention relates to a method for the in vitro or ex vivo screening of drugs useful in the treatment of human or animal pathology linked to a dysfunction of the expression of the MCM9 gene, said method comprising contacting of the potential drugs with:

cells wherein recombinant and/or mutated inactive forms of MCM9 helicase are introduced to decrease the helicase activity in said cells or transformed cells and especially liver, brain, muscle, skin or gut cells wherein an increase of the expression of an inactive MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof, or, transformed cells and especially liver, brain, muscle, skin or gut cells wherein a decrease of the expression of an active form of MCM9 helicase is induced by transformation of said cells with antisense nucleic acids able to hybridize with part of said gene or transcripts, or of silencing RNA derived from parts of said transcripts and able to repress said MCM9 gene, or cells wherein antibodies directed against MCM9 protein, which is in particular represented by one of the following sequences: SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, or fragments thereof, are introduced to decrease the helicase activity in said cells, and screening the drugs able to stimulate the proliferation of said cells.

The expression "to decrease the helicase activity" means that the helicase activity is decreased from 10% to 90%, particularly from 30% to 90%, more particularly from 60% to 90%, by comparison with the basal helicase activity of wild-type MCM9 protein.

The expression "decrease of the expression of an active form of MCM9 helicase" means that the number of active helicase is decreased, thus decreasing the helicase activity as defined above.

In the above embodiment, the term "drugs" refers to activators of DNA replication whose target is the DNA helicase. The activators of DNA replication can be chosen among caffeine, tamoxifen in uterine tissues, leptomycin B, CDKs inhibitors such as staurosporines.

In order to screen potential drugs stimulating cell proliferation, proliferation tests are carried out on the non proliferative cells.

The invention also relates to the use of an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18, for inhibiting cell proliferation or allowing to increase replication of the DNA, particularly in vitro or ex vivo, wherein the agonist or antagonist enters the cell, said antagonist causing the inhibition of DNA replication and said agonist contributing to the restoration of cell proliferation or to the ability of the cell to replicate DNA in unfavorable conditions.

The expression "restoration of cell proliferation" means that the proliferation of the cells, for example blocked by the action of an antagonist, can be re-established, so that cells can replicate the DNA and divide.

The expression "unfavorable conditions" refers to conditions wherein cells are not competent to proliferate, because they are in a state of quiescence, such as differentiated cells, or because the proliferation of said cells has been temporarily blocked by an inhibitor of cell proliferation, such as mimosine, lovastatine, aphidicolin, hydroxyurea, or DNA damaging agents and/or alkylating agents.

The invention particularly relates to antagonists of MCM9 that block the binding of MCM9 on cdt1 and/or on the chromatin.

The invention further relates to a method for inhibiting cell proliferation or allowing a better replication of the DNA, comprising administering an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 in a way that the agonist or antagonist enters the cell, said antagonist causing the inhibition of DNA replication and said agonist contributing to the restoration of cell replication or to the ability of the cell to replicate DNA in unfavorable conditions.

The invention also relates to a method for inhibiting cell proliferation or allowing a better replication of the DNA in vitro or ex vivo, comprising administering an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 in a way that the agonist or antagonist enters the cell, said antagonist causing the inhibition of DNA replication and said agonist contributing to the restoration of cell replication or to the ability of the cell to replicate DNA in unfavorable conditions.

The invention also relates to a method for diagnosing, in particular in vitro or ex vivo, a pathology or a risk of developing a pathology linked to a disorder in the expression of the MCM9 protein, consisting in assessing a possible surexpression of MCM9 or a possible alteration of the normal activity of MCM9 and/or a possible mutation on a MCM9 gene and/or a possible mutation on a MCM9 protein in particular resulting in a possible genomic instability and/or a possible neoplastic transformation.

The expression "genomic instability" refers to the loss and/or alteration of the genetic material during cell proliferation and division.

The surexpression of MCM9 is assessed by measuring the level of expression of the MCM9 gene by Northern blot and/or RT-PCR in vivo and/or in vitro, or by in situ hybridization of cells with DNA and/or RNA probes, as well as by determining the amount of MCM9 protein produced in the cell by western blot and/or by in situ hybridization with MCM9-specific antibody (immunofluorescence). The levels of expression of the MCM9 gene and/or of the corresponding protein in cells surexpressing MCM9 are compared to the levels of non-pathologic cells isolated from the same patient.

The alteration of the normal activity of MCM9 is assessed by determining the DNA helicase activity of the MCM9 protein in vitro and/or in vivo, and/or by assessing the ability of MCM9 to catalyze the formation of pre-replication complexes onto chromatin in vivo and/or in vitro. This latter can be determined by detection of components of the pre-replication complex, such as the MCM2-7 proteins, and/or that of the PCNA protein, onto chromatin by western blot and/or immunofluorescence in vivo and/or in vitro.

The mutation on a MCM9 gene is assessed by extraction and isolation of the DNA from the cells and determination of the DNA sequence of the MCM9 gene, and/or by isolation of the total mRNAs from the cells and amplification of the MCM9 gene by RT-PCR, and/or by analysis of the polymorphysm of the MCM9 gene by restriction digest (RFLP).

The mutation on a MCM9 protein in particular resulting in a possible genomic instability is assessed by comparison of the sequence of the MCM9 gene isolated from pathologic cells with that isolated from non-pathologic cells obtained from the same patient. Mutations in the DNA sequence coding for the known motifs of the MCM9 protein, such as the Zn-finger domain and/or the MCM2-8 signature domain and/or the helicase domain are potential candidates for mutations causing genomic instability.

The neoplastic transformation is assessed by the ability of cells to proliferate indefinitely in vitro and/or the ability of said cells to induce tumors when injected into animals.

The invention also relates to a method for the screening of biologically active agents useful in the treatment of human or animal pathology linked to a dysfunction of the expression of the MCM9 gene, said method comprising:

administering a potential agent to a non-human transgenic animal model for MCM9 gene function, particularly chosen among a MCM9 knock-out model and a model of exogenous and stably transmitted MCM9 sequence, and determining the effect of said agent on the development of the transgenic animal and/or the development of diseases such as those defined above, and in particular the development of cancer.

The term "non-human animal" includes all mammals expect for humans, advantageously rodents and in particular mice.

The term "transgenic animal" denotes an animal into whose genome has been introduced an exogenous gene construct, which has been inserted either randomly into a chromosome, or very specifically at the locus of an endogenous gene.

In a MCM9 knock-out model, the exogenous gene construct has been inserted at the locus of the MCM9 gene, resulting in the impossibility of expressing this MCM9 gene, since it is either interrupted or entirely or partially replaced by a construct such that it no longer allows expression of the endogenous gene, or alternatively a construct which, in addition to the deletion of the endogenous gene, introduces an exogenous gene. Such animals will be referred to as "knock-out" animals or animals in which the abovementioned endogenous gene is invalidated.

A model of exogenous and stably transmitted MCM9 sequence can be obtained by transfection of the cells of the animal (such as stem cells or in vitro cultured cell lines) with a DNA plasmid bearing wild-type or mutated forms of the MCM9 gene under control of promoter sequence of the MCM9 gene or promoters for standard reporter genes which are constitutively expressed or whose expression can be controlled by induction with inducers of the expression of the above mentioned promoters, integration of such plasmid in the chromosome of such cells so that this transgene is stably transmitted to the cell progeny.

The effect of the agent is determined by morphological and/or phenotypical analysis of the transgenic animal, and/or by molecular analysis by measure of cell proliferation and/or cell death and/or cell differentiation and/or cell apoptosis, and/or determination of the karyotype of the animal, that is to say analysis of the number and structure of the chromosomes of cells chosen from the whole embryo or tissues of the animal.

The MCM9 protein is a novel member of the MCM2-8 protein family with an unique C-terminal domain.

Figure 1A:
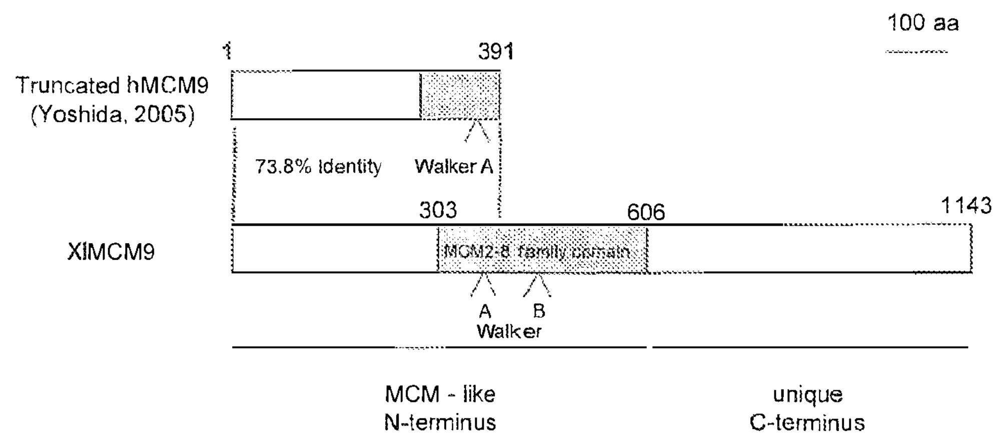
FIG. 1A and FIG. 1B

FIG. 1A: Alignment of the previously reported truncated human MCM9 protein truncated hMCM9 (Yoshida, 2005) with the *Xenopus* MCM9 protein (X1MCM9). The MCM2-8 signature domain is shown in grey. The ATP binding (Walker A) and hydrolysis (Walker B) motifs are indicated. Numbers indicate aminoacids.

Figure 1B:
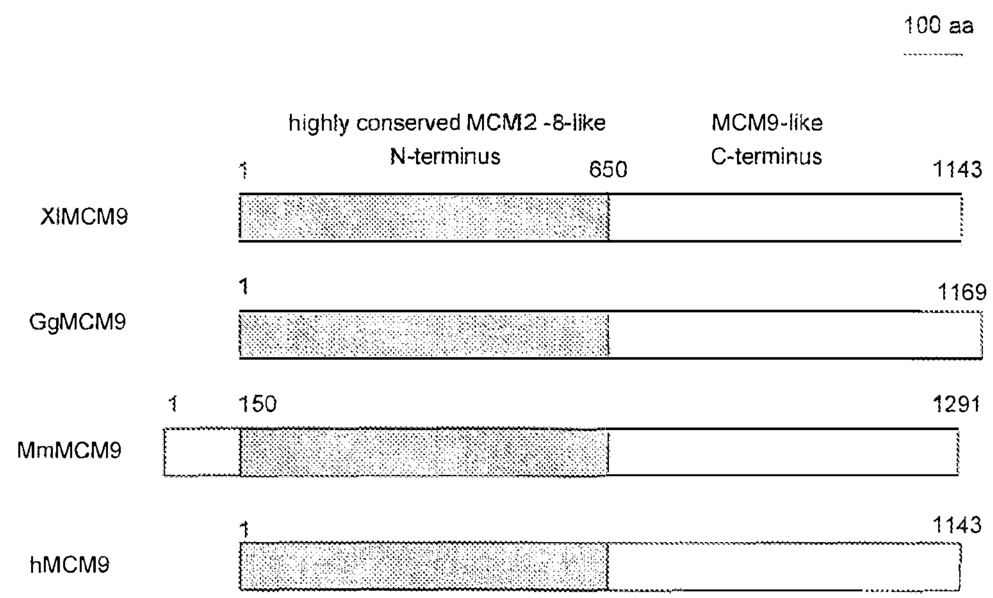

FIG. 1B: Alignment between full length MCM9 homologs in different organisms: *Xenopus* (X1MCM9), chicken (GgMCM9), mouse (MmMCM9) and human (hMCM9) proteins. Numbers indicate aminoacids.

FIG. 2A, FIG. 2B and FIG. 2C

Alignment of MCM9-like proteins in different organisms.

FIG. 2A: Alignment of the conserved N-terminal half of MCM9 proteins from Humans (SEQ ID NO: 49), Mouse (SEQ ID NO: 50), Chicken (SEQ ID NO: 51) and *Xenopus* (SEQ ID NO: 52), obtained by ClustalW. The Walker A and B motifs are underlined. Stars indicate identity, while similar amino acids are indicated by a single or double dot. The number of points indicates the degree of similarity defined by the program Clustal W.

FIG. 2B: Alignment of MCM9 (SEQ ID NO: 60) with MCM2-8 proteins (MCM3 (SEQ ID NO: 53), MCMI (SEQ ID NO: 54), MCM5 (SEQ ID NO: 55), MCM2 (SEQ ID NO: 56), MCM4 (SEQ ID NO: 57), MCM6 (SEQ ID NO: 58) and MCM8 (SEQ ID NO: 59)) from *Xenopus* within the central region of MCM2-8 proteins and the N-terminal of MCM9. Alignment was performed as in FIG. 2A. Walker A and B motifs are underlined. The alignment region corresponds to amino acids 449-673 for MCM2, 285-520 for MCM3, 446-673 for MCM4, 320-545 for MCM5, 335-563 for MCM6, 321-550 for MCM7, 336-650 for MCM8 and 291-550 for MCM9.

FIG. 2C: Phylogram of human MCM2-7, MCM8 and MCM9. The Phylogram was calculated with ClustalW.

FIG. 2D: Alignment of the C-terminal regions of MCM9 from *Xenopus* (SEQ ID NO: 61), Chicken (SEQ ID NO: 62), Mouse (SEQ ID NO: 63) and Humans (SEQ ID NO: 64).

Alignment was performed as in FIG. 2A. The alignment region corresponds to amino acids 650-1143 for *Xenopus* MCM9, 800-1291 for Mouse MCM9, 650-1169 for Chicken MCM9 and 650-1143 for Human MCM9.

FIG. 3

Characterization of the antibody raised against a peptide corresponding to amino acids 605 to 1143 of the *Xenopus* MCM9 protein.

Western Blot analysis of egg extract (1 .mu.l and 2 .mu.l) with pre-immune serum (lane 1 and 2) and serum against MCM9 (3IP1, lane 3 and 4).

FIG. 4

MCM9 associates with chromatin.

Western blot of chromatin fractions prepared after 40, 60 or 120 minutes after addition of sperm chromatin to egg extract. MCM9 and ORC2 proteins were detected with specific antibodies. The last lane (40+geminin) shows that MCM9 associates with chromatin also when replication is blocked by geminin, however to a lesser extent.

Figure 5A:
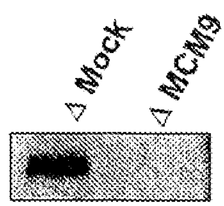
Figure 5B:
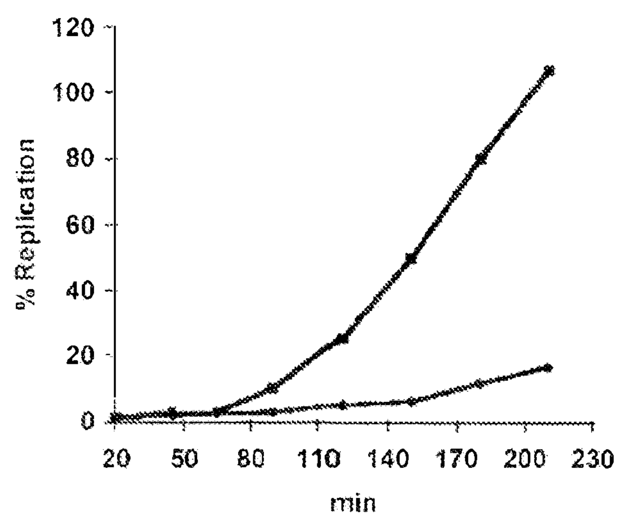

FIGS. 5A and 5B

Depletion (.DELTA.) of MCM9 from egg extracts abolishes DNA replication.

FIG. 5A: Western blot of egg extract after incubation with non-specific antibody (Mock) or antibody against MCM9. The MCM9 protein can be completely removed from the egg extract as seen when depletion is carried out using an antibody against MCM9 (.DELTA. MCM9).

FIG. 5B: Replication kinetics in Mock-depleted egg extract (squares) and MCM9-depleted egg extract (circles). Depletion of MCM9 abolishes DNA replication.

FIG. 6

Depletion of MCM9 from an egg extract does not (quantitatively) codeplete other proteins involved in DNA licensing/replication.

Egg extract after Mock-depletion (A Mock) or MCM9-depletion (.DELTA. MCM9) was mixed with SDS-sample buffer, loaded on a SDS-PAGE and blotted. Following western blot analysis was performed for MCM9, as well as for proteins known to be involved in DNA licensing or replication (all MCM2-7, MCM8, Cdt1 and ORC2).

FIG. 7

Depletion of MCM9 from egg extract inhibits the loading of the MCM2-7 complex onto chromatin.

A western blot analysis of chromatin assembled either in a Mock-depleted (.DELTA. Mock) or MCM9-depleted (.DELTA. MCM9) egg extract, was carried out as described in FIG. 4. The presence of MCM2-7, Cdt1, CDC6 and ORC2 in the chromatin was detected using the corresponding antibodies.

Chromatin which was assembled in MCM9-depleted extract does not contain MCM2-7 proteins, less Cdt1, but more CDC6.

FIG. 8

Association of MCM9 with chromatin is dependent on ORC.

A western blot analysis of chromatin assembled either in a Mock-depleted (.DELTA. Mock) or ORC2-depleted (.DELTA. ORC2) egg extract was carried out as in FIG. 4. Chromatin which was assembled in an ORC2-depleted extract does not contain MCM9 and is also devoid of pre-RC proteins (MCM2-7, Cdt1, CDC6). Histon H3 (H3) is shown as a loading control and ORC2 as a depletion control.

FIG. 9

MCM9 interacts with Cdt1 in egg extract.

Western blot analysis of immunopurifications (IP) of MCM9, Cdt1, and a Mock-purification (done with an unspecific antibody), using an MCM9 antibody (upper lane) or a cdt1 antibody (lower lane). In the MCM9 purification, a substantial amount of Cdt1 is present, showing that these two proteins interact in egg extract.

FIG. 10

GST-TEV-MCM9 can be purified from Baculovirus-infected SF9 cells.

Coomasie stained SDS-PAGE showing GST-TEV-MCM9 recombinant protein bound to GSH-beads, after incubation of the GSH-beads with SF9 cell-lysate, and the GST-TEV-MCM9 protein after elution from the GSH-beads (eluate GSH).

Figure 11A:
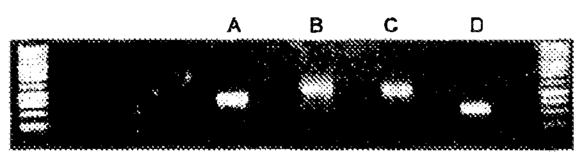
Figure 11B:
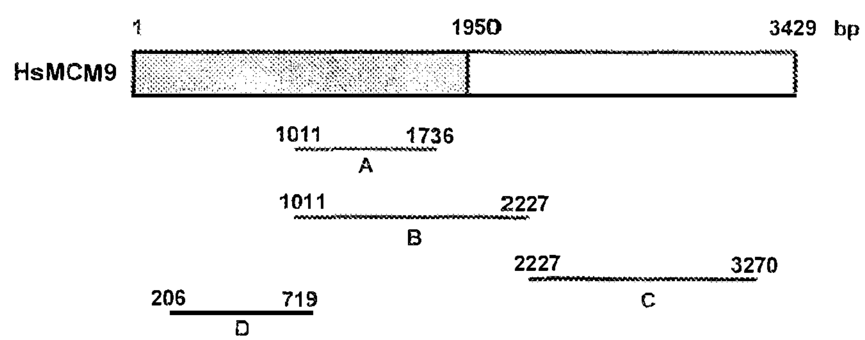

FIGS. 11A and 11B

RT-PCR analysis of human MCM9 RNA.

FIG. 11A: RT-PCR analysis of parts of human MCM9 (fragments A, B, C and D)

FIG. 11B: location of the fragments amplified by PCR in FIG. 11A on the human MCM9 cDNA.

EXAMPLES

Example 1

Identification of MCM9 Protein, a Specific Vertebrate Member of the MCM8 Protein Family Screening the public EST databases, the inventors have identified a homolog of the truncated human MCM9 protein in *Xenopus laevis*. Unlike the reported truncated human MCM9, the *Xenopus* MCM9 (X1MCM9) is much longer and contains all the features of MCM proteins, in particular the entire MCM2-7 signature domain, made of both ATP binding (Walker A) and hydrolysis (Walker B) motifs. In addition, *Xenopus* MCM9 is closer related to MCM8, since both possess the canonical Walker A and B motifs (whereas MCM2-7 possesses a deviant Walker A motif).

By careful screening the genome of other vertebrates and mammals in silico, the Inventors have now identified conserved homologs of the entire MCM9 protein also in chicken, mouse and human, whose primary structure closely resembles that of the *Xenopus* MCM9 protein. These findings indicate that the MCM9 protein is a canonical MCM protein also in humans, closer related to human MCM8 than to human MCM2-7 proteins, and that the previously reported truncated human MCM9 protein represents only a part of the entire human MCM9.

Experimental Procedures

Identification of MCM9 Homologs

To identify homologs of MCM9, database searches were performed using the program BLAST. Either EST databases or genomic databases for indicated organisms were searched. In addition, ab initio proteins were generated to identify hypothetical proteins by BLAST with the GNOMON routine. GNOMON uses multiple heuristics to find the best self-consistent set of transcripts and protein alignments in a certain genomic region. The program calculates splice sites and identifies the cases where two exons of the protein alignment are as closed as maximum 50 by having different frames. Since such short introns are extremely rare, in these cases GNOMON introduces frame shifts in the sequence to combine multiple exons, which allows to create consistent transcripts also from genomic regions containing errors in its sequence. Proteins predicted by GNOMON were then confirmed by identification of EST sequences in EST databases and by GEO Blast Special Search for Short Regions of High Homology To identify smaller regions of homology and to identify EST sequences within a database, also MEGABLAST was used (Zhang et al., 2000) which is especially suited for the identification of shorter, but highly similar sequences in a given genome database. Megablast was designed to optimize the alignment of sequences which differ only slightly due to e.g. sequencing errors Protein Alignment Protein alignments were performed using the program ALIGN (Pearson et al., 1997) or CLUSTALW (Higgins et al., 1994), available on the server of the Institute of Human Genetics (IGH), Montpellier or the EMBL-EBI server. Identification of protein domains and motif searches were performed either using InterProScan available on the EMBL-EBI server scanning the InterPro database of protein families, domains and functional sites (Mulder et al., 2005) or MotifScan, using the Hits-database from the Swiss Institute of Bioinformatics (SIB).

Results

Identification of a *Xenopus* Homolog of Reported Truncated Human MCM9

To identify a *Xenopus* homolog of the recently described truncated human MCM9 protein (Yoshida, 2005), the Inventors performed a search using the BLAST program with the truncated hMCM9 protein sequence as a query against the Expressed Sequences Tagged (EST) *Xenopus* database. Consequently, the Inventors identified the cDNA clone IMAGE6637819 (accession number BC070720 on GenBank), coding for a protein of 1143 amino acids derived from a mRNA expressed in *Xenopus* eggs. Sequence alignment with X1MCM proteins show that the first 835 aa of X1MCM9 share 25.6% identity with full length X1MCM8 (835 aa) while the identity with X1MCM2-7 proteins is in average 10.5%. These results strongly indicate that X1MCM9 is a distinct member of the MCM family in *Xenopus*. (FIG. 1A). X1MCM9 shows a strong identity (73.8%) in its first amino-terminal 391 aa with the reported truncated hMCM9.protein (391 aa, Yoshida, 2005). However, unlike the reported truncated hMCM9, the X1MCM9 protein contains a much longer carboxy-terminal extension which shows in its first part a high homology to the other MCM proteins. Within this region, X1MCM9 contains an intact MCM2-7 family signature domain (aa 303-aa 606) harboring Walker A and B motifs. The MCM2-7 family domain is the highest conserved region among the members of the MCM2-7 family.

Interestingly, the Walker A motif of X1MCM9 (GxxGxGKS, aa 354-360), is a canonical consensus site as the one found in MCM8 proteins, but different from that found in MCM2-7 proteins, which is a deviant consensus site (GxxGxAK/S). The Inventors conclude that this protein is the *Xenopus* homologue of truncated hMCM9. Importantly, the size of the X1MCM9 protein is bigger than that of other MCM proteins. This is essentially due to a C-terminal extension after the MCM homology region, which does not share a clear homology to other MCM proteins and seems to be a unique feature of this protein (FIG. 1A).

Identification of MCM9 Homologs in the Genome of Other Vertebrates and Mammals

Given that the length of X1MCM9 is much bigger than reported for the truncated hMCM9 (Yoshida, 2005), the Inventors investigated whether this was a special feature of the *Xenopus* protein or if a longer MCM9 homolog protein could be also identified in other organisms. Therefore, the Inventors performed databank searches using BLAST with the X1MCM9 protein sequence against databases of several organisms.

A record (XM.sub.—419764 on GenBank) in the chicken genomic database was found derived from an annotated sequence (NR.sub.—060336 on GenBank, located on chromosome 3 between 61.196 and 61.290 kbp). Within this region, GNOMON predicts a mRNA coding for a 1169 aa long protein, which could be supported by multiple EST evidences (e.g. BU378776, BU478046, BU271359, on GenBank). This chicken MCM9 (GgMCM9) shares 54.1% identity with X1MCM9. Like X1MCM9, the chicken protein consists of two main parts: an N-terminal part which is highly conserved (aa 1-626 share 81.2% identity with X1MCM9) and a C-terminal region which is much less conserved within MCM proteins as well as in respect to other MCM9 homologs (FIG. 2D).

Next, searching the mouse genome database, the Inventors found two entries (BAB31238.1 and NP.sub.—954598 on chromosome 10 between 53.544 and 53.679 kbp, on GenBank), both coding for unnamed protein products. The proteins corresponding to these sequences showed 87% identity with the N-terminus of GgMCM9, and 47.9% identity with the carboxy-terminus of GgMCM9, respectively. Searching the mouse EST database with these sequences, a number of partially overlapping expressed sequences were identified (e.g. BY720667, CB244669, CX2225903, on GenBank) and the entire corresponding protein was re-joined in silico, resulting in a 1291 aa long hypothetical protein possessing over 60% identity with the GgMCM9 protein and 47% to X1MCM9. MmMCM9 shares the general organization of a highly conserved N-terminus and a much less conserved C-terminus in respect to the other identified MCM9 proteins and other MCM family members (FIG. 1B). In addition, the first 150 aa of this protein are not present in the other MCM9 proteins. Importantly, its first 386 aa are 100% identical with the reported 386 aa containing mouse MCM9 (Yoshida, 2005).

These findings suggest that X1MCM9-like proteins can also be found in the genome of other vertebrates and mammals. Therefore, the Inventors re-investigated the human databases using the full X1MCM9 sequence as a query to search for a complete human MCM9 protein. First, homologs of X1MCM9 were searched in the human genome with BLAST. Two overlapping sequence entries on chromosome 6 were found (NT.sub.—025741 and NT.sub.—086697, on GenBank) revealing highest alignment significance. The identified human sequences were coding for amino acid stretches, which were highly similar to X1MCM9 over the entire length of the protein, strongly suggesting that a human MCM9 with a similar size as the *Xenopus* protein exists.

Next, using the GNOMON routine within BLAST (which corrects artificial frame shifts, see Materials and Methods 2.1), to generate ab initio proteins, a human MCM9 was found at exactly the same position on chromosome 6, highly similar to X1MCM9. This protein was in its N-terminus 100% identical to the first 385 aa of the reported truncated 391 aa long hMCM9 (Yoshida, 2005). Consequently, multiple partially overlapping EST sequences corresponding to the human MCM9 region were also identified (e.g. CV030253, CX756843 (which contains the full Walker A and B motif), DR008069, on GenBank), demonstrating that a mRNA of the protein inclusive an intact Walker B motif and an elongated C-terminus is indeed transcribed.

Finally the Inventors searched by BLAST the human genome with the hMCM9 protein generated by GNOMON.

Over 30 BLAST hits on chromosome 6 were found, covering nearly all the hMCM9 sequence generated by GNOMON, giving direct EST evidence from aa 1 to aa 1060. Some hits were located at the locus previously annotated as MCMDC1 (as MCM-containing domain 1) at the position 6q 22.31, corresponding to the 7 exons of truncated hMCM9 previously described (Yoshida, 2005). In addition, more hits were identified further downstream of the MCMDC1 locus and beyond the ASF1 gene, which is located in an intron of HMCM9 and transcribed in the opposite direction, corresponding to 6 more exons of the hMCM9 gene. Finally, on the map of the human chromosome 6 at position 6q22.31, the entire open reading frame of the HsMCM9 gene with the corresponding protein is also annotated as the entry hmm17631 in the GNOMON model in Map viewer, as member of the MCM2/3/5 family. Thus, this new hMCM9 gene consists of 13 exons, giving rise to a mRNA of 4789 nucleotides containing 1366 nucleotides of untranslated 3' sequences. The corresponding hMCM9 protein consists of 1143 aa, thus having a similar length as the identified proteins in *Xenopus*, mouse and chicken. These results show that the recently reported truncated hMCM9 (Yoshida, 2005) is an N-terminal fragment of the whole protein and that the stop-codon reported in this sequence and considered as the end of the protein, corresponds to the end of exon seven.

The here identified full length hMCM9 shares 55.0% identity with X1MCM9 and 63.8% identity with the MmMCM9 over its entire length (FIGS. 2A and 2B). These findings show that all new identified members of the MCM9 family (Xenopus, chicken, mouse and human) are similar in length and highly conserved.

Characterization and Classification of the New MCM9 Proteins

The most striking feature of the MCM9 protein in different organisms is their highly conserved N-terminus (aa 1-650), which contains all classical features of MCM2-7 and MCM8 proteins, including Zn finger-like domains, the Walker A and B motifs as well as a full MCM2-7 family domain (FIG. 1A and FIG. 2A). Only the mouse protein appears to contain additional 150 aa on its N-terminus. However, MCM9 shares a much higher homology to MCM8 than to the other MCM2-7 proteins (FIG. 2A and FIG. 2C) and it is only present in vertebrates. Thus, MCM8 and MCM9 represent a distinct sub-family of MCM DNA helicases, perhaps to fulfill special needs which came up with the more complex biology and development of multicellular organisms, especially in vertebrates. Indeed, MCM8 and MCM9 are present in vertebrates, but are absent in yeast, worms and flies. In contrast, the C-terminal half of all identified MCM9 proteins (aa 650 to the end), is less conserved (FIG. 2B), unique and not present in other MCM proteins, although a weak homology to human MCM8 exists. No obvious protein signatures or motifs could be identified with a significant score within this part. However, the C-terminus contains several short, nevertheless highly conserved stretches. The elongated C-terminus of this newly identified MCM9 protein might not be directly involved in helicase activity, but in binding to other factors or helicases.

CONCLUSIONS

The newly identified MCM9 protein seems to be generally present in vertebrates (e.g. also in dog within the contig NR.sub.—139836, on GenBank), cow (XP.sub.—584574, on protein sequence database) and zebra fish (within the contig CAAK01001524.1, on GenBank) whereas in *D. melanogaster, C. elegans* and *S. cerevisiae* there appears to be no MCM9 homolog. The previously identified HsMCM9 protein, which is shorter in size than MCM proteins, was annotated as MCMDC1 in the GenBank public database (NM.sub.—153255), suggesting that this protein may be a protein functionally unrelated to MCM proteins, but sharing some homology with them, in particular in one part of the MCM2-7 signature. These findings clarify this issue by establishing that MCM9 is a canonical MCM protein, more related to MCM8 than to the six MCM2-7 proteins and whose motifs and sequences are conserved in vertebrates and mammals, including humans.

Example 2

MCM9, a Protein Essentially Involved in Pre-RC Formation and Initiation of DNA Replication

Experimental Procedures

Plasmid Constructs

The following vectors containing *Xenopus* MCM9 or parts of the gene were made:

for expression in *E. coli*: pET24d-MCM9 (EcoRI/SalI, aa1-1143), pProEXHTGST-TEV-MCM9 (EcoRI/SalI, aa1-1143), pProEXHT-Strict1 (EcoRI/XhoI, aa605-779), pProEXHT-C-term (EcoRI/XhoI, aa 605-1143), and for expression using Baculovirus: pFastBacGST-TEV-MCM9 (EcoRI/SalI, aa1-1143), pFastBacHT-MCM9 (EcoRI/SalI, aa1-1143), pFastBacGST-TEV-NMCM9 (EcoRI/EcoRI, aa1-654), pFastBacHT-NMCM9 (EcoRI/EcoRI, aa1-654).

The PET plasmids were obtained from Novagen and Invitrogen.

Cloning was performed using standard PCR techniques. As template to amplify the ORF of X1MCM9 cDNA clone with the Image ID 6643889 (on Pubmed) was used. Via PCR, restriction sites (see above for each construct) were introduced before and after the ORF. The vector and the PCR product were then digested with the indicated restriction enzymes and ligated using T4 ligase. Ligations were transformed into *E. coli* DH5.alpha., clones were grown, plasmids purified and analyzed for successful ligation using restriction digests.

Antibodies

Polyclonal antibodies against two different recombinant parts of the *Xenopus laevis* MCM9 (aa605-779) and (aa605-1143) were raised in rabbits.

Rabbits were injected with around 1 mg of protein mixed with Freud's adjuvant (1:1) in intervals of 3 weeks. The first bleed (3IP1) was taken 12 days after the third injection and was used for western blotting and depletion.

In intervals of several weeks, antigen was re-injected and more serum collected, which equally was used for western blotting and depletion.

Figure 3:
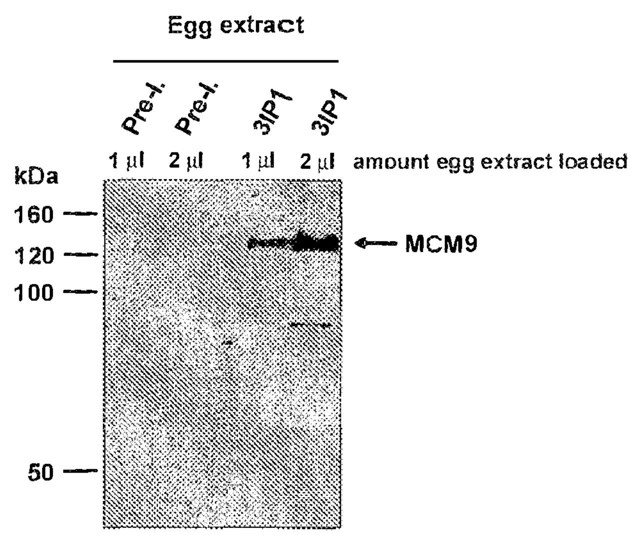

Both antibodies recognize the protein in *Xenopus* egg extracts. For example, the Western blot in FIG. 3 shows that the antibody raised against the amino acids 605 to 1143 of MCM9 recognizes the MCM9 protein in *Xenopus* egg extracts.

Polyclonal antibodies against the human hMCM9 protein were raised in rabbits as described above, using the following peptides for immunization:

human peptide 1 (aa 989-1008):

(SEQ ID NO: 65)

ETKEVSQQPPEKHGPREKVM, human peptide 2 (aa 809-828):

(SEQ ID NO: 66)

PWRADNVESNKKKRLALDSE.

Antibodies against ORC-2 were obtained from Dr. J. Walter, Harvard University, Boston, USA. Antibodies against CDC6 were described in Lema tre et al., 2002, Nature. Antibodies against all MCM2-7 were described in Maiorano et al., 2000, JBC, antibodies against MCM8 in Maiorano et al., 2005, Cell, and antibodies against cdt1 in Maiorano et al., 2000, Nature.

The Mock antibody is obtained from rabbit serum before immunization with the MCM9 recombinant protein.

RT-PCR

Extraction of total human RNA from HeLa cells was performed using standard techniques with the RNeasy Mini Kit (Qiagen, Cat. Nr. 74104). Purified RNA (1 ug) was reversed transcribed using SuperScript III First-Strand Synthesis System (Invitrogen, Cat. Nr. 18080-051) with poly (dT) primers. Next, PCR reaction was performed using Pfu Turbo DNA Polymerase (Stratagene, Cat. Nr. 600250) with specific primers for hMCM9.

To obtain the fragments of human MCM9 shown in FIG. 11, the following primers were used:

for fragment A:

(SEQ ID NO: 67)

5': TAC AGG AAC ACG GGT CAG (SEQ ID NO: 68)

3': GAA ACA TCA GGC GAG CAT for fragment B:

(SEQ ID NO: 69)

5': TAC AGG AAC ACG GGT CAG (SEQ ID NO: 70)

3': TGC CAT GAA ATC AAA CCA ATC for fragment C (SEQ ID NO: 71)

5': TTT GAT TTC ATG GCA ACT CAT (SEQ ID NO: 72)

3': CGC ATT GGA GCT GTG GTT GTA for fragment D:

(SEQ ID NO: 73)

5': TTG ATA GTG CAC TGC GAA GGT (SEQ ID NO: 74)

3': TGC ATT ACA ATC CCG TAA A

Cloning of the entire cDNA of human MCM9 was performed using the following primers:

(SEQ ID NO: 75)

5' GGGGGGGTCGACCAGCCATTACCTAGATTCAAG 3' (forward)

(SEQ ID NO: 76)

5' GGGGGGCTCGAGCAGAAAGCTTTTCCCAACTA 3' (reverse)

Proteins Expression and Purification

For expression in *E. coli*, vectors were transformed into *E. coli* codon plus strain (Stratagene) and cultivated in minimal medium. Expression cultures were grown at 37 degrees to an OD of 0.3, then shifted to room temperature and at an OD of 0.8 induced for two hours with 0.5 mM IPTG. Cells were harvested by centrifugation and frozen in liquid N2.

For expression in SF9 cells, a construct was transformed in DH10bac *E. coli* (Kit Invitrogen), colonies containing recombinant virus DNA were identified and the DNA purified and transfected into SF9 cells. After virus amplification, 500 ml cultures of infected SF9 were grown and frozen in liquid N2.

To purify recombinant GST (Glutathione S-transferase)-MCM9 from Sf9 cells, cells were lysed in Dicis-Buffer (300 mM NaCl, 150 mM KoAC, 20 mM Tris pH 6.8, 2 mM MgCl2, 10% Glycerol, 0.01 NP40)+0.1% NP40.) by sonication. After centrifugation (15 min, 15 000 rpm in an SS34 rotor), the supernatant was incubated either with Glutathione-Sepharose 4B (Amersham Bioscience) or Ni-NTA Sepharose (Qiagen) for 40 min at 4.degree. C. After binding, the GSH (glutathione)-beads were washed with 20 volumes of Dicis-Buffer. Elution of the GST-fusion protein was performed using one volume of Dicis-buffer+20 mM GSH at RT for 15 min for the Glutathione-Sepharose beads. Ni-NTA beads were washed with Dicis-buffer+20 mM imidazol and eluted stepwise with Dicis-buffer supplemented with 50, 100 and finally 150 mM.

To purify recombinant His-MCM9, the protocol is similar to the above protocol of GST-MCM9 purification, except that the protein is bound to Ni-beads (resins) and is eluted with increasing concentrations of imidazole in the buffer (50, 100, 150 mM imidazole).

*Xenopus* Egg Extracts and DNA Replication Reactions

Egg extracts, were prepared and used as previously described (Mechali and Harland, 1982; Menut et al., 1988). Depletion and reconstitution experiments were as previously described (Maiorano et al., 2000b).

Briefly, *Xenopus* low speed egg extracts were supplemented with cycloheximide (250 mu.g/ml) and double-depleted with anti-MCM9 serum coupled to Protein-A sepharose beads or recombinant protein A sepharose (Pharmacia, 50% beads to extract ratio), for 40 minutes at 4.degree. C.

*Xenopus* Egg Extracts

Egg extracts were prepared as described previously (Menut et al, 1998). Upon thawing, egg extracts were supplemented with cycloheximide (250 mu.g/ml) and an energy regeneration system (10 .mu.g/ml creatine kinase; 10 mM creatine phosphate; 1 mM ATP; 1 mM MgCl.sub.2). To follow DNA replication by incorporation of .alpha.-[.sup.32P] dNTP into newly replicated DNA, 1 mu.l of .alpha.-[.sup.32P] dNTP (3000 Ci/mmol) was added to standard reaction of 50 .mu.l.

Immunopurification Procedures

Immunopurification was performed by incubation of egg extract with the indicated antibody (MCM9, Cdt1 or unspecific antibody) for 60 min at 4 degrees. Then, Protein A-sepharose was added and incubated for another 60 min at 4 degrees. Next, the Protein A-sepharose was extensively washed with XB and bound proteins were finally eluted with SDS-sample buffer. Samples were separated on a SDS-PAGE and analyzed by western blotting.

Chromatin Purification

Sperm DNA was incubated in egg extract for the 40, 60 or 120 minutes. Chromatin fractions were obtained by diluting with 5 volumes of XB buffer (10 mM HEPES-KOH pH 7.7, 100 mM KCl, 0.1 mM CaCl 2, 1 mM MgCl2, 5% sucrose)+0.3% Triton X-100, keeping them for 5 min at 4.degree. C. Next, the extraction was purified by centrifugation through a sucrose cushion (0.7 M Sucrose in XB). The pellet containing the chromatin fraction was solubilized in sample buffer for SDS-PAGE analysis.

Results:

Biological Characterization of MCM9

Figure 4:
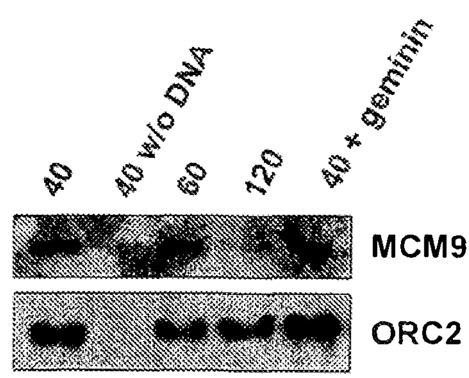

In FIG. 4, chromatin purifications after indicated times were blotted against MCM9 and ORC2 (as a loading control). Lanes 3 and 4 show that MCM9 associates with chromatin. Lane 2 is a negative control (no DNA added). The last lane (+Geminin) shows that MCM9 is also present on chromatin when replication is blocked by the addition of geminin. However, MCM9 is likely to be less stable than other proteins involved in DNA replication like ORC, CDC6 or Cdt1.

FIG. 5B shows that depletion of MCM9 from an egg extract abolishes DNA replication. First, the complete depletion of MCM9 was assessed by a western blot of egg extract, after incubation with non-specific antibody (Mock) or antibody against MCM9. The results shown in FIG. 5A indicate that the MCM9 protein can be completely removed from the egg extract as seen in .DELTA. MCM9. Then, a replication kinetics of Mock-depleted egg extract (squares) and MCM9-depleted egg extract (circles) was carried out. The results shown in FIG. 5B indicate that depletion of MCM9 abolishes DNA replication.

Figure 6:
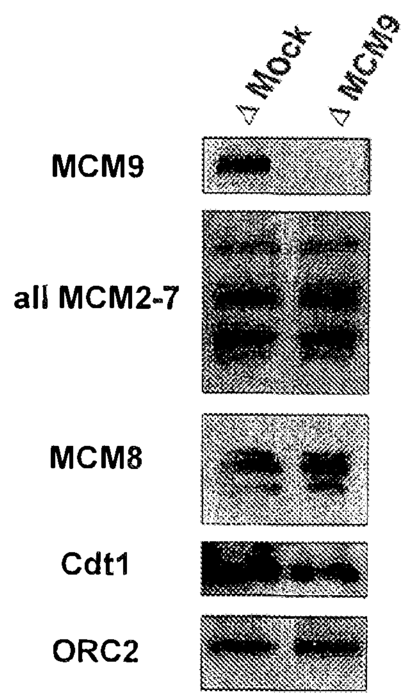

A western blot analysis of egg extract either Mock-depleted or MCM9-depleted for other proteins involved in DNA licensing or replication was then carried out. The results shown in FIG. 6 indicate that the depletion of MCM9 from an egg extract does not (quantitatively) codeplete other proteins involved in DNA licensing/replication. Thus, MCM9 is essential for DNA replication and, by depleting only MCM9, DNA replication is abolished.

Figure 7:
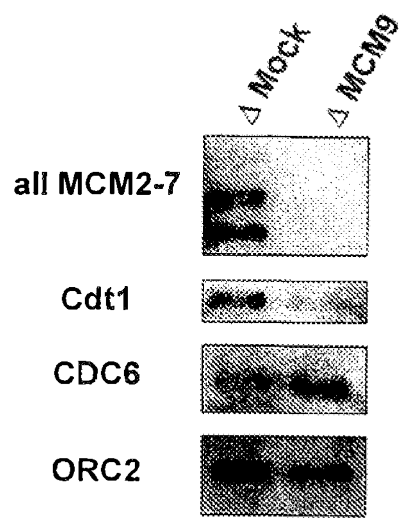

FIG. 7 shows a western blot analysis of chromatin assembled either in a Mock-depleted or MCM9-depleted egg extract. Chromatin which was assembled in MCM9-depleted extract does not contain MCM2-7 proteins and less Cdt1 than in Mock-depleted egg extract. Thus, depletion of MCM9 from egg extract inhibits the loading of the MCM2-7 complex on chromatin. This result indicates that blocking MCM9 protein allows stopping DNA replication at an early stage, before the production of single strand DNAs.

Figure 8:
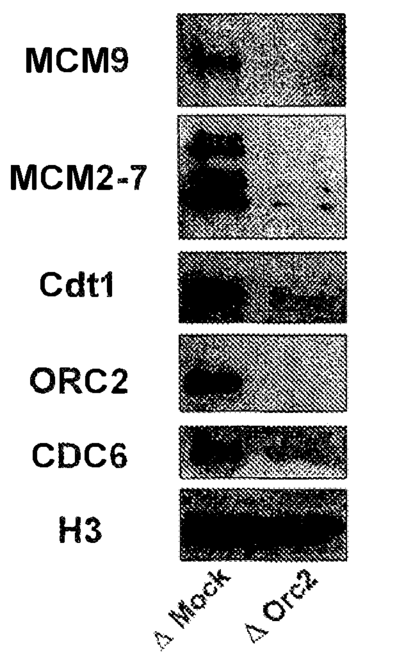

FIG. 8 shows a western blot analysis of chromatin assembled either in a Mock-depleted or ORC2-depleted egg extract. Chromatin which was assembled in an ORC2-depleted extract is devoid of pre-RC proteins (Cdt1, CDC6, MCM2-7) and also does not contain MCM9. Histon H3 (H3) is shown as a loading control. Association of MCM9 with chromatin is thus dependent on ORC (Origin Recognition Complex). MCM9 certainly binds chromatin at the replication origin via ORC.

Figure 9:
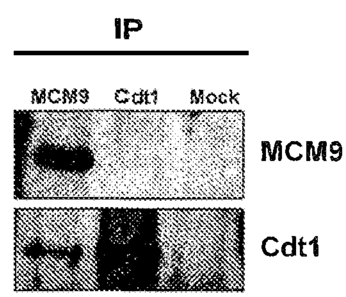

In FIG. 9, MCM9 is shown to interact with Cdt1 in egg extract: a western blot analysis of immune purifications of MCM9, Cdt1 and a Mock-purification (done with an unspecific antibody) was carried out. In the MCM9 purification, a substantial amount of Cdt1 is present, showing that these two proteins interact in egg extract (FIG. 9). Thus, MCM9 binds chromatin by associating with cdt1, a protein which is necessary for replication.

Recombinant Expression of MCM9

Figure 10:
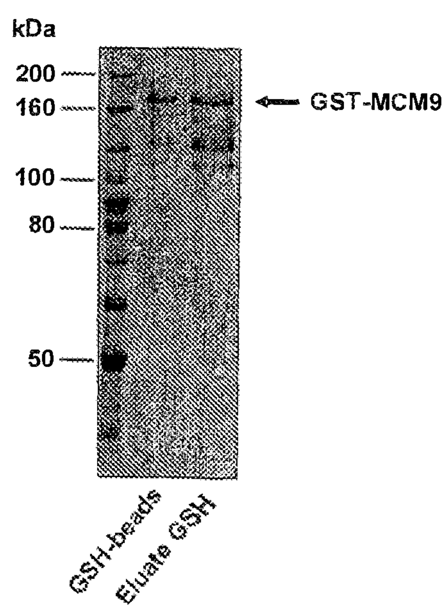

GST-TEV-MCM9 is purified from Baculovirus-infected SF9 cells. In FIG. 10, Coomasie stained SDS-PAGE shows GSH-beads loaded with GST-TEV-MCM9 after incubation with SF9 cell-lysate and the GSH-eluated protein GST-TEV-MCM9.

Evidence for the MCM9 in Human Cells

An RT-PCR analysis was performed on human cDNA with specific primers pairs corresponding to different fragments of the human MCM9. These fragments represented in FIG. 11B overlap on almost the full-length human MCM9 protein. The results shown in FIG. 11A reveal the presence of specific bands corresponding to the different parts of the human MCM9.

REFERENCES

Gozuacik, D., Chami, M., Lagorce, D., Faivre, J., Murakami, Y., Poch, O., Biermann, E., Knippers, R., Brechot, C. and Paterlini-Brechot, P., 2003. Nucleic Acids Res, 31, 570-579.

Higgins D., Thompson J., Gibson T. Thompson J. D., Higgins D. G., Gibson T. J., 1994. Nucleic Acids Res., 22, 4673-4680.

Johnson, E. M., Kinoshita, Y. and Daniel, D. C., 2003. Nucleic Acids Res, 31, 2915-2925.

Kearsey, S. E. and Labib, K., 1998. Biochim. Biophys. Acta, 1398, 113-136.

Koonin, E. V., 1993. Nucleic Acids Res., 21, 2541-2547.

Maiorano, D., Moreau, J., and Mechali, M., 2000. Nature, 404, 622-625.

Maiorano, D., Cuvier, O., Danis, E. and Mechali, M., 2005. Cell, 120, 315-328.

Mechali, M., and Harland, R. M., 1982. Cell, 30, 93-101.

Menut, S., Lemaitre, J. M., Hair, A., and Mechali, M., 1988. Oxford University Press, Ed J D Richter.

Mulder, N. J., Apweiler, R., Attwood, T. K., Bairoch, A., Bateman, A., Binns, D., Bradley, P., Bork, P., Bucher, P., Cerutti, L., 2005. Nucleic Acids Res., 33, D201-205.

Pearson, W. R., Wood, T., Zhang, Z. and Miller, W., 1997. Genomics, 46, 24-36.

Yoshida, K., 2005. Biochem. Biophys. Res. Corn., 331, 669-674.

Zhang, Z., Schwartz, S., Wagner, L. and Miller, W., 2000. J. Comput. Biol., 7, 203-214.

The invention claimed is:

1. An isolated antibody specifically binding the C-terminus part of the MCM9 protein, said antibody being specifically directed against to the following peptide:

PWRADNVESNKKKRLALDSE as set forth in SEQ ID NO: 66, said antibody being a monoclonal antibody.

* * * * *

SEQUENCE LISTING

<160> NUMBER OF SEQ ID NOS: 76

<210> SEQ ID NO 1

```
<211> LENGTH: 4798
<212> TYPE: DNA
<213> ORGANISM: Homo sapiens
<220> FEATURE:
<221> NAME/KEY: CDS
<222> LOCATION: (1)..(3429)

<400> SEQUENCE: 1

atg aat agc gat caa gtt aca ctg gtt ggt caa gtg ttt gag tca tat       48
Met Asn Ser Asp Gln Val Thr Leu Val Gly Gln Val Phe Glu Ser Tyr
1               5                   10                  15

gtt tcg gaa tac cat aag aat gat att ctt cta atc ttg aag gaa agg       96
Val Ser Glu Tyr His Lys Asn Asp Ile Leu Leu Ile Leu Lys Glu Arg
            20                  25                  30

gat gaa gat gct cat tac cca gtt gtg gtt aat gcc atg act ctg ttt      144
Asp Glu Asp Ala His Tyr Pro Val Val Val Asn Ala Met Thr Leu Phe
        35                  40                  45

gag acc aac atg gaa atc ggg gaa tat ttc aac atg ttc ccc agt gaa      192
Glu Thr Asn Met Glu Ile Gly Glu Tyr Phe Asn Met Phe Pro Ser Glu
    50                  55                  60

gtg ctt aca att ttt gat agt gca ctg cga agg tca gcc ttg aca att      240
Val Leu Thr Ile Phe Asp Ser Ala Leu Arg Arg Ser Ala Leu Thr Ile
65                  70                  75                  80

ctc cag tcc ctt tct cag cct gag gct gtt tcc atg aaa cag aat ctt      288
Leu Gln Ser Leu Ser Gln Pro Glu Ala Val Ser Met Lys Gln Asn Leu
                85                  90                  95

cat gcc agg ata tca ggt ttg cct gtc tgt cct gag ctg gtg agg gaa      336
His Ala Arg Ile Ser Gly Leu Pro Val Cys Pro Glu Leu Val Arg Glu
            100                 105                 110

cac ata cct aaa acc aag gat gtg gga cac ttt tta tct gtc act ggg      384
His Ile Pro Lys Thr Lys Asp Val Gly His Phe Leu Ser Val Thr Gly
        115                 120                 125

aca gtg att cga aca agt ctg gtg aag gtt ctg gag ttt gag cgg gat      432
Thr Val Ile Arg Thr Ser Leu Val Lys Val Leu Glu Phe Glu Arg Asp
    130                 135                 140

tac atg tgt aac aaa tgc aag cat gtg ttt gtg atc aag gct gac ttt      480
Tyr Met Cys Asn Lys Cys Lys His Val Phe Val Ile Lys Ala Asp Phe
145                 150                 155                 160

gag cag tat tac acc ttt tgc cgg cca tcc tcg tgt ccc agc ttg gag      528
Glu Gln Tyr Tyr Thr Phe Cys Arg Pro Ser Ser Cys Pro Ser Leu Glu
                165                 170                 175

agc tgt gat tcc tct aaa ttc act tgc ctc tca ggc ttg tct tcg tct      576
Ser Cys Asp Ser Ser Lys Phe Thr Cys Leu Ser Gly Leu Ser Ser Ser
            180                 185                 190

cca acc agg tgt aga gat tac cag gaa atc aaa att cag gaa cag gtt      624
Pro Thr Arg Cys Arg Asp Tyr Gln Glu Ile Lys Ile Gln Glu Gln Val
        195                 200                 205

caa agg cta tct gtt gga agt att cca cga tct atg aag gtt att ctg      672
Gln Arg Leu Ser Val Gly Ser Ile Pro Arg Ser Met Lys Val Ile Leu
    210                 215                 220

gaa gat gac tta gtg gat agt tgc aaa tct ggt gat gac ctc act att      720
Glu Asp Asp Leu Val Asp Ser Cys Lys Ser Gly Asp Asp Leu Thr Ile
225                 230                 235                 240

tac ggg att gta atg caa cgg tgg aag ccc ttt cag caa gat gtg cgc      768
Tyr Gly Ile Val Met Gln Arg Trp Lys Pro Phe Gln Gln Asp Val Arg
                245                 250                 255

tgt gaa gtg gag ata gtc ctg aaa gca aat tac atc caa gta aat aat      816
Cys Glu Val Glu Ile Val Leu Lys Ala Asn Tyr Ile Gln Val Asn Asn
            260                 265                 270

gag cag tcc tca ggg atc atc atg gat gag gag gtc caa aag gaa ttc      864
Glu Gln Ser Ser Gly Ile Ile Met Asp Glu Glu Val Gln Lys Glu Phe
```

-continued

```
        275                 280                 285

gaa gat ttt tgg gaa tac tat aag agc gat ccc ttt gca gga agg aat      912
Glu Asp Phe Trp Glu Tyr Tyr Lys Ser Asp Pro Phe Ala Gly Arg Asn
    290                 295                 300

gta ata ttg gct agc ttg tgc cct caa gtg ttt gga atg tat cta gta      960
Val Ile Leu Ala Ser Leu Cys Pro Gln Val Phe Gly Met Tyr Leu Val
305                 310                 315                 320

aag ctt gct gtg gcc atg gtg ctg gct ggt ggg att caa agg act gat     1008
Lys Leu Ala Val Ala Met Val Leu Ala Gly Gly Ile Gln Arg Thr Asp
                325                 330                 335

gct aca gga aca cgg gtc aga gga gaa tct cat ctt tta ttg gtt ggg     1056
Ala Thr Gly Thr Arg Val Arg Gly Glu Ser His Leu Leu Leu Val Gly
            340                 345                 350

gat cct ggc aca ggg aaa tct cag ttc ctc aaa tat gca gca aag att     1104
Asp Pro Gly Thr Gly Lys Ser Gln Phe Leu Lys Tyr Ala Ala Lys Ile
        355                 360                 365

aca cca aga tct gtg ctg acc aca gga att gga tct act agt gca ggt     1152
Thr Pro Arg Ser Val Leu Thr Thr Gly Ile Gly Ser Thr Ser Ala Gly
    370                 375                 380

ctg acg gta act gct gta aaa gac tca gga gaa tgg aat ttg gag gct     1200
Leu Thr Val Thr Ala Val Lys Asp Ser Gly Glu Trp Asn Leu Glu Ala
385                 390                 395                 400

ggg gca tta gtt ctt gca gat gcg ggc ctt tgc tgt att gat gag ttc     1248
Gly Ala Leu Val Leu Ala Asp Ala Gly Leu Cys Cys Ile Asp Glu Phe
                405                 410                 415

aat agc ctc aaa gag cat gat agg acc agt atc cat gaa gca atg gag     1296
Asn Ser Leu Lys Glu His Asp Arg Thr Ser Ile His Glu Ala Met Glu
            420                 425                 430

caa caa acc ata agt gtt gct aag gct ggc ctc gtg tgc aag ctg aac     1344
Gln Gln Thr Ile Ser Val Ala Lys Ala Gly Leu Val Cys Lys Leu Asn
        435                 440                 445

aca agg acc acc atc ctg gca gca acg aac ccc aaa ggc cag tac gac     1392
Thr Arg Thr Thr Ile Leu Ala Ala Thr Asn Pro Lys Gly Gln Tyr Asp
    450                 455                 460

ccc cag gag tcc gtg tct gtg aac att gcc ctc ggc agc cca ctc tta     1440
Pro Gln Glu Ser Val Ser Val Asn Ile Ala Leu Gly Ser Pro Leu Leu
465                 470                 475                 480

agt cga ttt gac ctg atc ctg gtt ttg ctt gat acc aag aat gaa gac     1488
Ser Arg Phe Asp Leu Ile Leu Val Leu Leu Asp Thr Lys Asn Glu Asp
                485                 490                 495

tgg gat cgt atc att tcc tcc ttt atc tta gaa aat aaa ggt tac cca     1536
Trp Asp Arg Ile Ile Ser Ser Phe Ile Leu Glu Asn Lys Gly Tyr Pro
            500                 505                 510

agc aaa tca gag aag ctc tgg agc atg gaa aag atg aaa acc tat ttc     1584
Ser Lys Ser Glu Lys Leu Trp Ser Met Glu Lys Met Lys Thr Tyr Phe
        515                 520                 525

tgc ctc ata agg aat ctg cag ccc aca ctg tct gat gtg ggc aat cag     1632
Cys Leu Ile Arg Asn Leu Gln Pro Thr Leu Ser Asp Val Gly Asn Gln
    530                 535                 540

gtt ctt ctc cgg tac tac cag atg caa agg cag agt gat tgc cgg aac     1680
Val Leu Leu Arg Tyr Tyr Gln Met Gln Arg Gln Ser Asp Cys Arg Asn
545                 550                 555                 560

gct gcc cgg acc acc att cgg ctg ttg gaa agc ttg ata cga tta gca     1728
Ala Ala Arg Thr Thr Ile Arg Leu Leu Glu Ser Leu Ile Arg Leu Ala
                565                 570                 575

gaa gct cat gct cgc ctg atg ttt cgt gat act gta act ctg gaa gac     1776
Glu Ala His Ala Arg Leu Met Phe Arg Asp Thr Val Thr Leu Glu Asp
            580                 585                 590

gct att acg gtg gtg tca gtc atg gag tcc tca atg cag gga ggt gca     1824
```

-continued

```
Ala Ile Thr Val Val Ser Val Met Glu Ser Ser Met Gln Gly Gly Ala
        595                 600                 605

ctg cta gga ggt gtg aat gcc ctc cac act tcc ttt cct gaa aac cct      1872
Leu Leu Gly Gly Val Asn Ala Leu His Thr Ser Phe Pro Glu Asn Pro
    610                 615                 620

gga gag cag tac cag aga cag tgt gaa ctt att ctg gaa aag cta gag      1920
Gly Glu Gln Tyr Gln Arg Gln Cys Glu Leu Ile Leu Glu Lys Leu Glu
625                 630                 635                 640

ctg cag agc ctc ttg agt gaa gag ctt aga aga ctt gaa agg tta cag      1968
Leu Gln Ser Leu Leu Ser Glu Glu Leu Arg Arg Leu Glu Arg Leu Gln
                645                 650                 655

aat cag agt gtg cac caa tcc caa cca cgg gta ttg gag gta gag act      2016
Asn Gln Ser Val His Gln Ser Gln Pro Arg Val Leu Glu Val Glu Thr
            660                 665                 670

act cca gga tcc ttg aga aat ggt cca ggg gaa gaa tca aac ttc aga      2064
Thr Pro Gly Ser Leu Arg Asn Gly Pro Gly Glu Glu Ser Asn Phe Arg
        675                 680                 685

act tca tca cag cag gaa atc aac tat agc aca cat atc ttc tct cct      2112
Thr Ser Ser Gln Gln Glu Ile Asn Tyr Ser Thr His Ile Phe Ser Pro
    690                 695                 700

gga ggc agc ccc gag gga agc cca gtt cta gat ccc cca ccg cat ctg      2160
Gly Gly Ser Pro Glu Gly Ser Pro Val Leu Asp Pro Pro Pro His Leu
705                 710                 715                 720

gag cct aat aga tca aca agt agg aaa cat tca gct cag cac aaa aat      2208
Glu Pro Asn Arg Ser Thr Ser Arg Lys His Ser Ala Gln His Lys Asn
                725                 730                 735

aac aga gat gac agt tta gat tgg ttt gat ttc atg gca act cat cag      2256
Asn Arg Asp Asp Ser Leu Asp Trp Phe Asp Phe Met Ala Thr His Gln
            740                 745                 750

agt gaa cct aaa aac act gtt gtt gtg tct cct cat ccc aaa aca tct      2304
Ser Glu Pro Lys Asn Thr Val Val Val Ser Pro His Pro Lys Thr Ser
        755                 760                 765

gga gaa aat atg gct tcg aag atc tct aac agc aca tct cag ggt aag      2352
Gly Glu Asn Met Ala Ser Lys Ile Ser Asn Ser Thr Ser Gln Gly Lys
    770                 775                 780

gag aag agt gag cca ggc caa agg agc aaa gtg gac att ggg ttg ctt      2400
Glu Lys Ser Glu Pro Gly Gln Arg Ser Lys Val Asp Ile Gly Leu Leu
785                 790                 795                 800

cca tca cca gga gag aca ggt gtt cca tgg agg gca gac aat gtg gaa      2448
Pro Ser Pro Gly Glu Thr Gly Val Pro Trp Arg Ala Asp Asn Val Glu
                805                 810                 815

agt aac aag aaa aaa agg cta gca cta gat tct gaa gca gca gtc tct      2496
Ser Asn Lys Lys Lys Arg Leu Ala Leu Asp Ser Glu Ala Ala Val Ser
            820                 825                 830

gct gat aaa cca gac tca gta ctg act cat cat gtc ccc agg aac ctg      2544
Ala Asp Lys Pro Asp Ser Val Leu Thr His His Val Pro Arg Asn Leu
        835                 840                 845

cag aag ctg tgc aaa gag agg gcc cag aag ttg tgc aga aat agc acc      2592
Gln Lys Leu Cys Lys Glu Arg Ala Gln Lys Leu Cys Arg Asn Ser Thr
    850                 855                 860

agg gtg cct gca cag tgc aca gtc cct tcc cat cct cag tcc act cct      2640
Arg Val Pro Ala Gln Cys Thr Val Pro Ser His Pro Gln Ser Thr Pro
865                 870                 875                 880

gta cat agc cca gac aga agg ctg gac tca ccc aaa aga aag aga ccg      2688
Val His Ser Pro Asp Arg Arg Leu Asp Ser Pro Lys Arg Lys Arg Pro
                885                 890                 895

aaa tcc ctt gcg caa gtg gaa gag cct gca att gaa aat gtt aag cct      2736
Lys Ser Leu Ala Gln Val Glu Glu Pro Ala Ile Glu Asn Val Lys Pro
            900                 905                 910
```

```
cca ggt tcc cct gtg gcc aaa ctg gca aaa ttt act ttc aag cag aag     2784
Pro Gly Ser Pro Val Ala Lys Leu Ala Lys Phe Thr Phe Lys Gln Lys
        915                 920                 925

tca aaa ctg atc cac tcc ttt gaa gat cac agc cat gtg tca cct ggt     2832
Ser Lys Leu Ile His Ser Phe Glu Asp His Ser His Val Ser Pro Gly
    930                 935                 940

gca act aaa ata gca gtt cat agt cct aaa att tcc cag cgt aga aca     2880
Ala Thr Lys Ile Ala Val His Ser Pro Lys Ile Ser Gln Arg Arg Thr
945                 950                 955                 960

aga aga gac gca gcc ttg ccg gtg aag cgt cca gga aag tta aca tct     2928
Arg Arg Asp Ala Ala Leu Pro Val Lys Arg Pro Gly Lys Leu Thr Ser
                965                 970                 975

acc cca gga aac cag atc tcc agt cag cca cag ggt gag aca aag gag     2976
Thr Pro Gly Asn Gln Ile Ser Ser Gln Pro Gln Gly Glu Thr Lys Glu
            980                 985                 990

gtg tcg cag cag cca cca gag aaa  cac gga cca aga gag  aag gtg atg   3024
Val Ser Gln Gln Pro Pro Glu Lys  His Gly Pro Arg Glu  Lys Val Met
        995                 1000                 1005

tgt gcc  cct gag aag agg att  att cag cct gaa tta  gag ctt ggg      3069
Cys Ala  Pro Glu Lys Arg Ile  Ile Gln Pro Glu Leu  Glu Leu Gly
    1010                 1015                 1020

aac gag  act ggg tgt gct cat  ctt act tgt gag gga  gac aaa aag      3114
Asn Glu  Thr Gly Cys Ala His  Leu Thr Cys Glu Gly  Asp Lys Lys
    1025                 1030                 1035

gaa gag  gtt tca ggc agt aat  aaa agc ggc aag gtt  cat gcc tgc      3159
Glu Glu  Val Ser Gly Ser Asn  Lys Ser Gly Lys Val  His Ala Cys
    1040                 1045                 1050

aca tta  gcc aga ttg gca aac  ttc tgc ttt act ccc  cca tcg gaa      3204
Thr Leu  Ala Arg Leu Ala Asn  Phe Cys Phe Thr Pro  Pro Ser Glu
    1055                 1060                 1065

tcc aaa  tca aaa tcc cct cct  cct gaa agg aag aac  cga ggt gag      3249
Ser Lys  Ser Lys Ser Pro Pro  Pro Glu Arg Lys Asn  Arg Gly Glu
    1070                 1075                 1080

aga ggc  cca agc tcc cct cct  aca acc aca gct cca  atg cgt gtc      3294
Arg Gly  Pro Ser Ser Pro Pro  Thr Thr Thr Ala Pro  Met Arg Val
    1085                 1090                 1095

agt aaa  agg aaa tct ttt cag  ctc cgt ggg tcc acc  gag aaa ctg      3339
Ser Lys  Arg Lys Ser Phe Gln  Leu Arg Gly Ser Thr  Glu Lys Leu
    1100                 1105                 1110

att gtt  tcc aaa gaa tcc ctc  ttc act tta cca gaa  cta ggt gat      3384
Ile Val  Ser Lys Glu Ser Leu  Phe Thr Leu Pro Glu  Leu Gly Asp
    1115                 1120                 1125

gaa gca  ttt gat tgt gac tgg  gat gaa gag atg aga  aaa aag tca      3429
Glu Ala  Phe Asp Cys Asp Trp  Asp Glu Glu Met Arg  Lys Lys Ser
    1130                 1135                 1140

tagttgggaa aagctttctg gtcaaatctc accttcttca actccacaga ggaccttcag   3489

gatatcaata tggtatttat aaatgtatag aacaattggc catattgagg atcactctga   3549

atactggctc ccccttaagg ctttctaatt tcaggttaat cttcatgact taaaaagttg   3609

tataatcagt tgaggtcagt gtgataccag cagctgagct gaattaatta tgttgtgctt   3669

aattttacaa atggagtact tgtattcctg ttcctgaagc tgtttctgtt ttttgttttg   3729

ttttgttttt aagggggaga ggttcttccc tagattaatt tcttctttca ttcactcagg   3789

aacaaatgtc aagaaggtag cactcataaa tctaacaagg cagatgaact cttttctact   3849

ttttttttt ttttttgtat tttcacctgg aatgggctaa gtacagtgaa tataatcact    3909

tggatgattt gccaaaatca gactattttt ctagtattat ttttgtattg atttgtgtgg   3969

atcaggttaa atgtgactaa tgcttttctt tctttgagag gtatccttac aattccatga   4029
```

```
tgttcttaga gatctggcca ctggtcaaac agtacctttc tgaagtactg accttctgag   4089

ttgtcctttc tttcttgagc caacattttg tacttcagat tctttttttct cttgggggcc   4149

taccttcaac caagtaaaat actgtgatta gaagaagaga gagtatgagc caggcacagt   4209

gactcactcc tgtagtccta gctactcggg gaggctgagg caggatgatt gcttaagccc   4269

aggagttcgg ggttacagtg agctgtggtc acaccactgt attccagcct gggtgacaga   4329

gtgagatcct gtctctaaaa ataaaataaa tgaagaagag agactatgtg gtagtctcaa   4389

tcaaacatca tgtctcatct acccagctgg ttaatatgga aatgtgattc ctactaagtt   4449

gtgattcact tgtctttaaa accaaggaaa ttatgtactg tttttggtca gaatagataa   4509

cctcaagctt tgtctttcta tgtgctttta aaatcactta ttcctttgga ttctaataag   4569

ggttattagg attcagtaat tatggacttt ctcttctgaa gtgtgaattt gtaaactgat   4629

tgtttaattg tcagagggac ttttggacat agaatactca aaactatatg tattttgttt   4689

aattttcact tcattcaatt cacgcattga aaacaaattt agaaaatcca atttttctta   4749

agcatttaaa cgttctaaaa ttcactaata aaattttctg aaaaaattt                4798

<210> SEQ ID NO 2
<211> LENGTH: 1143
<212> TYPE: PRT
<213> ORGANISM: Homo sapiens

<400> SEQUENCE: 2

Met Asn Ser Asp Gln Val Thr Leu Val Gly Gln Val Phe Glu Ser Tyr
1               5                   10                  15

Val Ser Glu Tyr His Lys Asn Asp Ile Leu Leu Ile Leu Lys Glu Arg
            20                  25                  30

Asp Glu Asp Ala His Tyr Pro Val Val Val Asn Ala Met Thr Leu Phe
        35                  40                  45

Glu Thr Asn Met Glu Ile Gly Glu Tyr Phe Asn Met Phe Pro Ser Glu
    50                  55                  60

Val Leu Thr Ile Phe Asp Ser Ala Leu Arg Arg Ser Ala Leu Thr Ile
65                  70                  75                  80

Leu Gln Ser Leu Ser Gln Pro Glu Ala Val Ser Met Lys Gln Asn Leu
                85                  90                  95

His Ala Arg Ile Ser Gly Leu Pro Val Cys Pro Glu Leu Val Arg Glu
            100                 105                 110

His Ile Pro Lys Thr Lys Asp Val Gly His Phe Leu Ser Val Thr Gly
        115                 120                 125

Thr Val Ile Arg Thr Ser Leu Val Lys Val Leu Glu Phe Glu Arg Asp
    130                 135                 140

Tyr Met Cys Asn Lys Cys Lys His Val Phe Val Ile Lys Ala Asp Phe
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
            180                 185                 190

Pro Thr Arg Cys Arg Asp Tyr Gln Glu Ile Lys Ile Gln Glu Gln Val
        195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240
```

```
Tyr Gly Ile Val Met Gln Arg Trp Lys Pro Phe Gln Gln Asp Val Arg
                245                 250                 255

Cys Glu Val Glu Ile Val Leu Lys Ala Asn Tyr Ile Gln Val Asn Asn
            260                 265                 270

Glu Gln Ser Ser Gly Ile Ile Met Asp Glu Glu Val Gln Lys Glu Phe
        275                 280                 285

Glu Asp Phe Trp Glu Tyr Tyr Lys Ser Asp Pro Phe Ala Gly Arg Asn
    290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                325                 330                 335

Ala Thr Gly Thr Arg Val Arg Gly Glu Ser His Leu Leu Leu Val Gly
            340                 345                 350

Asp Pro Gly Thr Gly Lys Ser Gln Phe Leu Lys Tyr Ala Ala Lys Ile
        355                 360                 365

Thr Pro Arg Ser Val Leu Thr Thr Gly Ile Gly Ser Thr Ser Ala Gly
    370                 375                 380

Leu Thr Val Thr Ala Val Lys Asp Ser Gly Glu Trp Asn Leu Glu Ala
385                 390                 395                 400

Gly Ala Leu Val Leu Ala Asp Ala Gly Leu Cys Cys Ile Asp Glu Phe
                405                 410                 415

Asn Ser Leu Lys Glu His Asp Arg Thr Ser Ile His Glu Ala Met Glu
            420                 425                 430

Gln Gln Thr Ile Ser Val Ala Lys Ala Gly Leu Val Cys Lys Leu Asn
        435                 440                 445

Thr Arg Thr Thr Ile Leu Ala Ala Thr Asn Pro Lys Gly Gln Tyr Asp
    450                 455                 460

Pro Gln Glu Ser Val Ser Val Asn Ile Ala Leu Gly Ser Pro Leu Leu
465                 470                 475                 480

Ser Arg Phe Asp Leu Ile Leu Val Leu Leu Asp Thr Lys Asn Glu Asp
                485                 490                 495

Trp Asp Arg Ile Ile Ser Ser Phe Ile Leu Glu Asn Lys Gly Tyr Pro
            500                 505                 510

Ser Lys Ser Glu Lys Leu Trp Ser Met Glu Lys Met Lys Thr Tyr Phe
        515                 520                 525

Cys Leu Ile Arg Asn Leu Gln Pro Thr Leu Ser Asp Val Gly Asn Gln
    530                 535                 540

Val Leu Leu Arg Tyr Tyr Gln Met Gln Arg Gln Ser Asp Cys Arg Asn
545                 550                 555                 560

Ala Ala Arg Thr Thr Ile Arg Leu Leu Glu Ser Leu Ile Arg Leu Ala
                565                 570                 575

Glu Ala His Ala Arg Leu Met Phe Arg Asp Thr Val Thr Leu Glu Asp
            580                 585                 590

Ala Ile Thr Val Val Ser Val Met Glu Ser Ser Met Gln Gly Gly Ala
        595                 600                 605

Leu Leu Gly Gly Val Asn Ala Leu His Thr Ser Phe Pro Glu Asn Pro
    610                 615                 620

Gly Glu Gln Tyr Gln Arg Gln Cys Glu Leu Ile Leu Glu Lys Leu Glu
625                 630                 635                 640

Leu Gln Ser Leu Leu Ser Glu Glu Leu Arg Arg Leu Glu Arg Leu Gln
                645                 650                 655
```

```
Asn Gln Ser Val His Gln Ser Gln Pro Arg Val Leu Glu Val Glu Thr
            660                 665                 670

Thr Pro Gly Ser Leu Arg Asn Gly Pro Gly Glu Glu Ser Asn Phe Arg
        675                 680                 685

Thr Ser Ser Gln Gln Glu Ile Asn Tyr Ser Thr His Ile Phe Ser Pro
    690                 695                 700

Gly Gly Ser Pro Glu Gly Ser Pro Val Leu Asp Pro Pro Pro His Leu
705                 710                 715                 720

Glu Pro Asn Arg Ser Thr Ser Arg Lys His Ser Ala Gln His Lys Asn
                725                 730                 735

Asn Arg Asp Asp Ser Leu Asp Trp Phe Asp Phe Met Ala Thr His Gln
            740                 745                 750

Ser Glu Pro Lys Asn Thr Val Val Val Ser Pro His Pro Lys Thr Ser
        755                 760                 765

Gly Glu Asn Met Ala Ser Lys Ile Ser Asn Ser Thr Ser Gln Gly Lys
    770                 775                 780

Glu Lys Ser Glu Pro Gly Gln Arg Ser Lys Val Asp Ile Gly Leu Leu
785                 790                 795                 800

Pro Ser Pro Gly Glu Thr Gly Val Pro Trp Arg Ala Asp Asn Val Glu
                805                 810                 815

Ser Asn Lys Lys Lys Arg Leu Ala Leu Asp Ser Glu Ala Ala Val Ser
            820                 825                 830

Ala Asp Lys Pro Asp Ser Val Leu Thr His His Val Pro Arg Asn Leu
        835                 840                 845

Gln Lys Leu Cys Lys Glu Arg Ala Gln Lys Leu Cys Arg Asn Ser Thr
    850                 855                 860

Arg Val Pro Ala Gln Cys Thr Val Pro Ser His Pro Gln Ser Thr Pro
865                 870                 875                 880

Val His Ser Pro Asp Arg Arg Leu Asp Ser Pro Lys Arg Lys Arg Pro
                885                 890                 895

Lys Ser Leu Ala Gln Val Glu Glu Pro Ala Ile Glu Asn Val Lys Pro
            900                 905                 910

Pro Gly Ser Pro Val Ala Lys Leu Ala Lys Phe Thr Phe Lys Gln Lys
        915                 920                 925

Ser Lys Leu Ile His Ser Phe Glu Asp His Ser His Val Ser Pro Gly
    930                 935                 940

Ala Thr Lys Ile Ala Val His Ser Pro Lys Ile Ser Gln Arg Arg Thr
945                 950                 955                 960

Arg Arg Asp Ala Ala Leu Pro Val Lys Arg Pro Gly Lys Leu Thr Ser
                965                 970                 975

Thr Pro Gly Asn Gln Ile Ser Ser Gln Pro Gln Gly Glu Thr Lys Glu
            980                 985                 990

Val Ser Gln Gln Pro Pro Glu Lys  His Gly Pro Arg Glu  Lys Val Met
        995                 1000                 1005

Cys Ala  Pro Glu Lys Arg Ile  Ile Gln Pro Glu Leu  Glu Leu Gly
    1010                 1015                 1020

Asn Glu  Thr Gly Cys Ala His  Leu Thr Cys Glu Gly  Asp Lys Lys
    1025                 1030                 1035

Glu Glu  Val Ser Gly Ser Asn  Lys Ser Gly Lys Val  His Ala Cys
    1040                 1045                 1050

Thr Leu  Ala Arg Leu Ala Asn  Phe Cys Phe Thr Pro  Pro Ser Glu
    1055                 1060                 1065

Ser Lys  Ser Lys Ser Pro Pro  Pro Glu Arg Lys Asn  Arg Gly Glu
```

```
    1070                1075                1080

Arg Gly  Pro Ser Ser Pro Pro  Thr Thr Thr Ala Pro  Met Arg Val
    1085                1090                1095

Ser Lys  Arg Lys Ser Phe Gln  Leu Arg Gly Ser Thr  Glu Lys Leu
    1100                1105                1110

Ile Val  Ser Lys Glu Ser Leu  Phe Thr Leu Pro Glu  Leu Gly Asp
    1115                1120                1125

Glu Ala  Phe Asp Cys Asp Trp  Asp Glu Glu Met Arg  Lys Lys Ser
    1130                1135                1140


<210> SEQ ID NO 3
<211> LENGTH: 3646
<212> TYPE: DNA
<213> ORGANISM: Homo sapiens
<220> FEATURE:
<221> NAME/KEY: CDS
<222> LOCATION: (1)..(2277)

<400> SEQUENCE: 3

ctg acg gta act gct gta aaa gac tca gga gaa tgg aat ttg gag gct       48
Leu Thr Val Thr Ala Val Lys Asp Ser Gly Glu Trp Asn Leu Glu Ala
1               5                   10                  15

ggg gca tta gtt ctt gca gat gcg ggc ctt tgc tgt att gat gag ttc       96
Gly Ala Leu Val Leu Ala Asp Ala Gly Leu Cys Cys Ile Asp Glu Phe
            20                  25                  30

aat agc ctc aaa gag cat gat agg acc agt atc cat gaa gca atg gag      144
Asn Ser Leu Lys Glu His Asp Arg Thr Ser Ile His Glu Ala Met Glu
        35                  40                  45

caa caa acc ata agt gtt gct aag gct ggc ctc gtg tgc aag ctg aac      192
Gln Gln Thr Ile Ser Val Ala Lys Ala Gly Leu Val Cys Lys Leu Asn
    50                  55                  60

aca agg acc acc atc ctg gca gca acg aac ccc aaa ggc cag tac gac      240
Thr Arg Thr Thr Ile Leu Ala Ala Thr Asn Pro Lys Gly Gln Tyr Asp
65                  70                  75                  80

ccc cag gag tcc gtg tct gtg aac att gcc ctc ggc agc cca ctc tta      288
Pro Gln Glu Ser Val Ser Val Asn Ile Ala Leu Gly Ser Pro Leu Leu
                85                  90                  95

agt cga ttt gac ctg atc ctg gtt ttg ctt gat acc aag aat gaa gac      336
Ser Arg Phe Asp Leu Ile Leu Val Leu Leu Asp Thr Lys Asn Glu Asp
            100                 105                 110

tgg gat cgt atc att tcc tcc ttt atc tta gaa aat aaa ggt tac cca      384
Trp Asp Arg Ile Ile Ser Ser Phe Ile Leu Glu Asn Lys Gly Tyr Pro
        115                 120                 125

agc aaa tca gag aag ctc tgg agc atg gaa aag atg aaa acc tat ttc      432
Ser Lys Ser Glu Lys Leu Trp Ser Met Glu Lys Met Lys Thr Tyr Phe
    130                 135                 140

tgc ctc ata agg aat ctg cag ccc aca ctg tct gat gtg ggc aat cag      480
Cys Leu Ile Arg Asn Leu Gln Pro Thr Leu Ser Asp Val Gly Asn Gln
145                 150                 155                 160

gtt ctt ctc cgg tac tac cag atg caa agg cag agt gat tgc cgg aac      528
Val Leu Leu Arg Tyr Tyr Gln Met Gln Arg Gln Ser Asp Cys Arg Asn
                165                 170                 175

gct gcc cgg acc acc att cgg ctg ttg gaa agc ttg ata cga tta gca      576
Ala Ala Arg Thr Thr Ile Arg Leu Leu Glu Ser Leu Ile Arg Leu Ala
            180                 185                 190

gaa gct cat gct cgc ctg atg ttt cgt gat act gta act ctg gaa gac      624
Glu Ala His Ala Arg Leu Met Phe Arg Asp Thr Val Thr Leu Glu Asp
        195                 200                 205

gct att acg gtg gtg tca gtc atg gag tcc tca atg cag gga ggt gca      672
Ala Ile Thr Val Val Ser Val Met Glu Ser Ser Met Gln Gly Gly Ala
```

```
    210                 215                 220

ctg cta gga ggt gtg aat gcc ctc cac act tcc ttt cct gaa aac cct      720
Leu Leu Gly Gly Val Asn Ala Leu His Thr Ser Phe Pro Glu Asn Pro
225                 230                 235                 240

gga gag cag tac cag aga cag tgt gaa ctt att ctg gaa aag cta gag      768
Gly Glu Gln Tyr Gln Arg Gln Cys Glu Leu Ile Leu Glu Lys Leu Glu
                245                 250                 255

ctg cag agc ctc ttg agt gaa gag ctt aga aga ctt gaa agg tta cag      816
Leu Gln Ser Leu Leu Ser Glu Glu Leu Arg Arg Leu Glu Arg Leu Gln
            260                 265                 270

aat cag agt gtg cac caa tcc caa cca cgg gta ttg gag gta gag act      864
Asn Gln Ser Val His Gln Ser Gln Pro Arg Val Leu Glu Val Glu Thr
        275                 280                 285

act cca gga tcc ttg aga aat ggt cca ggg gaa gaa tca aac ttc aga      912
Thr Pro Gly Ser Leu Arg Asn Gly Pro Gly Glu Glu Ser Asn Phe Arg
    290                 295                 300

act tca tca cag cag gaa atc aac tat agc aca cat atc ttc tct cct      960
Thr Ser Ser Gln Gln Glu Ile Asn Tyr Ser Thr His Ile Phe Ser Pro
305                 310                 315                 320

gga ggc agc ccc gag gga agc cca gtt cta gat ccc cca ccg cat ctg     1008
Gly Gly Ser Pro Glu Gly Ser Pro Val Leu Asp Pro Pro Pro His Leu
                325                 330                 335

gag cct aat aga tca aca agt agg aaa cat tca gct cag cac aaa aat     1056
Glu Pro Asn Arg Ser Thr Ser Arg Lys His Ser Ala Gln His Lys Asn
            340                 345                 350

aac aga gat gac agt tta gat tgg ttt gat ttc atg gca act cat cag     1104
Asn Arg Asp Asp Ser Leu Asp Trp Phe Asp Phe Met Ala Thr His Gln
        355                 360                 365

agt gaa cct aaa aac act gtt gtt gtg tct cct cat ccc aaa aca tct     1152
Ser Glu Pro Lys Asn Thr Val Val Val Ser Pro His Pro Lys Thr Ser
    370                 375                 380

gga gaa aat atg gct tcg aag atc tct aac agc aca tct cag ggt aag     1200
Gly Glu Asn Met Ala Ser Lys Ile Ser Asn Ser Thr Ser Gln Gly Lys
385                 390                 395                 400

gag aag agt gag cca ggc caa agg agc aaa gtg gac att ggg ttg ctt     1248
Glu Lys Ser Glu Pro Gly Gln Arg Ser Lys Val Asp Ile Gly Leu Leu
                405                 410                 415

cca tca cca gga gag aca ggt gtt cca tgg agg gca gac aat gtg gaa     1296
Pro Ser Pro Gly Glu Thr Gly Val Pro Trp Arg Ala Asp Asn Val Glu
            420                 425                 430

agt aac aag aaa aaa agg cta gca cta gat tct gaa gca gca gtc tct     1344
Ser Asn Lys Lys Lys Arg Leu Ala Leu Asp Ser Glu Ala Ala Val Ser
        435                 440                 445

gct gat aaa cca gac tca gta ctg act cat cat gtc ccc agg aac ctg     1392
Ala Asp Lys Pro Asp Ser Val Leu Thr His His Val Pro Arg Asn Leu
    450                 455                 460

cag aag ctg tgc aaa gag agg gcc cag aag ttg tgc aga aat agc acc     1440
Gln Lys Leu Cys Lys Glu Arg Ala Gln Lys Leu Cys Arg Asn Ser Thr
465                 470                 475                 480

agg gtg cct gca cag tgc aca gtc cct tcc cat cct cag tcc act cct     1488
Arg Val Pro Ala Gln Cys Thr Val Pro Ser His Pro Gln Ser Thr Pro
                485                 490                 495

gta cat agc cca gac aga agg ctg gac tca ccc aaa aga aag aga ccg     1536
Val His Ser Pro Asp Arg Arg Leu Asp Ser Pro Lys Arg Lys Arg Pro
            500                 505                 510

aaa tcc ctt gcg caa gtg gaa gag cct gca att gaa aat gtt aag cct     1584
Lys Ser Leu Ala Gln Val Glu Glu Pro Ala Ile Glu Asn Val Lys Pro
        515                 520                 525

cca ggt tcc cct gtg gcc aaa ctg gca aaa ttt act ttc aag cag aag     1632
```

-continued

```
Pro Gly Ser Pro Val Ala Lys Leu Ala Lys Phe Thr Phe Lys Gln Lys
    530                 535                 540

tca aaa ctg atc cac tcc ttt gaa gat cac agc cat gtg tca cct ggt     1680
Ser Lys Leu Ile His Ser Phe Glu Asp His Ser His Val Ser Pro Gly
545                 550                 555                 560

gca act aaa ata gca gtt cat agt cct aaa att tcc cag cgt aga aca     1728
Ala Thr Lys Ile Ala Val His Ser Pro Lys Ile Ser Gln Arg Arg Thr
                565                 570                 575

aga aga gac gca gcc ttg ccg gtg aag cgt cca gga aag tta aca tct     1776
Arg Arg Asp Ala Ala Leu Pro Val Lys Arg Pro Gly Lys Leu Thr Ser
            580                 585                 590

acc cca gga aac cag atc tcc agt cag cca cag ggt gag aca aag gag     1824
Thr Pro Gly Asn Gln Ile Ser Ser Gln Pro Gln Gly Glu Thr Lys Glu
        595                 600                 605

gtg tcg cag cag cca cca gag aaa cac gga cca aga gag aag gtg atg     1872
Val Ser Gln Gln Pro Pro Glu Lys His Gly Pro Arg Glu Lys Val Met
    610                 615                 620

tgt gcc cct gag aag agg att att cag cct gaa tta gag ctt ggg aac     1920
Cys Ala Pro Glu Lys Arg Ile Ile Gln Pro Glu Leu Glu Leu Gly Asn
625                 630                 635                 640

gag act ggg tgt gct cat ctt act tgt gag gga gac aaa aag gaa gag     1968
Glu Thr Gly Cys Ala His Leu Thr Cys Glu Gly Asp Lys Lys Glu Glu
                645                 650                 655

gtt tca ggc agt aat aaa agc ggc aag gtt cat gcc tgc aca tta gcc     2016
Val Ser Gly Ser Asn Lys Ser Gly Lys Val His Ala Cys Thr Leu Ala
            660                 665                 670

aga ttg gca aac ttc tgc ttt act ccc cca tcg gaa tcc aaa tca aaa     2064
Arg Leu Ala Asn Phe Cys Phe Thr Pro Pro Ser Glu Ser Lys Ser Lys
        675                 680                 685

tcc cct cct cct gaa agg aag aac cga ggt gag aga ggc cca agc tcc     2112
Ser Pro Pro Pro Glu Arg Lys Asn Arg Gly Glu Arg Gly Pro Ser Ser
    690                 695                 700

cct cct aca acc aca gct cca atg cgt gtc agt aaa agg aaa tct ttt     2160
Pro Pro Thr Thr Thr Ala Pro Met Arg Val Ser Lys Arg Lys Ser Phe
705                 710                 715                 720

cag ctc cgt ggg tcc acc gag aaa ctg att gtt tcc aaa gaa tcc ctc     2208
Gln Leu Arg Gly Ser Thr Glu Lys Leu Ile Val Ser Lys Glu Ser Leu
                725                 730                 735

ttc act tta cca gaa cta ggt gat gaa gca ttt gat tgt gac tgg gat     2256
Phe Thr Leu Pro Glu Leu Gly Asp Glu Ala Phe Asp Cys Asp Trp Asp
            740                 745                 750

gaa gag atg aga aaa aag tca tagttgggaa aagctttctg gtcaaatctc        2307
Glu Glu Met Arg Lys Lys Ser
        755

accttcttca actccacaga ggaccttcag gatatcaata tggtatttat aaatgtatag   2367

aacaattggc catattgagg atcactctga atactggctc ccccttaagg ctttctaatt   2427

tcaggttaat cttcatgact taaaaagttg tataatcagt tgaggtcagt gtgataccag   2487

cagctgagct gaattaatta tgttgtgctt aattttacaa atggagtact tgtattcctg   2547

ttcctgaagc tgtttctgtt ttttgttttg ttttgttttt aagggggaga ggttcttccc   2607

tagattaatt tcttctttca ttcactcagg aacaaatgtc aagaaggtag cactcataaa   2667

tctaacaagg cagatgaact cttttctact tttttttttt ttttttgtat tttcacctgg   2727

aatgggctaa gtacagtgaa tataatcact tggatgattt gccaaaatca gactattttt   2787

ctagtattat ttttgtattg atttgtgtgg atcaggttaa atgtgactaa tgcttttctt   2847

tctttgagag gtatccttac aattccatga tgttcttaga gatctggcca ctggtcaaac   2907
```

```
agtacctttc tgaagtactg accttctgag ttgtcctttc tttcttgagc caacattttg   2967

tacttcagat tctttttttct cttgggggcc taccttcaac caagtaaaat actgtgatta  3027

gaagaagaga gagtatgagc caggcacagt gactcactcc tgtagtccta gctactcggg   3087

gaggctgagg caggatgatt gcttaagccc aggagttcgg ggttacagtg agctgtggtc   3147

acaccactgt attccagcct gggtgacaga gtgagatcct gtctctaaaa ataaaataaa   3207

tgaagaagag agactatgtg gtagtctcaa tcaaacatca tgtctcatct acccagctgg   3267

ttaatatgga aatgtgattc ctactaagtt gtgattcact tgtctttaaa accaaggaaa   3327

ttatgtactg tttttggtca gaatagataa cctcaagctt tgtctttcta tgtgctttta   3387

aaatcactta ttcctttgga ttctaataag ggttattagg attcagtaat tatggacttt   3447

ctcttctgaa gtgtgaattt gtaaactgat tgtttaattg tcagagggac ttttggacat   3507

agaatactca aaactatatg tattttgttt aattttcact tcattcaatt cacgcattga   3567

aaacaaattt agaaaatcca atttttctta agcatttaaa cgttctaaaa ttcactaata   3627

aaattttctg aaaaaattt                                                3646
```

```
<210> SEQ ID NO 4
<211> LENGTH: 759
<212> TYPE: PRT
<213> ORGANISM: Homo sapiens

<400> SEQUENCE: 4

Leu Thr Val Thr Ala Val Lys Asp Ser Gly Glu Trp Asn Leu Glu Ala
1               5                   10                  15

Gly Ala Leu Val Leu Ala Asp Ala Gly Leu Cys Cys Ile Asp Glu Phe
            20                  25                  30

Asn Ser Leu Lys Glu His Asp Arg Thr Ser Ile His Glu Ala Met Glu
        35                  40                  45

Gln Gln Thr Ile Ser Val Ala Lys Ala Gly Leu Val Cys Lys Leu Asn
    50                  55                  60

Thr Arg Thr Thr Ile Leu Ala Ala Thr Asn Pro Lys Gly Gln Tyr Asp
65                  70                  75                  80

Pro Gln Glu Ser Val Ser Val Asn Ile Ala Leu Gly Ser Pro Leu Leu
                85                  90                  95

Ser Arg Phe Asp Leu Ile Leu Val Leu Leu Asp Thr Lys Asn Glu Asp
            100                 105                 110

Trp Asp Arg Ile Ile Ser Ser Phe Ile Leu Glu Asn Lys Gly Tyr Pro
        115                 120                 125

Ser Lys Ser Glu Lys Leu Trp Ser Met Glu Lys Met Lys Thr Tyr Phe
    130                 135                 140

Cys Leu Ile Arg Asn Leu Gln Pro Thr Leu Ser Asp Val Gly Asn Gln
145                 150                 155                 160

Val Leu Leu Arg Tyr Tyr Gln Met Gln Arg Gln Ser Asp Cys Arg Asn
                165                 170                 175

Ala Ala Arg Thr Thr Ile Arg Leu Leu Glu Ser Leu Ile Arg Leu Ala
            180                 185                 190

Glu Ala His Ala Arg Leu Met Phe Arg Asp Thr Val Thr Leu Glu Asp
        195                 200                 205

Ala Ile Thr Val Val Ser Val Met Glu Ser Ser Met Gln Gly Gly Ala
    210                 215                 220

Leu Leu Gly Gly Val Asn Ala Leu His Thr Ser Phe Pro Glu Asn Pro
225                 230                 235                 240
```

```
Gly Glu Gln Tyr Gln Arg Gln Cys Glu Leu Ile Leu Glu Lys Leu Glu
                245                 250                 255

Leu Gln Ser Leu Leu Ser Glu Glu Leu Arg Arg Leu Glu Arg Leu Gln
            260                 265                 270

Asn Gln Ser Val His Gln Ser Gln Pro Arg Val Leu Glu Val Glu Thr
        275                 280                 285

Thr Pro Gly Ser Leu Arg Asn Gly Pro Gly Glu Glu Ser Asn Phe Arg
    290                 295                 300

Thr Ser Ser Gln Gln Glu Ile Asn Tyr Ser Thr His Ile Phe Ser Pro
305                 310                 315                 320

Gly Gly Ser Pro Glu Gly Ser Pro Val Leu Asp Pro Pro Pro His Leu
                325                 330                 335

Glu Pro Asn Arg Ser Thr Ser Arg Lys His Ser Ala Gln His Lys Asn
            340                 345                 350

Asn Arg Asp Asp Ser Leu Asp Trp Phe Asp Phe Met Ala Thr His Gln
        355                 360                 365

Ser Glu Pro Lys Asn Thr Val Val Val Ser Pro His Pro Lys Thr Ser
    370                 375                 380

Gly Glu Asn Met Ala Ser Lys Ile Ser Asn Ser Thr Ser Gln Gly Lys
385                 390                 395                 400

Glu Lys Ser Glu Pro Gly Gln Arg Ser Lys Val Asp Ile Gly Leu Leu
                405                 410                 415

Pro Ser Pro Gly Glu Thr Gly Val Pro Trp Arg Ala Asp Asn Val Glu
            420                 425                 430

Ser Asn Lys Lys Lys Arg Leu Ala Leu Asp Ser Glu Ala Ala Val Ser
        435                 440                 445

Ala Asp Lys Pro Asp Ser Val Leu Thr His His Val Pro Arg Asn Leu
    450                 455                 460

Gln Lys Leu Cys Lys Glu Arg Ala Gln Lys Leu Cys Arg Asn Ser Thr
465                 470                 475                 480

Arg Val Pro Ala Gln Cys Thr Val Pro Ser His Pro Gln Ser Thr Pro
                485                 490                 495

Val His Ser Pro Asp Arg Arg Leu Asp Ser Pro Lys Arg Lys Arg Pro
            500                 505                 510

Lys Ser Leu Ala Gln Val Glu Glu Pro Ala Ile Glu Asn Val Lys Pro
        515                 520                 525

Pro Gly Ser Pro Val Ala Lys Leu Ala Lys Phe Thr Phe Lys Gln Lys
    530                 535                 540

Ser Lys Leu Ile His Ser Phe Glu Asp His Ser His Val Ser Pro Gly
545                 550                 555                 560

Ala Thr Lys Ile Ala Val His Ser Pro Lys Ile Ser Gln Arg Arg Thr
                565                 570                 575

Arg Arg Asp Ala Ala Leu Pro Val Lys Arg Pro Gly Lys Leu Thr Ser
            580                 585                 590

Thr Pro Gly Asn Gln Ile Ser Ser Gln Pro Gln Gly Glu Thr Lys Glu
        595                 600                 605

Val Ser Gln Gln Pro Pro Glu Lys His Gly Pro Arg Glu Lys Val Met
    610                 615                 620

Cys Ala Pro Glu Lys Arg Ile Ile Gln Pro Glu Leu Glu Leu Gly Asn
625                 630                 635                 640

Glu Thr Gly Cys Ala His Leu Thr Cys Glu Gly Asp Lys Lys Glu Glu
                645                 650                 655

Val Ser Gly Ser Asn Lys Ser Gly Lys Val His Ala Cys Thr Leu Ala
```

```
            660                 665                 670

Arg Leu Ala Asn Phe Cys Phe Thr Pro Pro Ser Glu Ser Lys Ser Lys
        675                 680                 685

Ser Pro Pro Pro Glu Arg Lys Asn Arg Gly Glu Arg Gly Pro Ser Ser
    690                 695                 700

Pro Pro Thr Thr Thr Ala Pro Met Arg Val Ser Lys Arg Lys Ser Phe
705                 710                 715                 720

Gln Leu Arg Gly Ser Thr Glu Lys Leu Ile Val Ser Lys Glu Ser Leu
                725                 730                 735

Phe Thr Leu Pro Glu Leu Gly Asp Glu Ala Phe Asp Cys Asp Trp Asp
            740                 745                 750

Glu Glu Met Arg Lys Lys Ser
        755


<210> SEQ ID NO 5
<211> LENGTH: 1152
<212> TYPE: DNA
<213> ORGANISM: Homo sapiens
<220> FEATURE:
<221> NAME/KEY: CDS
<222> LOCATION: (1)..(1152)

<400> SEQUENCE: 5

atg aat agc gat caa gtt aca ctg gtt ggt caa gtg ttt gag tca tat       48
Met Asn Ser Asp Gln Val Thr Leu Val Gly Gln Val Phe Glu Ser Tyr
1               5                   10                  15

gtt tcg gaa tac cat aag aat gat att ctt cta atc ttg aag gaa agg       96
Val Ser Glu Tyr His Lys Asn Asp Ile Leu Leu Ile Leu Lys Glu Arg
            20                  25                  30

gat gaa gat gct cat tac cca gtt gtg gtt aat gcc atg act ctg ttt      144
Asp Glu Asp Ala His Tyr Pro Val Val Val Asn Ala Met Thr Leu Phe
        35                  40                  45

gag acc aac atg gaa atc ggg gaa tat ttc aac atg ttc ccc agt gaa      192
Glu Thr Asn Met Glu Ile Gly Glu Tyr Phe Asn Met Phe Pro Ser Glu
    50                  55                  60

gtg ctt aca att ttt gat agt gca ctg cga agg tca gcc ttg aca att      240
Val Leu Thr Ile Phe Asp Ser Ala Leu Arg Arg Ser Ala Leu Thr Ile
65                  70                  75                  80

ctc cag tcc ctt tct cag cct gag gct gtt tcc atg aaa cag aat ctt      288
Leu Gln Ser Leu Ser Gln Pro Glu Ala Val Ser Met Lys Gln Asn Leu
                85                  90                  95

cat gcc agg ata tca ggt ttg cct gtc tgt cct gag ctg gtg agg gaa      336
His Ala Arg Ile Ser Gly Leu Pro Val Cys Pro Glu Leu Val Arg Glu
            100                 105                 110

cac ata cct aaa acc aag gat gtg gga cac ttt tta tct gtc act ggg      384
His Ile Pro Lys Thr Lys Asp Val Gly His Phe Leu Ser Val Thr Gly
        115                 120                 125

aca gtg att cga aca agt ctg gtg aag gtt ctg gag ttt gag cgg gat      432
Thr Val Ile Arg Thr Ser Leu Val Lys Val Leu Glu Phe Glu Arg Asp
    130                 135                 140

tac atg tgt aac aaa tgc aag cat gtg ttt gtg atc aag gct gac ttt      480
Tyr Met Cys Asn Lys Cys Lys His Val Phe Val Ile Lys Ala Asp Phe
145                 150                 155                 160

gag cag tat tac acc ttt tgc cgg cca tcc tcg tgt ccc agc ttg gag      528
Glu Gln Tyr Tyr Thr Phe Cys Arg Pro Ser Ser Cys Pro Ser Leu Glu
                165                 170                 175

agc tgt gat tcc tct aaa ttc act tgc ctc tca ggc ttg tct tcg tct      576
Ser Cys Asp Ser Ser Lys Phe Thr Cys Leu Ser Gly Leu Ser Ser Ser
            180                 185                 190
```

```
cca acc agg tgt aga gat tac cag gaa atc aaa att cag gaa cag gtt      624
Pro Thr Arg Cys Arg Asp Tyr Gln Glu Ile Lys Ile Gln Glu Gln Val
        195                 200                 205

caa agg cta tct gtt gga agt att cca cga tct atg aag gtt att ctg      672
Gln Arg Leu Ser Val Gly Ser Ile Pro Arg Ser Met Lys Val Ile Leu
    210                 215                 220

gaa gat gac tta gtg gat agt tgc aaa tct ggt gat gac ctc act att      720
Glu Asp Asp Leu Val Asp Ser Cys Lys Ser Gly Asp Asp Leu Thr Ile
225                 230                 235                 240

tac ggg att gta atg caa cgg tgg aag ccc ttt cag caa gat gtg cgc      768
Tyr Gly Ile Val Met Gln Arg Trp Lys Pro Phe Gln Gln Asp Val Arg
                245                 250                 255

tgt gaa gtg gag ata gtc ctg aaa gca aat tac atc caa gta aat aat      816
Cys Glu Val Glu Ile Val Leu Lys Ala Asn Tyr Ile Gln Val Asn Asn
            260                 265                 270

gag cag tcc tca ggg atc atc atg gat gag gag gtc caa aag gaa ttc      864
Glu Gln Ser Ser Gly Ile Ile Met Asp Glu Glu Val Gln Lys Glu Phe
        275                 280                 285

gaa gat ttt tgg gaa tac tat aag agc gat ccc ttt gca gga agg aat      912
Glu Asp Phe Trp Glu Tyr Tyr Lys Ser Asp Pro Phe Ala Gly Arg Asn
    290                 295                 300

gta ata ttg gct agc ttg tgc cct caa gtg ttt gga atg tat cta gta      960
Val Ile Leu Ala Ser Leu Cys Pro Gln Val Phe Gly Met Tyr Leu Val
305                 310                 315                 320

aag ctt gct gtg gcc atg gtg ctg gct ggt ggg att caa agg act gat     1008
Lys Leu Ala Val Ala Met Val Leu Ala Gly Gly Ile Gln Arg Thr Asp
                325                 330                 335

gct aca gga aca cgg gtc aga gga gaa tct cat ctt tta ttg gtt ggg     1056
Ala Thr Gly Thr Arg Val Arg Gly Glu Ser His Leu Leu Leu Val Gly
            340                 345                 350

gat cct ggc aca ggg aaa tct cag ttc ctc aaa tat gca gca aag att     1104
Asp Pro Gly Thr Gly Lys Ser Gln Phe Leu Lys Tyr Ala Ala Lys Ile
        355                 360                 365

aca cca aga tct gtg ctg acc aca gga att gga tct act agt gca ggt     1152
Thr Pro Arg Ser Val Leu Thr Thr Gly Ile Gly Ser Thr Ser Ala Gly
    370                 375                 380


<210> SEQ ID NO 6
<211> LENGTH: 384
<212> TYPE: PRT
<213> ORGANISM: Homo sapiens

<400> SEQUENCE: 6

Met Asn Ser Asp Gln Val Thr Leu Val Gly Gln Val Phe Glu Ser Tyr
1               5                   10                  15

Val Ser Glu Tyr His Lys Asn Asp Ile Leu Leu Ile Leu Lys Glu Arg
            20                  25                  30

Asp Glu Asp Ala His Tyr Pro Val Val Val Asn Ala Met Thr Leu Phe
        35                  40                  45

Glu Thr Asn Met Glu Ile Gly Glu Tyr Phe Asn Met Phe Pro Ser Glu
    50                  55                  60

Val Leu Thr Ile Phe Asp Ser Ala Leu Arg Arg Ser Ala Leu Thr Ile
65                  70                  75                  80

Leu Gln Ser Leu Ser Gln Pro Glu Ala Val Ser Met Lys Gln Asn Leu
                85                  90                  95

His Ala Arg Ile Ser Gly Leu Pro Val Cys Pro Glu Leu Val Arg Glu
            100                 105                 110

His Ile Pro Lys Thr Lys Asp Val Gly His Phe Leu Ser Val Thr Gly
        115                 120                 125
```

```
Thr Val Ile Arg Thr Ser Leu Val Lys Val Leu Glu Phe Glu Arg Asp
    130                 135                 140

Tyr Met Cys Asn Lys Cys Lys His Val Phe Val Ile Lys Ala Asp Phe
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
            180                 185                 190

Pro Thr Arg Cys Arg Asp Tyr Gln Glu Ile Lys Ile Gln Glu Gln Val
        195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240

Tyr Gly Ile Val Met Gln Arg Trp Lys Pro Phe Gln Gln Asp Val Arg
                245                 250                 255

Cys Glu Val Glu Ile Val Leu Lys Ala Asn Tyr Ile Gln Val Asn Asn
            260                 265                 270

Glu Gln Ser Ser Gly Ile Ile Met Asp Glu Glu Val Gln Lys Glu Phe
        275                 280                 285

Glu Asp Phe Trp Glu Tyr Tyr Lys Ser Asp Pro Phe Ala Gly Arg Asn
    290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                325                 330                 335

Ala Thr Gly Thr Arg Val Arg Gly Glu Ser His Leu Leu Leu Val Gly
            340                 345                 350

Asp Pro Gly Thr Gly Lys Ser Gln Phe Leu Lys Tyr Ala Ala Lys Ile
        355                 360                 365

Thr Pro Arg Ser Val Leu Thr Thr Gly Ile Gly Ser Thr Ser Ala Gly
    370                 375                 380


<210> SEQ ID NO 7
<211> LENGTH: 3873
<212> TYPE: DNA
<213> ORGANISM: Mus musculus
<220> FEATURE:
<221> NAME/KEY: CDS
<222> LOCATION: (1)..(3870)

<400> SEQUENCE: 7

atg gat cag aga act aca cga aat gga aaa tat tgt gac gtg gaa ccg       48
Met Asp Gln Arg Thr Thr Arg Asn Gly Lys Tyr Cys Asp Val Glu Pro
1               5                   10                  15

gtg tcc cgc tca aac ccc gcc cca tgc ctc cga gac ccg ccc ctc aga       96
Val Ser Arg Ser Asn Pro Ala Pro Cys Leu Arg Asp Pro Pro Leu Arg
            20                  25                  30

cgt ctt gtc cgg ccc aaa ccc cgc ctc cag ctc ccc gag tcc cgc ctc      144
Arg Leu Val Arg Pro Lys Pro Arg Leu Gln Leu Pro Glu Ser Arg Leu
        35                  40                  45

tct ccc tgc tcc cgc ctc ccg ctc gca gac tcc agc gtc cgt cct ggc      192
Ser Pro Cys Ser Arg Leu Pro Leu Ala Asp Ser Ser Val Arg Pro Gly
    50                  55                  60

gcg cgc ccg cct gcg tcc gca ccc gga aga agc ccc agc ggc cgg aaa      240
Ala Arg Pro Pro Ala Ser Ala Pro Gly Arg Ser Pro Ser Gly Arg Lys
65                  70                  75                  80
```

-continued

```
gtt gag gca gtg cgc ggc tcg ggg tcc gcg gga agc tca agt cct tca      288
Val Glu Ala Val Arg Gly Ser Gly Ser Ala Gly Ser Ser Ser Pro Ser
            85                  90                  95

gag gcc gag cga gag cag cgc gaa gaa gcc tgc gcg ccc ccg cgc aag      336
Glu Ala Glu Arg Glu Gln Arg Glu Glu Ala Cys Ala Pro Pro Arg Lys
            100                 105                 110

gcg gcc ccc tcg agc ggc cgc gcg cac gcc ccg ccc cct cca acg ccg      384
Ala Ala Pro Ser Ser Gly Arg Ala His Ala Pro Pro Pro Pro Thr Pro
        115                 120                 125

cgc ggg tcg ggc tgg ggc gac cac ggc cgc agc gcg gtc ccg gcg acc      432
Arg Gly Ser Gly Trp Gly Asp His Gly Arg Ser Ala Val Pro Ala Thr
    130                 135                 140

aag aca gtg cgt gtt gag ccc tac cca ccc ttc aag atg aat agt gag      480
Lys Thr Val Arg Val Glu Pro Tyr Pro Pro Phe Lys Met Asn Ser Glu
145                 150                 155                 160

cag gtc acc ctg gtg ggt cag gtg ttt gag tcc tat gtt tca gag tac      528
Gln Val Thr Leu Val Gly Gln Val Phe Glu Ser Tyr Val Ser Glu Tyr
            165                 170                 175

cat aag aac gat att ctt ctg atc ctg aaa gaa aga gat gaa gat gct      576
His Lys Asn Asp Ile Leu Leu Ile Leu Lys Glu Arg Asp Glu Asp Ala
            180                 185                 190

cac tac ccg gtt gtg gtt aat gct atg agc ctt ttc gag acc aac atg      624
His Tyr Pro Val Val Val Asn Ala Met Ser Leu Phe Glu Thr Asn Met
        195                 200                 205

gaa att ggg gac tat ttc acc gtg ttc ccc aat gaa gta cta aca gtt      672
Glu Ile Gly Asp Tyr Phe Thr Val Phe Pro Asn Glu Val Leu Thr Val
    210                 215                 220

ttt gac agt gca ctt cga agg tca gcc ttg gca att ctg cag tcc ctt      720
Phe Asp Ser Ala Leu Arg Arg Ser Ala Leu Ala Ile Leu Gln Ser Leu
225                 230                 235                 240

cct gag acg gag ggg tta tcc atg aag cag aat ctt cat gcc agg ata      768
Pro Glu Thr Glu Gly Leu Ser Met Lys Gln Asn Leu His Ala Arg Ile
            245                 250                 255

tca ggt ttg cct gtt tgt cca gaa ctg gtc agg gaa cac att ccc aaa      816
Ser Gly Leu Pro Val Cys Pro Glu Leu Val Arg Glu His Ile Pro Lys
            260                 265                 270

acc aag gat gtg gga cac ttc tta tct gtc act ggg aca gtg atc cga      864
Thr Lys Asp Val Gly His Phe Leu Ser Val Thr Gly Thr Val Ile Arg
        275                 280                 285

acg agt ctg gtg aag gtc ttg gag ttc gag cgg gat tac atg tgt aac      912
Thr Ser Leu Val Lys Val Leu Glu Phe Glu Arg Asp Tyr Met Cys Asn
    290                 295                 300

aaa tgc aag cat gtg ttc atg gtg gag gca gac ttc gag cag tat tac      960
Lys Cys Lys His Val Phe Met Val Glu Ala Asp Phe Glu Gln Tyr Tyr
305                 310                 315                 320

acc ttc agt cgg cca tcg tca tgt cca agt tta gcc agc tgt gac tcc     1008
Thr Phe Ser Arg Pro Ser Ser Cys Pro Ser Leu Ala Ser Cys Asp Ser
            325                 330                 335

tca aaa ttc tct tgc ctc tca gac ttg tct tca tct cca gcc aga tgt     1056
Ser Lys Phe Ser Cys Leu Ser Asp Leu Ser Ser Ser Pro Ala Arg Cys
            340                 345                 350

cgg gat tac cag gaa atc aaa att cag gag cag gtg caa agg ctg tct     1104
Arg Asp Tyr Gln Glu Ile Lys Ile Gln Glu Gln Val Gln Arg Leu Ser
        355                 360                 365

gtt gga agt atc cca cgg tct atg aaa gtt att ctg gaa gat gac cta     1152
Val Gly Ser Ile Pro Arg Ser Met Lys Val Ile Leu Glu Asp Asp Leu
    370                 375                 380

gtt gac agt tgc aaa tct gga gat gac ctc acc atc tat ggg gtt gta     1200
Val Asp Ser Cys Lys Ser Gly Asp Asp Leu Thr Ile Tyr Gly Val Val
```

```
385                 390                 395                 400

atg caa cgg tgg aaa ccc ttt cag cga gat gta cgc tgt gaa gtt gag      1248
Met Gln Arg Trp Lys Pro Phe Gln Arg Asp Val Arg Cys Glu Val Glu
                405                 410                 415

att gtc ttg aaa gcc aac tat gtc caa gtg aat aat gag caa tcc tcg      1296
Ile Val Leu Lys Ala Asn Tyr Val Gln Val Asn Asn Glu Gln Ser Ser
            420                 425                 430

ggg atg gtc atg gat gag gac act cga aaa gaa ttt gaa gac ttc tgg      1344
Gly Met Val Met Asp Glu Asp Thr Arg Lys Glu Phe Glu Asp Phe Trp
        435                 440                 445

gaa cac tat aag agt gac ccc ttt gca ggg agg aat gaa ata ttg gcc      1392
Glu His Tyr Lys Ser Asp Pro Phe Ala Gly Arg Asn Glu Ile Leu Ala
    450                 455                 460

agc ttg tgt cct caa gtt ttt ggg atg tat cta gtg aag ctt gct gtg      1440
Ser Leu Cys Pro Gln Val Phe Gly Met Tyr Leu Val Lys Leu Ala Val
465                 470                 475                 480

gcc atg gta ctg gct ggt gga att caa aga act gat gct gca gga acc      1488
Ala Met Val Leu Ala Gly Gly Ile Gln Arg Thr Asp Ala Ala Gly Thr
                485                 490                 495

agg gtt aga ggg gaa tct cac ctt tta ttg gtt ggg gat cct ggc aca      1536
Arg Val Arg Gly Glu Ser His Leu Leu Leu Val Gly Asp Pro Gly Thr
            500                 505                 510

ggg aaa tca caa ttc ctt aaa tat gca gca aag att acc cca agg tcc      1584
Gly Lys Ser Gln Phe Leu Lys Tyr Ala Ala Lys Ile Thr Pro Arg Ser
        515                 520                 525

gtt ttg acc aca gga att gga tct act agt gca ggt ctg acc gtg aca      1632
Val Leu Thr Thr Gly Ile Gly Ser Thr Ser Ala Gly Leu Thr Val Thr
    530                 535                 540

gct gtc aaa gac tca gga gaa tgg aat cta gag gct ggg gct ttg gtg      1680
Ala Val Lys Asp Ser Gly Glu Trp Asn Leu Glu Ala Gly Ala Leu Val
545                 550                 555                 560

ctt gca gat gct ggt ctc tgc tgt att gac gaa ttt aac agc ctc aaa      1728
Leu Ala Asp Ala Gly Leu Cys Cys Ile Asp Glu Phe Asn Ser Leu Lys
                565                 570                 575

gaa cat gac agg aca agc atc cat gaa gca atg gag caa caa acc ata      1776
Glu His Asp Arg Thr Ser Ile His Glu Ala Met Glu Gln Gln Thr Ile
            580                 585                 590

agt gtt gct aag gct ggc ctt gtt tgt aag ctg aac aca agg acc acc      1824
Ser Val Ala Lys Ala Gly Leu Val Cys Lys Leu Asn Thr Arg Thr Thr
        595                 600                 605

atc ctg gca gca act aac ccc aaa ggc cag tat gac ccc aag gag tct      1872
Ile Leu Ala Ala Thr Asn Pro Lys Gly Gln Tyr Asp Pro Lys Glu Ser
    610                 615                 620

gtg tct gtg aac att gcc ctc ggg agc cca ctc tta agt cga ttt gac      1920
Val Ser Val Asn Ile Ala Leu Gly Ser Pro Leu Leu Ser Arg Phe Asp
625                 630                 635                 640

ctt gtc ctg gtt ttg ctc gac act agg aat gaa gac tgg gat cgt atc      1968
Leu Val Leu Val Leu Leu Asp Thr Arg Asn Glu Asp Trp Asp Arg Ile
                645                 650                 655

att tct tcc ttt atc tta gaa aat aaa ggt tat cca agc aaa tca gag      2016
Ile Ser Ser Phe Ile Leu Glu Asn Lys Gly Tyr Pro Ser Lys Ser Glu
            660                 665                 670

aat ctg tgg agc atg gag aag atg aaa acc tac ttc tgc ctc att cgg      2064
Asn Leu Trp Ser Met Glu Lys Met Lys Thr Tyr Phe Cys Leu Ile Arg
        675                 680                 685

aat ctc cac ccc aca ctg tct gaa gtg agc aat caa gtc ctc ctt cga      2112
Asn Leu His Pro Thr Leu Ser Glu Val Ser Asn Gln Val Leu Leu Arg
    690                 695                 700

tac tac caa atg caa agg cag agt gat tcc cgg aat gca gcc cgg aca      2160
```

```
Tyr Tyr Gln Met Gln Arg Gln Ser Asp Ser Arg Asn Ala Ala Arg Thr
705                 710                 715                 720

acc atc cgc ctg tta gaa agc ttg atc cga tta gca gaa gct cac gct      2208
Thr Ile Arg Leu Leu Glu Ser Leu Ile Arg Leu Ala Glu Ala His Ala
                725                 730                 735

cgc ctg atg ttc cgc agt gcc gtg act ctg gaa gat gcc gtt aca gct      2256
Arg Leu Met Phe Arg Ser Ala Val Thr Leu Glu Asp Ala Val Thr Ala
            740                 745                 750

gta tct gtg atg gag tct tca atg cag gga ggt gct ctg cta gga ggt      2304
Val Ser Val Met Glu Ser Ser Met Gln Gly Gly Ala Leu Leu Gly Gly
        755                 760                 765

gtg aat gct ctc cac act tcc ttc cct gaa aac ccc cgt gca cag tac      2352
Val Asn Ala Leu His Thr Ser Phe Pro Glu Asn Pro Arg Ala Gln Tyr
    770                 775                 780

cag agg cag tgt gaa ctc att ctg gaa aag ctg gaa ctc cag ggc ctc      2400
Gln Arg Gln Cys Glu Leu Ile Leu Glu Lys Leu Glu Leu Gln Gly Leu
785                 790                 795                 800

ttg cag gaa gaa ctt cga aga ctg gaa agg tta cag aat gag agt gta      2448
Leu Gln Glu Glu Leu Arg Arg Leu Glu Arg Leu Gln Asn Glu Ser Val
                805                 810                 815

cac caa tgc cag tca cat tca cta gag gag gag gtg gct cca ggt tcc      2496
His Gln Cys Gln Ser His Ser Leu Glu Glu Glu Val Ala Pro Gly Ser
            820                 825                 830

tgc aga aat gat ccc agg gac aag cca agg ctc agg act tca aca cag      2544
Cys Arg Asn Asp Pro Arg Asp Lys Pro Arg Leu Arg Thr Ser Thr Gln
        835                 840                 845

cag gaa cag agc tgt agc tgg agt tcc aca gag aga tct ggt gca gac      2592
Gln Glu Gln Ser Cys Ser Trp Ser Ser Thr Glu Arg Ser Gly Ala Asp
    850                 855                 860

tcc ccg cct ggt cca ggg ctt aat aga cca aca agt tgt aac aac tca      2640
Ser Pro Pro Gly Pro Gly Leu Asn Arg Pro Thr Ser Cys Asn Asn Ser
865                 870                 875                 880

gct gag aac aga gat ggc aga ggt gac ggt tta gac tgg ttg gac ccc      2688
Ala Glu Asn Arg Asp Gly Arg Gly Asp Gly Leu Asp Trp Leu Asp Pro
                885                 890                 895

aca tca agt cct gag att gca cca gaa agc act att gtg tct ccc aat      2736
Thr Ser Ser Pro Glu Ile Ala Pro Glu Ser Thr Ile Val Ser Pro Asn
            900                 905                 910

gtg aaa aca act gag aaa aat gtg aat ttg aaa atc tcc aac aat aaa      2784
Val Lys Thr Thr Glu Lys Asn Val Asn Leu Lys Ile Ser Asn Asn Lys
        915                 920                 925

tct cag ggc aag gag aag cat ggg cca cag caa aga agc aaa tta tta      2832
Ser Gln Gly Lys Glu Lys His Gly Pro Gln Gln Arg Ser Lys Leu Leu
    930                 935                 940

gaa gct gga cat ctt cca tca tca gga gcc atg aat gcc ccc tta cgg      2880
Glu Ala Gly His Leu Pro Ser Ser Gly Ala Met Asn Ala Pro Leu Arg
945                 950                 955                 960

tct cac ggt gtt aag cgt aca aag gca agt cag gca gtg gtt gta tct      2928
Ser His Gly Val Lys Arg Thr Lys Ala Ser Gln Ala Val Val Val Ser
                965                 970                 975

gaa gca gga cgg ggt gat gaa gaa gac tct gtg ccc cga aga ctc ccc      2976
Glu Ala Gly Arg Gly Asp Glu Glu Asp Ser Val Pro Arg Arg Leu Pro
            980                 985                 990

aag ctg ctg aag gag ggg tca cag  aat gtg tgc aga agc  aca acc aga    3024
Lys Leu Leu Lys Glu Gly Ser Gln  Asn Val Cys Arg Ser  Thr Thr Arg
        995                 1000                1005

gtg cga  cca ctg cca ccc act  gtc cct ctg tcc ctg  tct atc cct      3069
Val Arg  Pro Leu Pro Pro Thr  Val Pro Leu Ser Leu  Ser Ile Pro
    1010                 1015                 1020
```

```
tca cct  ggg tca gga aaa aga  tca gga aca ccc aaa  aga aag aga      3114
Ser Pro  Gly Ser Gly Lys Arg  Ser Gly Thr Pro Lys  Arg Lys Arg
    1025                 1030                 1035

cgg aaa  tct gct cag gtg gaa  gag cct gaa cct gaa  ggt atg gag     3159
Arg Lys  Ser Ala Gln Val Glu  Glu Pro Glu Pro Glu  Gly Met Glu
    1040                 1045                 1050

act cca  aca gta aag ctg gcc  aaa ttc aca ttt aaa  cag aag aca     3204
Thr Pro  Thr Val Lys Leu Ala  Lys Phe Thr Phe Lys  Gln Lys Thr
    1055                 1060                 1065

aaa ctg  acc cac tcc ccc gaa  ggc caa ggc ccc ata  cct ccc agt     3249
Lys Leu  Thr His Ser Pro Glu  Gly Gln Gly Pro Ile  Pro Pro Ser
    1070                 1075                 1080

gct agt  gaa ata gca gtt gac  agt tct aaa att ccc  caa caa aga     3294
Ala Ser  Glu Ile Ala Val Asp  Ser Ser Lys Ile Pro  Gln Gln Arg
    1085                 1090                 1095

aca aga  aga gaa gca gct gtg  cct gtg gta gcg cca  gga aag tcg     3339
Thr Arg  Arg Glu Ala Ala Val  Pro Val Val Ala Pro  Gly Lys Ser
    1100                 1105                 1110

aca tcc  acc tca gga gac aga  tgc tct gac cag ctg  cac gga aag     3384
Thr Ser  Thr Ser Gly Asp Arg  Cys Ser Asp Gln Leu  His Gly Lys
    1115                 1120                 1125

aca aag  gag ctc tca agg cag  cca cca gac agt aat  cca cca aga     3429
Thr Lys  Glu Leu Ser Arg Gln  Pro Pro Asp Ser Asn  Pro Pro Arg
    1130                 1135                 1140

gag gag  agg gaa cag ggc ccc  aaa aga agg gtt att  cag ccc aaa     3474
Glu Glu  Arg Glu Gln Gly Pro  Lys Arg Arg Val Ile  Gln Pro Lys
    1145                 1150                 1155

ccg gag  ctt ggg aac cag gct  ggg cat tcg cat cta  gcc tgt gag     3519
Pro Glu  Leu Gly Asn Gln Ala  Gly His Ser His Leu  Ala Cys Glu
    1160                 1165                 1170

aaa gac  aga aag gaa ggg gtt  tcc tgc ggt aat aaa  agc agc aag     3564
Lys Asp  Arg Lys Glu Gly Val  Ser Cys Gly Asn Lys  Ser Ser Lys
    1175                 1180                 1185

gtt cat  gct ggc acc ata gcc  aga ctg gca agc ttc  tcc ttc act     3609
Val His  Ala Gly Thr Ile Ala  Arg Leu Ala Ser Phe  Ser Phe Thr
    1190                 1195                 1200

tcc cca  tca gaa tcc aaa tcg  gaa tcc ctc cct cct  gaa agg aag     3654
Ser Pro  Ser Glu Ser Lys Ser  Glu Ser Leu Pro Pro  Glu Arg Lys
    1205                 1210                 1215

gac agc  agg gac agc agg gac  agc agg gac agc agg  gac agg tgc     3699
Asp Ser  Arg Asp Ser Arg Asp  Ser Arg Asp Ser Arg  Asp Arg Cys
    1220                 1225                 1230

cac agc  cct cct gcg acc aca  gct cca gtg ctc ggc  cag caa agg     3744
His Ser  Pro Pro Ala Thr Thr  Ala Pro Val Leu Gly  Gln Gln Arg
    1235                 1240                 1245

cag act  ttc cag ctg cag cag  ccc aca gag aga gcg  aat ctt tcc     3789
Gln Thr  Phe Gln Leu Gln Gln  Pro Thr Glu Arg Ala  Asn Leu Ser
    1250                 1255                 1260

acc ctc  tcc ctc ttc act ctg  tcg gaa cta gat gac  gaa gca tta     3834
Thr Leu  Ser Leu Phe Thr Leu  Ser Glu Leu Asp Asp  Glu Ala Leu
    1265                 1270                 1275

gat ttt  gac tgg gag gaa gag  atg agg aaa aag cca  tga             3873
Asp Phe  Asp Trp Glu Glu Glu  Met Arg Lys Lys Pro
    1280                 1285                 1290


<210> SEQ ID NO 8
<211> LENGTH: 1290
<212> TYPE: PRT
<213> ORGANISM: Mus musculus

<400> SEQUENCE: 8
```

-continued

```
Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
            20                  25                  30

Arg Leu Val Arg Pro Lys Pro Arg Leu Gln Leu Pro Glu Ser Arg Leu
        35                  40                  45

Ser Pro Cys Ser Arg Leu Pro Leu Ala Asp Ser Ser Val Arg Pro Gly
    50                  55                  60

Ala Arg Pro Pro Ala Ser Ala Pro Gly Arg Ser Pro Ser Gly Arg Lys
65                  70                  75                  80

Val Glu Ala Val Arg Gly Ser Gly Ser Ala Gly Ser Ser Ser Pro Ser
                85                  90                  95

Glu Ala Glu Arg Glu Gln Arg Glu Glu Ala Cys Ala Pro Pro Arg Lys
            100                 105                 110

Ala Ala Pro Ser Ser Gly Arg Ala His Ala Pro Pro Pro Pro Thr Pro
        115                 120                 125

Arg Gly Ser Gly Trp Gly Asp His Gly Arg Ser Ala Val Pro Ala Thr
    130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
                165                 170                 175

His Lys Asn Asp Ile Leu Leu Ile Leu Lys Glu Arg Asp Glu Asp Ala
            180                 185                 190

His Tyr Pro Val Val Val Asn Ala Met Ser Leu Phe Glu Thr Asn Met
        195                 200                 205

Glu Ile Gly Asp Tyr Phe Thr Val Phe Pro Asn Glu Val Leu Thr Val
    210                 215                 220

Phe Asp Ser Ala Leu Arg Arg Ser Ala Leu Ala Ile Leu Gln Ser Leu
225                 230                 235                 240

Pro Glu Thr Glu Gly Leu Ser Met Lys Gln Asn Leu His Ala Arg Ile
                245                 250                 255

Ser Gly Leu Pro Val Cys Pro Glu Leu Val Arg Glu His Ile Pro Lys
            260                 265                 270

Thr Lys Asp Val Gly His Phe Leu Ser Val Thr Gly Thr Val Ile Arg
        275                 280                 285

Thr Ser Leu Val Lys Val Leu Glu Phe Glu Arg Asp Tyr Met Cys Asn
    290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
                325                 330                 335

Ser Lys Phe Ser Cys Leu Ser Asp Leu Ser Ser Ser Pro Ala Arg Cys
            340                 345                 350

Arg Asp Tyr Gln Glu Ile Lys Ile Gln Glu Gln Val Gln Arg Leu Ser
        355                 360                 365

Val Gly Ser Ile Pro Arg Ser Met Lys Val Ile Leu Glu Asp Asp Leu
    370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
                405                 410                 415
```

```
Ile Val Leu Lys Ala Asn Tyr Val Gln Val Asn Asn Glu Gln Ser Ser
            420                 425                 430

Gly Met Val Met Asp Glu Asp Thr Arg Lys Glu Phe Glu Asp Phe Trp
        435                 440                 445

Glu His Tyr Lys Ser Asp Pro Phe Ala Gly Arg Asn Glu Ile Leu Ala
    450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala Gly Leu Thr Val Thr
    530                 535                 540

Ala Val Lys Asp Ser Gly Glu Trp Asn Leu Glu Ala Gly Ala Leu Val
545                 550                 555                 560

Leu Ala Asp Ala Gly Leu Cys Cys Ile Asp Glu Phe Asn Ser Leu Lys
                565                 570                 575

Glu His Asp Arg Thr Ser Ile His Glu Ala Met Glu Gln Gln Thr Ile
            580                 585                 590

Ser Val Ala Lys Ala Gly Leu Val Cys Lys Leu Asn Thr Arg Thr Thr
        595                 600                 605

Ile Leu Ala Ala Thr Asn Pro Lys Gly Gln Tyr Asp Pro Lys Glu Ser
    610                 615                 620

Val Ser Val Asn Ile Ala Leu Gly Ser Pro Leu Leu Ser Arg Phe Asp
625                 630                 635                 640

Leu Val Leu Val Leu Leu Asp Thr Arg Asn Glu Asp Trp Asp Arg Ile
                645                 650                 655

Ile Ser Ser Phe Ile Leu Glu Asn Lys Gly Tyr Pro Ser Lys Ser Glu
            660                 665                 670

Asn Leu Trp Ser Met Glu Lys Met Lys Thr Tyr Phe Cys Leu Ile Arg
        675                 680                 685

Asn Leu His Pro Thr Leu Ser Glu Val Ser Asn Gln Val Leu Leu Arg
    690                 695                 700

Tyr Tyr Gln Met Gln Arg Gln Ser Asp Ser Arg Asn Ala Ala Arg Thr
705                 710                 715                 720

Thr Ile Arg Leu Leu Glu Ser Leu Ile Arg Leu Ala Glu Ala His Ala
                725                 730                 735

Arg Leu Met Phe Arg Ser Ala Val Thr Leu Glu Asp Ala Val Thr Ala
            740                 745                 750

Val Ser Val Met Glu Ser Ser Met Gln Gly Gly Ala Leu Leu Gly Gly
        755                 760                 765

Val Asn Ala Leu His Thr Ser Phe Pro Glu Asn Pro Arg Ala Gln Tyr
    770                 775                 780

Gln Arg Gln Cys Glu Leu Ile Leu Glu Lys Leu Glu Leu Gln Gly Leu
785                 790                 795                 800

Leu Gln Glu Glu Leu Arg Arg Leu Glu Arg Leu Gln Asn Glu Ser Val
                805                 810                 815

His Gln Cys Gln Ser His Ser Leu Glu Glu Glu Val Ala Pro Gly Ser
            820                 825                 830

Cys Arg Asn Asp Pro Arg Asp Lys Pro Arg Leu Arg Thr Ser Thr Gln
```

-continued

```
        835                 840                 845

Gln Glu Gln Ser Cys Ser Trp Ser Ser Thr Glu Arg Ser Gly Ala Asp
    850                 855                 860

Ser Pro Pro Gly Pro Gly Leu Asn Arg Pro Thr Ser Cys Asn Asn Ser
865                 870                 875                 880

Ala Glu Asn Arg Asp Gly Arg Gly Asp Gly Leu Asp Trp Leu Asp Pro
                885                 890                 895

Thr Ser Ser Pro Glu Ile Ala Pro Glu Ser Thr Ile Val Ser Pro Asn
            900                 905                 910

Val Lys Thr Thr Glu Lys Asn Val Asn Leu Lys Ile Ser Asn Asn Lys
        915                 920                 925

Ser Gln Gly Lys Glu Lys His Gly Pro Gln Gln Arg Ser Lys Leu Leu
    930                 935                 940

Glu Ala Gly His Leu Pro Ser Ser Gly Ala Met Asn Ala Pro Leu Arg
945                 950                 955                 960

Ser His Gly Val Lys Arg Thr Lys Ala Ser Gln Ala Val Val Val Ser
                965                 970                 975

Glu Ala Gly Arg Gly Asp Glu Glu Asp Ser Val Pro Arg Arg Leu Pro
            980                 985                 990

Lys Leu Leu Lys Glu Gly Ser Gln  Asn Val Cys Arg Ser  Thr Thr Arg
        995                 1000                1005

Val Arg  Pro Leu Pro Pro Thr  Val Pro Leu Ser Leu  Ser Ile Pro
    1010                1015                1020

Ser Pro  Gly Ser Gly Lys Arg  Ser Gly Thr Pro Lys  Arg Lys Arg
    1025                1030                1035

Arg Lys  Ser Ala Gln Val Glu  Glu Pro Glu Pro Glu  Gly Met Glu
    1040                1045                1050

Thr Pro  Thr Val Lys Leu Ala  Lys Phe Thr Phe Lys  Gln Lys Thr
    1055                1060                1065

Lys Leu  Thr His Ser Pro Glu  Gly Gln Gly Pro Ile  Pro Pro Ser
    1070                1075                1080

Ala Ser  Glu Ile Ala Val Asp  Ser Ser Lys Ile Pro  Gln Gln Arg
    1085                1090                1095

Thr Arg  Arg Glu Ala Ala Val  Pro Val Val Ala Pro  Gly Lys Ser
    1100                1105                1110

Thr Ser  Thr Ser Gly Asp Arg  Cys Ser Asp Gln Leu  His Gly Lys
    1115                1120                1125

Thr Lys  Glu Leu Ser Arg Gln  Pro Pro Asp Ser Asn  Pro Pro Arg
    1130                1135                1140

Glu Glu  Arg Glu Gln Gly Pro  Lys Arg Arg Val Ile  Gln Pro Lys
    1145                1150                1155

Pro Glu  Leu Gly Asn Gln Ala  Gly His Ser His Leu  Ala Cys Glu
    1160                1165                1170

Lys Asp  Arg Lys Glu Gly Val  Ser Cys Gly Asn Lys  Ser Ser Lys
    1175                1180                1185

Val His  Ala Gly Thr Ile Ala  Arg Leu Ala Ser Phe  Ser Phe Thr
    1190                1195                1200

Ser Pro  Ser Glu Ser Lys Ser  Glu Ser Leu Pro Pro  Glu Arg Lys
    1205                1210                1215

Asp Ser  Arg Asp Ser Arg Asp  Ser Arg Asp Ser Arg  Asp Arg Cys
    1220                1225                1230

His Ser  Pro Pro Ala Thr Thr  Ala Pro Val Leu Gly  Gln Gln Arg
    1235                1240                1245
```

```
Gln Thr  Phe Gln Leu Gln Gln  Pro Thr Glu Arg Ala  Asn Leu Ser
    1250                 1255                 1260

Thr Leu  Ser Leu Phe Thr Leu  Ser Glu Leu Asp Asp  Glu Ala Leu
    1265                 1270                 1275

Asp Phe  Asp Trp Glu Glu Glu  Met Arg Lys Lys Pro
    1280                 1285                 1290


<210> SEQ ID NO 9
<211> LENGTH: 2256
<212> TYPE: DNA
<213> ORGANISM: Mus musculus
<220> FEATURE:
<221> NAME/KEY: CDS
<222> LOCATION: (1)..(2256)

<400> SEQUENCE: 9

ggt ctg acc gtg aca gct gtc aaa gac tca gga gaa tgg aat cta gag       48
Gly Leu Thr Val Thr Ala Val Lys Asp Ser Gly Glu Trp Asn Leu Glu
1               5                   10                  15

gct ggg gct ttg gtg ctt gca gat gct ggt ctc tgc tgt att gac gaa       96
Ala Gly Ala Leu Val Leu Ala Asp Ala Gly Leu Cys Cys Ile Asp Glu
            20                  25                  30

ttt aac agc ctc aaa gaa cat gac agg aca agc atc cat gaa gca atg      144
Phe Asn Ser Leu Lys Glu His Asp Arg Thr Ser Ile His Glu Ala Met
        35                  40                  45

gag caa caa acc ata agt gtt gct aag gct ggc ctt gtt tgt aag ctg      192
Glu Gln Gln Thr Ile Ser Val Ala Lys Ala Gly Leu Val Cys Lys Leu
    50                  55                  60

aac aca agg acc acc atc ctg gca gca act aac ccc aaa ggc cag tat      240
Asn Thr Arg Thr Thr Ile Leu Ala Ala Thr Asn Pro Lys Gly Gln Tyr
65                  70                  75                  80

gac ccc aag gag tct gtg tct gtg aac att gcc ctc ggg agc cca ctc      288
Asp Pro Lys Glu Ser Val Ser Val Asn Ile Ala Leu Gly Ser Pro Leu
                85                  90                  95

tta agt cga ttt gac ctt gtc ctg gtt ttg ctc gac act agg aat gaa      336
Leu Ser Arg Phe Asp Leu Val Leu Val Leu Leu Asp Thr Arg Asn Glu
            100                 105                 110

gac tgg gat cgt atc att tct tcc ttt atc tta gaa aat aaa ggt tat      384
Asp Trp Asp Arg Ile Ile Ser Ser Phe Ile Leu Glu Asn Lys Gly Tyr
        115                 120                 125

cca agc aaa tca gag aat ctg tgg agc atg gag aag atg aaa acc tac      432
Pro Ser Lys Ser Glu Asn Leu Trp Ser Met Glu Lys Met Lys Thr Tyr
    130                 135                 140

ttc tgc ctc att cgg aat ctc cac ccc aca ctg tct gaa gtg agc aat      480
Phe Cys Leu Ile Arg Asn Leu His Pro Thr Leu Ser Glu Val Ser Asn
145                 150                 155                 160

caa gtc ctc ctt cga tac tac caa atg caa agg cag agt gat tcc cgg      528
Gln Val Leu Leu Arg Tyr Tyr Gln Met Gln Arg Gln Ser Asp Ser Arg
                165                 170                 175

aat gca gcc cgg aca acc atc cgc ctg tta gaa agc ttg atc cga tta      576
Asn Ala Ala Arg Thr Thr Ile Arg Leu Leu Glu Ser Leu Ile Arg Leu
            180                 185                 190

gca gaa gct cac gct cgc ctg atg ttc cgc agt gcc gtg act ctg gaa      624
Ala Glu Ala His Ala Arg Leu Met Phe Arg Ser Ala Val Thr Leu Glu
        195                 200                 205

gat gcc gtt aca gct gta tct gtg atg gag tct tca atg cag gga ggt      672
Asp Ala Val Thr Ala Val Ser Val Met Glu Ser Ser Met Gln Gly Gly
    210                 215                 220

gct ctg cta gga ggt gtg aat gct ctc cac act tcc ttc cct gaa aac      720
Ala Leu Leu Gly Gly Val Asn Ala Leu His Thr Ser Phe Pro Glu Asn
```

-continued

```
225                 230                 235                 240

ccc cgt gca cag tac cag agg cag tgt gaa ctc att ctg gaa aag ctg       768
Pro Arg Ala Gln Tyr Gln Arg Gln Cys Glu Leu Ile Leu Glu Lys Leu
                245                 250                 255

gaa ctc cag ggc ctc ttg cag gaa gaa ctt cga aga ctg gaa agg tta       816
Glu Leu Gln Gly Leu Leu Gln Glu Glu Leu Arg Arg Leu Glu Arg Leu
            260                 265                 270

cag aat gag agt gta cac caa tgc cag tca cat tca cta gag gag gag       864
Gln Asn Glu Ser Val His Gln Cys Gln Ser His Ser Leu Glu Glu Glu
        275                 280                 285

gtg gct cca ggt tcc tgc aga aat gat ccc agg gac aag cca agg ctc       912
Val Ala Pro Gly Ser Cys Arg Asn Asp Pro Arg Asp Lys Pro Arg Leu
    290                 295                 300

agg act tca aca cag cag gaa cag agc tgt agc tgg agt tcc aca gag       960
Arg Thr Ser Thr Gln Gln Glu Gln Ser Cys Ser Trp Ser Ser Thr Glu
305                 310                 315                 320

aga tct ggt gca gac tcc ccg cct ggt cca ggg ctt aat aga cca aca      1008
Arg Ser Gly Ala Asp Ser Pro Pro Gly Pro Gly Leu Asn Arg Pro Thr
                325                 330                 335

agt tgt aac aac tca gct gag aac aga gat ggc aga ggt gac ggt tta      1056
Ser Cys Asn Asn Ser Ala Glu Asn Arg Asp Gly Arg Gly Asp Gly Leu
            340                 345                 350

gac tgg ttg gac ccc aca tca agt cct gag att gca cca gaa agc act      1104
Asp Trp Leu Asp Pro Thr Ser Ser Pro Glu Ile Ala Pro Glu Ser Thr
        355                 360                 365

att gtg tct ccc aat gtg aaa aca act gag aaa aat gtg aat ttg aaa      1152
Ile Val Ser Pro Asn Val Lys Thr Thr Glu Lys Asn Val Asn Leu Lys
    370                 375                 380

atc tcc aac aat aaa tct cag ggc aag gag aag cat ggg cca cag caa      1200
Ile Ser Asn Asn Lys Ser Gln Gly Lys Glu Lys His Gly Pro Gln Gln
385                 390                 395                 400

aga agc aaa tta tta gaa gct gga cat ctt cca tca tca gga gcc atg      1248
Arg Ser Lys Leu Leu Glu Ala Gly His Leu Pro Ser Ser Gly Ala Met
                405                 410                 415

aat gcc ccc tta cgg tct cac ggt gtt aag cgt aca aag gca agt cag      1296
Asn Ala Pro Leu Arg Ser His Gly Val Lys Arg Thr Lys Ala Ser Gln
            420                 425                 430

gca gtg gtt gta tct gaa gca gga cgg ggt gat gaa gaa gac tct gtg      1344
Ala Val Val Val Ser Glu Ala Gly Arg Gly Asp Glu Glu Asp Ser Val
        435                 440                 445

ccc cga aga ctc ccc aag ctg ctg aag gag ggg tca cag aat gtg tgc      1392
Pro Arg Arg Leu Pro Lys Leu Leu Lys Glu Gly Ser Gln Asn Val Cys
    450                 455                 460

aga agc aca acc aga gtg cga cca ctg cca ccc act gtc cct ctg tcc      1440
Arg Ser Thr Thr Arg Val Arg Pro Leu Pro Pro Thr Val Pro Leu Ser
465                 470                 475                 480

ctg tct atc cct tca cct ggg tca gga aaa aga tca gga aca ccc aaa      1488
Leu Ser Ile Pro Ser Pro Gly Ser Gly Lys Arg Ser Gly Thr Pro Lys
                485                 490                 495

aga aag aga cgg aaa tct gct cag gtg gaa gag cct gaa cct gaa ggt      1536
Arg Lys Arg Arg Lys Ser Ala Gln Val Glu Glu Pro Glu Pro Glu Gly
            500                 505                 510

atg gag act cca aca gta aag ctg gcc aaa ttc aca ttt aaa cag aag      1584
Met Glu Thr Pro Thr Val Lys Leu Ala Lys Phe Thr Phe Lys Gln Lys
        515                 520                 525

aca aaa ctg acc cac tcc ccc gaa ggc caa ggc ccc ata cct ccc agt      1632
Thr Lys Leu Thr His Ser Pro Glu Gly Gln Gly Pro Ile Pro Pro Ser
    530                 535                 540

gct agt gaa ata gca gtt gac agt tct aaa att ccc caa caa aga aca      1680
```

```
Ala Ser Glu Ile Ala Val Asp Ser Ser Lys Ile Pro Gln Gln Arg Thr
545                 550                 555                 560

aga aga gaa gca gct gtg cct gtg gta gcg cca gga aag tcg aca tcc      1728
Arg Arg Glu Ala Ala Val Pro Val Val Ala Pro Gly Lys Ser Thr Ser
                565                 570                 575

acc tca gga gac aga tgc tct gac cag ctg cac gga aag aca aag gag      1776
Thr Ser Gly Asp Arg Cys Ser Asp Gln Leu His Gly Lys Thr Lys Glu
            580                 585                 590

ctc tca agg cag cca cca gac agt aat cca cca aga gag gag agg gaa      1824
Leu Ser Arg Gln Pro Pro Asp Ser Asn Pro Pro Arg Glu Glu Arg Glu
        595                 600                 605

cag ggc ccc aaa aga agg gtt att cag ccc aaa ccg gag ctt ggg aac      1872
Gln Gly Pro Lys Arg Arg Val Ile Gln Pro Lys Pro Glu Leu Gly Asn
    610                 615                 620

cag gct ggg cat tcg cat cta gcc tgt gag aaa gac aga aag gaa ggg      1920
Gln Ala Gly His Ser His Leu Ala Cys Glu Lys Asp Arg Lys Glu Gly
625                 630                 635                 640

gtt tcc tgc ggt aat aaa agc agc aag gtt cat gct ggc acc ata gcc      1968
Val Ser Cys Gly Asn Lys Ser Ser Lys Val His Ala Gly Thr Ile Ala
                645                 650                 655

aga ctg gca agc ttc tcc ttc act tcc cca tca gaa tcc aaa tcg gaa      2016
Arg Leu Ala Ser Phe Ser Phe Thr Ser Pro Ser Glu Ser Lys Ser Glu
            660                 665                 670

tcc ctc cct cct gaa agg aag gac agc agg gac agc agg gac agc agg      2064
Ser Leu Pro Pro Glu Arg Lys Asp Ser Arg Asp Ser Arg Asp Ser Arg
        675                 680                 685

gac agc agg gac agg tgc cac agc cct cct gcg acc aca gct cca gtg      2112
Asp Ser Arg Asp Arg Cys His Ser Pro Pro Ala Thr Thr Ala Pro Val
    690                 695                 700

ctc ggc cag caa agg cag act ttc cag ctg cag cag ccc aca gag aga      2160
Leu Gly Gln Gln Arg Gln Thr Phe Gln Leu Gln Gln Pro Thr Glu Arg
705                 710                 715                 720

gcg aat ctt tcc acc ctc tcc ctc ttc act ctg tcg gaa cta gat gac      2208
Ala Asn Leu Ser Thr Leu Ser Leu Phe Thr Leu Ser Glu Leu Asp Asp
                725                 730                 735

gaa gca tta gat ttt gac tgg gag gaa gag atg agg aaa aag cca tga      2256
Glu Ala Leu Asp Phe Asp Trp Glu Glu Glu Met Arg Lys Lys Pro
            740                 745                 750


<210> SEQ ID NO 10
<211> LENGTH: 751
<212> TYPE: PRT
<213> ORGANISM: Mus musculus

<400> SEQUENCE: 10

Gly Leu Thr Val Thr Ala Val Lys Asp Ser Gly Glu Trp Asn Leu Glu
1               5                   10                  15

Ala Gly Ala Leu Val Leu Ala Asp Ala Gly Leu Cys Cys Ile Asp Glu
            20                  25                  30

Phe Asn Ser Leu Lys Glu His Asp Arg Thr Ser Ile His Glu Ala Met
        35                  40                  45

Glu Gln Gln Thr Ile Ser Val Ala Lys Ala Gly Leu Val Cys Lys Leu
    50                  55                  60

Asn Thr Arg Thr Thr Ile Leu Ala Ala Thr Asn Pro Lys Gly Gln Tyr
65                  70                  75                  80

Asp Pro Lys Glu Ser Val Ser Val Asn Ile Ala Leu Gly Ser Pro Leu
                85                  90                  95

Leu Ser Arg Phe Asp Leu Val Leu Val Leu Leu Asp Thr Arg Asn Glu
            100                 105                 110
```

```
Asp Trp Asp Arg Ile Ile Ser Ser Phe Ile Leu Glu Asn Lys Gly Tyr
        115                 120                 125

Pro Ser Lys Ser Glu Asn Leu Trp Ser Met Glu Lys Met Lys Thr Tyr
    130                 135                 140

Phe Cys Leu Ile Arg Asn Leu His Pro Thr Leu Ser Glu Val Ser Asn
145                 150                 155                 160

Gln Val Leu Leu Arg Tyr Tyr Gln Met Gln Arg Gln Ser Asp Ser Arg
                165                 170                 175

Asn Ala Ala Arg Thr Thr Ile Arg Leu Leu Glu Ser Leu Ile Arg Leu
            180                 185                 190

Ala Glu Ala His Ala Arg Leu Met Phe Arg Ser Ala Val Thr Leu Glu
        195                 200                 205

Asp Ala Val Thr Ala Val Ser Val Met Glu Ser Ser Met Gln Gly Gly
    210                 215                 220

Ala Leu Leu Gly Gly Val Asn Ala Leu His Thr Ser Phe Pro Glu Asn
225                 230                 235                 240

Pro Arg Ala Gln Tyr Gln Arg Gln Cys Glu Leu Ile Leu Glu Lys Leu
                245                 250                 255

Glu Leu Gln Gly Leu Leu Gln Glu Glu Leu Arg Arg Leu Glu Arg Leu
            260                 265                 270

Gln Asn Glu Ser Val His Gln Cys Gln Ser His Ser Leu Glu Glu Glu
        275                 280                 285

Val Ala Pro Gly Ser Cys Arg Asn Asp Pro Arg Asp Lys Pro Arg Leu
    290                 295                 300

Arg Thr Ser Thr Gln Gln Glu Gln Ser Cys Ser Trp Ser Ser Thr Glu
305                 310                 315                 320

Arg Ser Gly Ala Asp Ser Pro Pro Gly Pro Gly Leu Asn Arg Pro Thr
                325                 330                 335

Ser Cys Asn Asn Ser Ala Glu Asn Arg Asp Gly Arg Gly Asp Gly Leu
            340                 345                 350

Asp Trp Leu Asp Pro Thr Ser Ser Pro Glu Ile Ala Pro Glu Ser Thr
        355                 360                 365

Ile Val Ser Pro Asn Val Lys Thr Thr Glu Lys Asn Val Asn Leu Lys
    370                 375                 380

Ile Ser Asn Asn Lys Ser Gln Gly Lys Glu Lys His Gly Pro Gln Gln
385                 390                 395                 400

Arg Ser Lys Leu Leu Glu Ala Gly His Leu Pro Ser Ser Gly Ala Met
                405                 410                 415

Asn Ala Pro Leu Arg Ser His Gly Val Lys Arg Thr Lys Ala Ser Gln
            420                 425                 430

Ala Val Val Val Ser Glu Ala Gly Arg Gly Asp Glu Glu Asp Ser Val
        435                 440                 445

Pro Arg Arg Leu Pro Lys Leu Leu Lys Glu Gly Ser Gln Asn Val Cys
    450                 455                 460

Arg Ser Thr Thr Arg Val Arg Pro Leu Pro Pro Thr Val Pro Leu Ser
465                 470                 475                 480

Leu Ser Ile Pro Ser Pro Gly Ser Gly Lys Arg Ser Gly Thr Pro Lys
                485                 490                 495

Arg Lys Arg Arg Lys Ser Ala Gln Val Glu Glu Pro Glu Pro Glu Gly
            500                 505                 510

Met Glu Thr Pro Thr Val Lys Leu Ala Lys Phe Thr Phe Lys Gln Lys
        515                 520                 525
```

```
Thr Lys Leu Thr His Ser Pro Glu Gly Gln Gly Pro Ile Pro Pro Ser
    530                 535                 540

Ala Ser Glu Ile Ala Val Asp Ser Ser Lys Ile Pro Gln Gln Arg Thr
545                 550                 555                 560

Arg Arg Glu Ala Ala Val Pro Val Val Ala Pro Gly Lys Ser Thr Ser
                565                 570                 575

Thr Ser Gly Asp Arg Cys Ser Asp Gln Leu His Gly Lys Thr Lys Glu
            580                 585                 590

Leu Ser Arg Gln Pro Pro Asp Ser Asn Pro Pro Arg Glu Glu Arg Glu
        595                 600                 605

Gln Gly Pro Lys Arg Arg Val Ile Gln Pro Lys Pro Glu Leu Gly Asn
    610                 615                 620

Gln Ala Gly His Ser His Leu Ala Cys Glu Lys Asp Arg Lys Glu Gly
625                 630                 635                 640

Val Ser Cys Gly Asn Lys Ser Ser Lys Val His Ala Gly Thr Ile Ala
                645                 650                 655

Arg Leu Ala Ser Phe Ser Phe Thr Ser Pro Ser Glu Ser Lys Ser Glu
            660                 665                 670

Ser Leu Pro Pro Glu Arg Lys Asp Ser Arg Asp Ser Arg Asp Ser Arg
        675                 680                 685

Asp Ser Arg Asp Arg Cys His Ser Pro Pro Ala Thr Thr Ala Pro Val
    690                 695                 700

Leu Gly Gln Gln Arg Gln Thr Phe Gln Leu Gln Gln Pro Thr Glu Arg
705                 710                 715                 720

Ala Asn Leu Ser Thr Leu Ser Leu Phe Thr Leu Ser Glu Leu Asp Asp
                725                 730                 735

Glu Ala Leu Asp Phe Asp Trp Glu Glu Glu Met Arg Lys Lys Pro
            740                 745                 750


<210> SEQ ID NO 11
<211> LENGTH: 1617
<212> TYPE: DNA
<213> ORGANISM: Mus musculus
<220> FEATURE:
<221> NAME/KEY: CDS
<222> LOCATION: (1)..(1617)

<400> SEQUENCE: 11

atg gat cag aga act aca cga aat gga aaa tat tgt gac gtg gaa ccg       48
Met Asp Gln Arg Thr Thr Arg Asn Gly Lys Tyr Cys Asp Val Glu Pro
1               5                   10                  15

gtg tcc cgc tca aac ccc gcc cca tgc ctc cga gac ccg ccc ctc aga       96
Val Ser Arg Ser Asn Pro Ala Pro Cys Leu Arg Asp Pro Pro Leu Arg
            20                  25                  30

cgt ctt gtc cgg ccc aaa ccc cgc ctc cag ctc ccc gag tcc cgc ctc      144
Arg Leu Val Arg Pro Lys Pro Arg Leu Gln Leu Pro Glu Ser Arg Leu
        35                  40                  45

tct ccc tgc tcc cgc ctc ccg ctc gca gac tcc agc gtc cgt cct ggc      192
Ser Pro Cys Ser Arg Leu Pro Leu Ala Asp Ser Ser Val Arg Pro Gly
    50                  55                  60

gcg cgc ccg cct gcg tcc gca ccc gga aga agc ccc agc ggc cgg aaa      240
Ala Arg Pro Pro Ala Ser Ala Pro Gly Arg Ser Pro Ser Gly Arg Lys
65                  70                  75                  80

gtt gag gca gtg cgc ggc tcg ggg tcc gcg gga agc tca agt cct tca      288
Val Glu Ala Val Arg Gly Ser Gly Ser Ala Gly Ser Ser Ser Pro Ser
                85                  90                  95

gag gcc gag cga gag cag cgc gaa gaa gcc tgc gcg ccc ccg cgc aag      336
Glu Ala Glu Arg Glu Gln Arg Glu Glu Ala Cys Ala Pro Pro Arg Lys
```

-continued

```
            100                 105                 110

gcg gcc ccc tcg agc ggc cgc gcg cac gcc ccg ccc cct cca acg ccg      384
Ala Ala Pro Ser Ser Gly Arg Ala His Ala Pro Pro Pro Pro Thr Pro
        115                 120                 125

cgc ggg tcg ggc tgg ggc gac cac ggc cgc agc gcg gtc ccg gcg acc      432
Arg Gly Ser Gly Trp Gly Asp His Gly Arg Ser Ala Val Pro Ala Thr
    130                 135                 140

aag aca gtg cgt gtt gag ccc tac cca ccc ttc aag atg aat agt gag      480
Lys Thr Val Arg Val Glu Pro Tyr Pro Pro Phe Lys Met Asn Ser Glu
145                 150                 155                 160

cag gtc acc ctg gtg ggt cag gtg ttt gag tcc tat gtt tca gag tac      528
Gln Val Thr Leu Val Gly Gln Val Phe Glu Ser Tyr Val Ser Glu Tyr
                165                 170                 175

cat aag aac gat att ctt ctg atc ctg aaa gaa aga gat gaa gat gct      576
His Lys Asn Asp Ile Leu Leu Ile Leu Lys Glu Arg Asp Glu Asp Ala
            180                 185                 190

cac tac ccg gtt gtg gtt aat gct atg agc ctt ttc gag acc aac atg      624
His Tyr Pro Val Val Val Asn Ala Met Ser Leu Phe Glu Thr Asn Met
        195                 200                 205

gaa att ggg gac tat ttc acc gtg ttc ccc aat gaa gta cta aca gtt      672
Glu Ile Gly Asp Tyr Phe Thr Val Phe Pro Asn Glu Val Leu Thr Val
    210                 215                 220

ttt gac agt gca ctt cga agg tca gcc ttg gca att ctg cag tcc ctt      720
Phe Asp Ser Ala Leu Arg Arg Ser Ala Leu Ala Ile Leu Gln Ser Leu
225                 230                 235                 240

cct gag acg gag ggg tta tcc atg aag cag aat ctt cat gcc agg ata      768
Pro Glu Thr Glu Gly Leu Ser Met Lys Gln Asn Leu His Ala Arg Ile
                245                 250                 255

tca ggt ttg cct gtt tgt cca gaa ctg gtc agg gaa cac att ccc aaa      816
Ser Gly Leu Pro Val Cys Pro Glu Leu Val Arg Glu His Ile Pro Lys
            260                 265                 270

acc aag gat gtg gga cac ttc tta tct gtc act ggg aca gtg atc cga      864
Thr Lys Asp Val Gly His Phe Leu Ser Val Thr Gly Thr Val Ile Arg
        275                 280                 285

acg agt ctg gtg aag gtc ttg gag ttc gag cgg gat tac atg tgt aac      912
Thr Ser Leu Val Lys Val Leu Glu Phe Glu Arg Asp Tyr Met Cys Asn
    290                 295                 300

aaa tgc aag cat gtg ttc atg gtg gag gca gac ttc gag cag tat tac      960
Lys Cys Lys His Val Phe Met Val Glu Ala Asp Phe Glu Gln Tyr Tyr
305                 310                 315                 320

acc ttc agt cgg cca tcg tca tgt cca agt tta gcc agc tgt gac tcc     1008
Thr Phe Ser Arg Pro Ser Ser Cys Pro Ser Leu Ala Ser Cys Asp Ser
                325                 330                 335

tca aaa ttc tct tgc ctc tca gac ttg tct tca tct cca gcc aga tgt     1056
Ser Lys Phe Ser Cys Leu Ser Asp Leu Ser Ser Ser Pro Ala Arg Cys
            340                 345                 350

cgg gat tac cag gaa atc aaa att cag gag cag gtg caa agg ctg tct     1104
Arg Asp Tyr Gln Glu Ile Lys Ile Gln Glu Gln Val Gln Arg Leu Ser
        355                 360                 365

gtt gga agt atc cca cgg tct atg aaa gtt att ctg gaa gat gac cta     1152
Val Gly Ser Ile Pro Arg Ser Met Lys Val Ile Leu Glu Asp Asp Leu
    370                 375                 380

gtt gac agt tgc aaa tct gga gat gac ctc acc atc tat ggg gtt gta     1200
Val Asp Ser Cys Lys Ser Gly Asp Asp Leu Thr Ile Tyr Gly Val Val
385                 390                 395                 400

atg caa cgg tgg aaa ccc ttt cag cga gat gta cgc tgt gaa gtt gag     1248
Met Gln Arg Trp Lys Pro Phe Gln Arg Asp Val Arg Cys Glu Val Glu
                405                 410                 415

att gtc ttg aaa gcc aac tat gtc caa gtg aat aat gag caa tcc tcg     1296
```

```
Ile Val Leu Lys Ala Asn Tyr Val Gln Val Asn Asn Glu Gln Ser Ser
            420                 425                 430

ggg atg gtc atg gat gag gac act cga aaa gaa ttt gaa gac ttc tgg     1344
Gly Met Val Met Asp Glu Asp Thr Arg Lys Glu Phe Glu Asp Phe Trp
        435                 440                 445

gaa cac tat aag agt gac ccc ttt gca ggg agg aat gaa ata ttg gcc     1392
Glu His Tyr Lys Ser Asp Pro Phe Ala Gly Arg Asn Glu Ile Leu Ala
    450                 455                 460

agc ttg tgt cct caa gtt ttt ggg atg tat cta gtg aag ctt gct gtg     1440
Ser Leu Cys Pro Gln Val Phe Gly Met Tyr Leu Val Lys Leu Ala Val
465                 470                 475                 480

gcc atg gta ctg gct ggt gga att caa aga act gat gct gca gga acc     1488
Ala Met Val Leu Ala Gly Gly Ile Gln Arg Thr Asp Ala Ala Gly Thr
                485                 490                 495

agg gtt aga ggg gaa tct cac ctt tta ttg gtt ggg gat cct ggc aca     1536
Arg Val Arg Gly Glu Ser His Leu Leu Leu Val Gly Asp Pro Gly Thr
            500                 505                 510

ggg aaa tca caa ttc ctt aaa tat gca gca aag att acc cca agg tcc     1584
Gly Lys Ser Gln Phe Leu Lys Tyr Ala Ala Lys Ile Thr Pro Arg Ser
        515                 520                 525

gtt ttg acc aca gga att gga tct act agt gca                          1617
Val Leu Thr Thr Gly Ile Gly Ser Thr Ser Ala
    530                 535


<210> SEQ ID NO 12
<211> LENGTH: 539
<212> TYPE: PRT
<213> ORGANISM: Mus musculus

<400> SEQUENCE: 12

Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
            20                  25                  30

Arg Leu Val Arg Pro Lys Pro Arg Leu Gln Leu Pro Glu Ser Arg Leu
        35                  40                  45

Ser Pro Cys Ser Arg Leu Pro Leu Ala Asp Ser Ser Val Arg Pro Gly
    50                  55                  60

Ala Arg Pro Pro Ala Ser Ala Pro Gly Arg Ser Pro Ser Gly Arg Lys
65                  70                  75                  80

Val Glu Ala Val Arg Gly Ser Gly Ser Ala Gly Ser Ser Ser Pro Ser
                85                  90                  95

Glu Ala Glu Arg Glu Gln Arg Glu Glu Ala Cys Ala Pro Pro Arg Lys
            100                 105                 110

Ala Ala Pro Ser Ser Gly Arg Ala His Ala Pro Pro Pro Pro Thr Pro
        115                 120                 125

Arg Gly Ser Gly Trp Gly Asp His Gly Arg Ser Ala Val Pro Ala Thr
    130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
                165                 170                 175

His Lys Asn Asp Ile Leu Leu Ile Leu Lys Glu Arg Asp Glu Asp Ala
            180                 185                 190

His Tyr Pro Val Val Val Asn Ala Met Ser Leu Phe Glu Thr Asn Met
        195                 200                 205

Glu Ile Gly Asp Tyr Phe Thr Val Phe Pro Asn Glu Val Leu Thr Val
```

```
    210                 215                 220

Phe Asp Ser Ala Leu Arg Arg Ser Ala Leu Ala Ile Leu Gln Ser Leu
225                 230                 235                 240

Pro Glu Thr Glu Gly Leu Ser Met Lys Gln Asn Leu His Ala Arg Ile
                245                 250                 255

Ser Gly Leu Pro Val Cys Pro Glu Leu Val Arg Glu His Ile Pro Lys
            260                 265                 270

Thr Lys Asp Val Gly His Phe Leu Ser Val Thr Gly Thr Val Ile Arg
        275                 280                 285

Thr Ser Leu Val Lys Val Leu Glu Phe Glu Arg Asp Tyr Met Cys Asn
    290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
                325                 330                 335

Ser Lys Phe Ser Cys Leu Ser Asp Leu Ser Ser Ser Pro Ala Arg Cys
            340                 345                 350

Arg Asp Tyr Gln Glu Ile Lys Ile Gln Glu Gln Val Gln Arg Leu Ser
        355                 360                 365

Val Gly Ser Ile Pro Arg Ser Met Lys Val Ile Leu Glu Asp Asp Leu
    370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
                405                 410                 415

Ile Val Leu Lys Ala Asn Tyr Val Gln Val Asn Asn Glu Gln Ser Ser
            420                 425                 430

Gly Met Val Met Asp Glu Asp Thr Arg Lys Glu Phe Glu Asp Phe Trp
        435                 440                 445

Glu His Tyr Lys Ser Asp Pro Phe Ala Gly Arg Asn Glu Ile Leu Ala
    450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala
    530                 535


<210> SEQ ID NO 13
<211> LENGTH: 3432
<212> TYPE: DNA
<213> ORGANISM: Xenopus sp.
<220> FEATURE:
<221> NAME/KEY: CDS
<222> LOCATION: (1)..(3429)

<400> SEQUENCE: 13

atg tat ctc ggt ttt gaa caa gta gcg ctg gtg ggc caa gtc ttt gaa       48
Met Tyr Leu Gly Phe Glu Gln Val Ala Leu Val Gly Gln Val Phe Glu
1               5                   10                  15

tcc ttt gtg ctg gag cac cac aaa aat gag att gcc cag ata ctt act       96
Ser Phe Val Leu Glu His His Lys Asn Glu Ile Ala Gln Ile Leu Thr
```

```
            20                  25                  30

gag aaa gaa gag cat gcc cac tac tca ctg gtt gtt aat gcc atg aca      144
Glu Lys Glu Glu His Ala His Tyr Ser Leu Val Val Asn Ala Met Thr
        35                  40                  45

ctt ttt gaa gca aac atg gag att gga gag tac ttt aat gcc ttt cca      192
Leu Phe Glu Ala Asn Met Glu Ile Gly Glu Tyr Phe Asn Ala Phe Pro
    50                  55                  60

aat gaa gtt ctg ccc gtc ttt gat aat gct ctg cgc tgt gct gcc atg      240
Asn Glu Val Leu Pro Val Phe Asp Asn Ala Leu Arg Cys Ala Ala Met
65                  70                  75                  80

agc ttt ctt cag tct tgt tca gaa aaa tac aca ttt ctt atg aag cag      288
Ser Phe Leu Gln Ser Cys Ser Glu Lys Tyr Thr Phe Leu Met Lys Gln
                85                  90                  95

aat ctt cat gca agg ata aca ggt cta cca gtg tgc cca gag tta acc      336
Asn Leu His Ala Arg Ile Thr Gly Leu Pro Val Cys Pro Glu Leu Thr
            100                 105                 110

aga gag cac ata cca cga acc aga gat gtg ggg cat ttc ctt tct gta      384
Arg Glu His Ile Pro Arg Thr Arg Asp Val Gly His Phe Leu Ser Val
        115                 120                 125

acc ggt aca gta att cgc acc agc ttg gtt aaa gtg ctc gag tat gag      432
Thr Gly Thr Val Ile Arg Thr Ser Leu Val Lys Val Leu Glu Tyr Glu
    130                 135                 140

caa gac ttc atg tgc aac aag tgt aag cat gtg gtc act gtg aaa gca      480
Gln Asp Phe Met Cys Asn Lys Cys Lys His Val Val Thr Val Lys Ala
145                 150                 155                 160

gac ttt gag cag cat tac aca ttc aag cca ccc atc gct tgc tca aat      528
Asp Phe Glu Gln His Tyr Thr Phe Lys Pro Pro Ile Ala Cys Ser Asn
                165                 170                 175

gag gaa ggc tgc aac tcc acc aaa ttc acc tgt ctg tca gat tca tcc      576
Glu Glu Gly Cys Asn Ser Thr Lys Phe Thr Cys Leu Ser Asp Ser Ser
            180                 185                 190

tct cca gcc agc tgc aga gac tat caa gag atc aag att cag gaa cag      624
Ser Pro Ala Ser Cys Arg Asp Tyr Gln Glu Ile Lys Ile Gln Glu Gln
        195                 200                 205

gtt caa agg cta tct gtt ggc agt atc cct cga tca atg att gta gtt      672
Val Gln Arg Leu Ser Val Gly Ser Ile Pro Arg Ser Met Ile Val Val
    210                 215                 220

ttg gaa gat gac ctg gtt gac agc tgc aaa tct gga gat gat ata aca      720
Leu Glu Asp Asp Leu Val Asp Ser Cys Lys Ser Gly Asp Asp Ile Thr
225                 230                 235                 240

gtc tat ggt gtg gtg atg cag cgg tgg aaa ccc ctt tat ata gac atg      768
Val Tyr Gly Val Val Met Gln Arg Trp Lys Pro Leu Tyr Ile Asp Met
                245                 250                 255

cgc tgt gac ctg gaa att gtt tta aag gcc aat tac att tca gtc aat      816
Arg Cys Asp Leu Glu Ile Val Leu Lys Ala Asn Tyr Ile Ser Val Asn
            260                 265                 270

aat gag caa cct tgt ggt gtg gtt ata aat gaa gaa gta cgc aaa gag      864
Asn Glu Gln Pro Cys Gly Val Val Ile Asn Glu Glu Val Arg Lys Glu
        275                 280                 285

tat gaa gat ttc tgg gtg aag tat agg aac aac cct tta gaa ggt agg      912
Tyr Glu Asp Phe Trp Val Lys Tyr Arg Asn Asn Pro Leu Glu Gly Arg
    290                 295                 300

aat gaa att ctg gcc agc ctg tgt ccg cag gta ttt ggt atg ttt gta      960
Asn Glu Ile Leu Ala Ser Leu Cys Pro Gln Val Phe Gly Met Phe Val
305                 310                 315                 320

gtg aag ctg gca gtg gcc atg gtg ctg gct ggt gga gtt cag aga att     1008
Val Lys Leu Ala Val Ala Met Val Leu Ala Gly Gly Val Gln Arg Ile
                325                 330                 335

gat tct gct gga aca aga gtg aga ggt gag tca cat ctt ctg cta gtt     1056
```

```
Asp Ser Ala Gly Thr Arg Val Arg Gly Glu Ser His Leu Leu Leu Val
            340                 345                 350

gga gac cct ggc acg ggg aaa tca cag ttt ctg aag tat gct gca aaa      1104
Gly Asp Pro Gly Thr Gly Lys Ser Gln Phe Leu Lys Tyr Ala Ala Lys
        355                 360                 365

att act ccg agg tct gtc ctt act gca ggc att gga tct act agt gca      1152
Ile Thr Pro Arg Ser Val Leu Thr Ala Gly Ile Gly Ser Thr Ser Ala
    370                 375                 380

ggc ttg act gtt act gca gtg aaa gac tct gga gag tgg aat ctg gag      1200
Gly Leu Thr Val Thr Ala Val Lys Asp Ser Gly Glu Trp Asn Leu Glu
385                 390                 395                 400

gct gga gcc ttg gtg tta gct gat gga ggc ctg tgc tgc att gat gaa      1248
Ala Gly Ala Leu Val Leu Ala Asp Gly Gly Leu Cys Cys Ile Asp Glu
                405                 410                 415

ttt aat agc atc aag gag cat gac aga acc agc atc cat gag gca atg      1296
Phe Asn Ser Ile Lys Glu His Asp Arg Thr Ser Ile His Glu Ala Met
            420                 425                 430

gag cag cag acc atc agt gtt gca aag gct ggg tta gtg tgc aag ctg      1344
Glu Gln Gln Thr Ile Ser Val Ala Lys Ala Gly Leu Val Cys Lys Leu
        435                 440                 445

aac act agg aca acc att ttg gca gca aca aat ccc aaa ggc caa tat      1392
Asn Thr Arg Thr Thr Ile Leu Ala Ala Thr Asn Pro Lys Gly Gln Tyr
    450                 455                 460

gac cca gac gaa tcc atc tcg gtg aat gta gcc ctt gct agc cct ctg      1440
Asp Pro Asp Glu Ser Ile Ser Val Asn Val Ala Leu Ala Ser Pro Leu
465                 470                 475                 480

ctc agc aga ttt gac ttg gtt cta gtt ttg ctg gat acc aaa aat gaa      1488
Leu Ser Arg Phe Asp Leu Val Leu Val Leu Leu Asp Thr Lys Asn Glu
                485                 490                 495

gac tgg gac cgc att att tct tcg ttt att ttg gag agt aaa ggc tgc      1536
Asp Trp Asp Arg Ile Ile Ser Ser Phe Ile Leu Glu Ser Lys Gly Cys
            500                 505                 510

cct cgt aaa tcc gat aag cta tgg agc atg gag aag atg aaa acc tat      1584
Pro Arg Lys Ser Asp Lys Leu Trp Ser Met Glu Lys Met Lys Thr Tyr
        515                 520                 525

ttc tgt ctt att aag aat ctt caa ccc aaa atg tct caa gat gct aat      1632
Phe Cys Leu Ile Lys Asn Leu Gln Pro Lys Met Ser Gln Asp Ala Asn
    530                 535                 540

gtt atc ctg gta cgt tat tac cag cta cag cgg caa agc agt tgc agg      1680
Val Ile Leu Val Arg Tyr Tyr Gln Leu Gln Arg Gln Ser Ser Cys Arg
545                 550                 555                 560

aat gca gca cgt act act att aga ttg cta gaa agt ttg atc cgc cta      1728
Asn Ala Ala Arg Thr Thr Ile Arg Leu Leu Glu Ser Leu Ile Arg Leu
                565                 570                 575

gca gaa gcc cat gct cgg ata atg tat cgg gat gtt gtg acc acc gaa      1776
Ala Glu Ala His Ala Arg Ile Met Tyr Arg Asp Val Val Thr Thr Glu
            580                 585                 590

gat gcc ata acc gtg gtg tcc ata atg gag tcc tcg atg cag gga ggt      1824
Asp Ala Ile Thr Val Val Ser Ile Met Glu Ser Ser Met Gln Gly Gly
        595                 600                 605

gca tta ctt ggc ggt gtc aat gca tta cac aca tcc ttt cca gaa aat      1872
Ala Leu Leu Gly Gly Val Asn Ala Leu His Thr Ser Phe Pro Glu Asn
    610                 615                 620

cca agg gaa cag tat cgg ctt cag tgc gag ctc cta ttg gat aaa ctt      1920
Pro Arg Glu Gln Tyr Arg Leu Gln Cys Glu Leu Leu Leu Asp Lys Leu
625                 630                 635                 640

ggg ctt cag aaa ttg cta gag gaa gag ctt caa agg cta gaa agg cag      1968
Gly Leu Gln Lys Leu Leu Glu Glu Glu Leu Gln Arg Leu Glu Arg Gln
                645                 650                 655
```

-continued

```
caa agt gaa gac tcc ctt gag tct gat ctt ggg gaa agt gca aca aac      2016
Gln Ser Glu Asp Ser Leu Glu Ser Asp Leu Gly Glu Ser Ala Thr Asn
            660                 665                 670

ctc gtt gga cat aaa gta gtg cac agt gag tgt gtc atg gaa gaa acc      2064
Leu Val Gly His Lys Val Val His Ser Glu Cys Val Met Glu Glu Thr
        675                 680                 685

ttc agc act ttt gaa gct tct tct ttg cca gat gaa aca cac ctg gga      2112
Phe Ser Thr Phe Glu Ala Ser Ser Leu Pro Asp Glu Thr His Leu Gly
    690                 695                 700

gta act ggc agt gct gca ttc ata cag act cct aag aaa acc atc tcc      2160
Val Thr Gly Ser Ala Ala Phe Ile Gln Thr Pro Lys Lys Thr Ile Ser
705                 710                 715                 720

gat atg acc aaa agt gat gac acc att agg aag ggt acc att aca cct      2208
Asp Met Thr Lys Ser Asp Asp Thr Ile Arg Lys Gly Thr Ile Thr Pro
                725                 730                 735

gct gaa caa aac aga ggt att agc aca gat gcc gag tcc tct tta aaa      2256
Ala Glu Gln Asn Arg Gly Ile Ser Thr Asp Ala Glu Ser Ser Leu Lys
            740                 745                 750

caa ggt aat gca caa cca ctc gct ggt ggg cat ctc tct gaa aat aat      2304
Gln Gly Asn Ala Gln Pro Leu Ala Gly Gly His Leu Ser Glu Asn Asn
        755                 760                 765

ctt aca aaa tgc act gat aac agt ctt ggc tgg ttt gat aca ctt caa      2352
Leu Thr Lys Cys Thr Asp Asn Ser Leu Gly Trp Phe Asp Thr Leu Gln
    770                 775                 780

tcc att cag atg tct ccc atc acc aaa caa aga gaa gga tgc aca gct      2400
Ser Ile Gln Met Ser Pro Ile Thr Lys Gln Arg Glu Gly Cys Thr Ala
785                 790                 795                 800

gaa aag ctt caa caa gaa gtc ctt cct gta tca aca gaa agt agc tgc      2448
Glu Lys Leu Gln Gln Glu Val Leu Pro Val Ser Thr Glu Ser Ser Cys
                805                 810                 815

cat cct gca gac aaa aaa gtt gta aat tta gga ggg agg aac aaa ctt      2496
His Pro Ala Asp Lys Lys Val Val Asn Leu Gly Gly Arg Asn Lys Leu
            820                 825                 830

gaa gtt ttg caa gct agt gga agc agc cct ggg gga aat gga agg gat      2544
Glu Val Leu Gln Ala Ser Gly Ser Ser Pro Gly Gly Asn Gly Arg Asp
        835                 840                 845

ttg tca aat cac aca gtg act tgt gga agc agc cct gag aga aac aaa      2592
Leu Ser Asn His Thr Val Thr Cys Gly Ser Ser Pro Glu Arg Asn Lys
    850                 855                 860

aga gat ttg tca aat cac ata gtg act gag cat gtt tct aaa aag tgg      2640
Arg Asp Leu Ser Asn His Ile Val Thr Glu His Val Ser Lys Lys Trp
865                 870                 875                 880

cgg aga ata aat aaa gat tcc ctt tgt gga aaa aat gtg cca tct ttc      2688
Arg Arg Ile Asn Lys Asp Ser Leu Cys Gly Lys Asn Val Pro Ser Phe
                885                 890                 895

cag cct cag tct gaa aat aca gat tcg gct cca gtc tgc tcc agt gtt      2736
Gln Pro Gln Ser Glu Asn Thr Asp Ser Ala Pro Val Cys Ser Ser Val
            900                 905                 910

cct ctg cat agt acc cct gat gtt gcc cag aga agg aaa aga att att      2784
Pro Leu His Ser Thr Pro Asp Val Ala Gln Arg Arg Lys Arg Ile Ile
        915                 920                 925

gcc cag gtg gaa aag caa tcg aaa gca gaa gtg gag gat cca gac aca      2832
Ala Gln Val Glu Lys Gln Ser Lys Ala Glu Val Glu Asp Pro Asp Thr
    930                 935                 940

aaa gca cga cta gcc cag ttg gcc aag ttt tca ttt aag cga cat tca      2880
Lys Ala Arg Leu Ala Gln Leu Ala Lys Phe Ser Phe Lys Arg His Ser
945                 950                 955                 960

aaa ctg gtg cat tca cct gca ggg gat act gac aca gca tca aat gca      2928
Lys Leu Val His Ser Pro Ala Gly Asp Thr Asp Thr Ala Ser Asn Ala
                965                 970                 975
```

```
cag aaa cat gat cac cca gtc cag aaa att aca cta tca gag aag ttg     2976
Gln Lys His Asp His Pro Val Gln Lys Ile Thr Leu Ser Glu Lys Leu
            980                 985                 990

aac aat tta ggt agg act gta aat  aat gtg gat aaa tca  agc aat tct   3024
Asn Asn Leu Gly Arg Thr Val Asn  Asn Val Asp Lys Ser  Ser Asn Ser
        995                 1000                 1005

gtt aat  ggc tca aag cag caa  aag cat gta gag aat  aca tcc aaa     3069
Val Asn  Gly Ser Lys Gln Gln  Lys His Val Glu Asn  Thr Ser Lys
    1010                 1015                 1020

cag act  gta ata acg cag aag  agt aac ttt gaa tcg  aac aca tta     3114
Gln Thr  Val Ile Thr Gln Lys  Ser Asn Phe Glu Ser  Asn Thr Leu
    1025                 1030                 1035

aac gct  cct gtg cat gag aca  aag ttg aat gag ggg  tgt gac tcc     3159
Asn Ala  Pro Val His Glu Thr  Lys Leu Asn Glu Gly  Cys Asp Ser
    1040                 1045                 1050

aga aag  gtt tct tct agt aca  ctt gct aag tta gca  cgc ttt tct     3204
Arg Lys  Val Ser Ser Ser Thr  Leu Ala Lys Leu Ala  Arg Phe Ser
    1055                 1060                 1065

ttc tca  cct cct cct gaa aat  caa gca gcg gag acc  agc aag gaa     3249
Phe Ser  Pro Pro Pro Glu Asn  Gln Ala Ala Glu Thr  Ser Lys Glu
    1070                 1075                 1080

acc ctg  att tta cca aga gct  gtt gct cca ggc agc  aaa aga aag     3294
Thr Leu  Ile Leu Pro Arg Ala  Val Ala Pro Gly Ser  Lys Arg Lys
    1085                 1090                 1095

tgt ttt  gaa ctg aat cct tcc  act gat aaa acc aca  atg tca agt     3339
Cys Phe  Glu Leu Asn Pro Ser  Thr Asp Lys Thr Thr  Met Ser Ser
    1100                 1105                 1110

aaa tct  ctt ttc tct aca aca  gac tta gat gat gaa  gag tta gat     3384
Lys Ser  Leu Phe Ser Thr Thr  Asp Leu Asp Asp Glu  Glu Leu Asp
    1115                 1120                 1125

gtg gat  tgg gag gct gaa ata  aaa gga aat cag aga  att gcc aca     3429
Val Asp  Trp Glu Ala Glu Ile  Lys Gly Asn Gln Arg  Ile Ala Thr
    1130                 1135                 1140

tga                                                                 3432
```

<210> SEQ ID NO 14
<211> LENGTH: 1143
<212> TYPE: PRT
<213> ORGANISM: Xenopus sp.

<400> SEQUENCE: 14

```
Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
            20                  25                  30

Glu Lys Glu Glu His Ala His Tyr Ser Leu Val Val Asn Ala Met Thr
        35                  40                  45

Leu Phe Glu Ala Asn Met Glu Ile Gly Glu Tyr Phe Asn Ala Phe Pro
    50                  55                  60

Asn Glu Val Leu Pro Val Phe Asp Asn Ala Leu Arg Cys Ala Ala Met
65                  70                  75                  80

Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125
```

```
Thr Gly Thr Val Ile Arg Thr Ser Leu Val Lys Val Leu Glu Tyr Glu
    130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                165                 170                 175

Glu Glu Gly Cys Asn Ser Thr Lys Phe Thr Cys Leu Ser Asp Ser Ser
            180                 185                 190

Ser Pro Ala Ser Cys Arg Asp Tyr Gln Glu Ile Lys Ile Gln Glu Gln
        195                 200                 205

Val Gln Arg Leu Ser Val Gly Ser Ile Pro Arg Ser Met Ile Val Val
    210                 215                 220

Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                245                 250                 255

Arg Cys Asp Leu Glu Ile Val Leu Lys Ala Asn Tyr Ile Ser Val Asn
            260                 265                 270

Asn Glu Gln Pro Cys Gly Val Val Ile Asn Glu Glu Val Arg Lys Glu
        275                 280                 285

Tyr Glu Asp Phe Trp Val Lys Tyr Arg Asn Asn Pro Leu Glu Gly Arg
    290                 295                 300

Asn Glu Ile Leu Ala Ser Leu Cys Pro Gln Val Phe Gly Met Phe Val
305                 310                 315                 320

Val Lys Leu Ala Val Ala Met Val Leu Ala Gly Gly Val Gln Arg Ile
                325                 330                 335

Asp Ser Ala Gly Thr Arg Val Arg Gly Glu Ser His Leu Leu Leu Val
            340                 345                 350

Gly Asp Pro Gly Thr Gly Lys Ser Gln Phe Leu Lys Tyr Ala Ala Lys
        355                 360                 365

Ile Thr Pro Arg Ser Val Leu Thr Ala Gly Ile Gly Ser Thr Ser Ala
    370                 375                 380

Gly Leu Thr Val Thr Ala Val Lys Asp Ser Gly Glu Trp Asn Leu Glu
385                 390                 395                 400

Ala Gly Ala Leu Val Leu Ala Asp Gly Gly Leu Cys Cys Ile Asp Glu
                405                 410                 415

Phe Asn Ser Ile Lys Glu His Asp Arg Thr Ser Ile His Glu Ala Met
            420                 425                 430

Glu Gln Gln Thr Ile Ser Val Ala Lys Ala Gly Leu Val Cys Lys Leu
        435                 440                 445

Asn Thr Arg Thr Thr Ile Leu Ala Ala Thr Asn Pro Lys Gly Gln Tyr
    450                 455                 460

Asp Pro Asp Glu Ser Ile Ser Val Asn Val Ala Leu Ala Ser Pro Leu
465                 470                 475                 480

Leu Ser Arg Phe Asp Leu Val Leu Val Leu Leu Asp Thr Lys Asn Glu
                485                 490                 495

Asp Trp Asp Arg Ile Ile Ser Ser Phe Ile Leu Glu Ser Lys Gly Cys
            500                 505                 510

Pro Arg Lys Ser Asp Lys Leu Trp Ser Met Glu Lys Met Lys Thr Tyr
        515                 520                 525

Phe Cys Leu Ile Lys Asn Leu Gln Pro Lys Met Ser Gln Asp Ala Asn
    530                 535                 540

Val Ile Leu Val Arg Tyr Tyr Gln Leu Gln Arg Gln Ser Ser Cys Arg
```

```
545                 550                 555                 560

Asn Ala Ala Arg Thr Thr Ile Arg Leu Leu Glu Ser Leu Ile Arg Leu
                565                 570                 575

Ala Glu Ala His Ala Arg Ile Met Tyr Arg Asp Val Val Thr Thr Glu
            580                 585                 590

Asp Ala Ile Thr Val Val Ser Ile Met Glu Ser Ser Met Gln Gly Gly
        595                 600                 605

Ala Leu Leu Gly Gly Val Asn Ala Leu His Thr Ser Phe Pro Glu Asn
    610                 615                 620

Pro Arg Glu Gln Tyr Arg Leu Gln Cys Glu Leu Leu Leu Asp Lys Leu
625                 630                 635                 640

Gly Leu Gln Lys Leu Leu Glu Glu Glu Leu Gln Arg Leu Glu Arg Gln
                645                 650                 655

Gln Ser Glu Asp Ser Leu Glu Ser Asp Leu Gly Glu Ser Ala Thr Asn
            660                 665                 670

Leu Val Gly His Lys Val Val His Ser Glu Cys Val Met Glu Glu Thr
        675                 680                 685

Phe Ser Thr Phe Glu Ala Ser Ser Leu Pro Asp Glu Thr His Leu Gly
    690                 695                 700

Val Thr Gly Ser Ala Ala Phe Ile Gln Thr Pro Lys Lys Thr Ile Ser
705                 710                 715                 720

Asp Met Thr Lys Ser Asp Asp Thr Ile Arg Lys Gly Thr Ile Thr Pro
                725                 730                 735

Ala Glu Gln Asn Arg Gly Ile Ser Thr Asp Ala Glu Ser Ser Leu Lys
            740                 745                 750

Gln Gly Asn Ala Gln Pro Leu Ala Gly Gly His Leu Ser Glu Asn Asn
        755                 760                 765

Leu Thr Lys Cys Thr Asp Asn Ser Leu Gly Trp Phe Asp Thr Leu Gln
    770                 775                 780

Ser Ile Gln Met Ser Pro Ile Thr Lys Gln Arg Glu Gly Cys Thr Ala
785                 790                 795                 800

Glu Lys Leu Gln Gln Glu Val Leu Pro Val Ser Thr Glu Ser Ser Cys
                805                 810                 815

His Pro Ala Asp Lys Lys Val Val Asn Leu Gly Gly Arg Asn Lys Leu
            820                 825                 830

Glu Val Leu Gln Ala Ser Gly Ser Ser Pro Gly Gly Asn Gly Arg Asp
        835                 840                 845

Leu Ser Asn His Thr Val Thr Cys Gly Ser Ser Pro Glu Arg Asn Lys
    850                 855                 860

Arg Asp Leu Ser Asn His Ile Val Thr Glu His Val Ser Lys Lys Trp
865                 870                 875                 880

Arg Arg Ile Asn Lys Asp Ser Leu Cys Gly Lys Asn Val Pro Ser Phe
                885                 890                 895

Gln Pro Gln Ser Glu Asn Thr Asp Ser Ala Pro Val Cys Ser Ser Val
            900                 905                 910

Pro Leu His Ser Thr Pro Asp Val Ala Gln Arg Arg Lys Arg Ile Ile
        915                 920                 925

Ala Gln Val Glu Lys Gln Ser Lys Ala Glu Val Glu Asp Pro Asp Thr
    930                 935                 940

Lys Ala Arg Leu Ala Gln Leu Ala Lys Phe Ser Phe Lys Arg His Ser
945                 950                 955                 960

Lys Leu Val His Ser Pro Ala Gly Asp Thr Asp Thr Ala Ser Asn Ala
                965                 970                 975
```

```
Gln Lys His Asp His Pro Val Gln Lys Ile Thr Leu Ser Glu Lys Leu
            980                 985                 990

Asn Asn Leu Gly Arg Thr Val Asn  Asn Val Asp Lys Ser  Ser Asn Ser
        995                 1000                1005

Val Asn  Gly Ser Lys Gln Gln  Lys His Val Glu Asn  Thr Ser Lys
    1010                 1015                 1020

Gln Thr  Val Ile Thr Gln Lys  Ser Asn Phe Glu Ser  Asn Thr Leu
    1025                 1030                 1035

Asn Ala  Pro Val His Glu Thr  Lys Leu Asn Glu Gly  Cys Asp Ser
    1040                 1045                 1050

Arg Lys  Val Ser Ser Ser Thr  Leu Ala Lys Leu Ala  Arg Phe Ser
    1055                 1060                 1065

Phe Ser  Pro Pro Pro Glu Asn  Gln Ala Ala Glu Thr  Ser Lys Glu
    1070                 1075                 1080

Thr Leu  Ile Leu Pro Arg Ala  Val Ala Pro Gly Ser  Lys Arg Lys
    1085                 1090                 1095

Cys Phe  Glu Leu Asn Pro Ser  Thr Asp Lys Thr Thr  Met Ser Ser
    1100                 1105                 1110

Lys Ser  Leu Phe Ser Thr Thr  Asp Leu Asp Asp Glu  Glu Leu Asp
    1115                 1120                 1125

Val Asp  Trp Glu Ala Glu Ile  Lys Gly Asn Gln Arg  Ile Ala Thr
    1130                 1135                 1140


<210> SEQ ID NO 15
<211> LENGTH: 2280
<212> TYPE: DNA
<213> ORGANISM: Xenopus sp.
<220> FEATURE:
<221> NAME/KEY: CDS
<222> LOCATION: (1)..(2280)

<400> SEQUENCE: 15

ggc ttg act gtt act gca gtg aaa gac tct gga gag tgg aat ctg gag       48
Gly Leu Thr Val Thr Ala Val Lys Asp Ser Gly Glu Trp Asn Leu Glu
1               5                   10                  15

gct gga gcc ttg gtg tta gct gat gga ggc ctg tgc tgc att gat gaa       96
Ala Gly Ala Leu Val Leu Ala Asp Gly Gly Leu Cys Cys Ile Asp Glu
            20                  25                  30

ttt aat agc atc aag gag cat gac aga acc agc atc cat gag gca atg      144
Phe Asn Ser Ile Lys Glu His Asp Arg Thr Ser Ile His Glu Ala Met
        35                  40                  45

gag cag cag acc atc agt gtt gca aag gct ggg tta gtg tgc aag ctg      192
Glu Gln Gln Thr Ile Ser Val Ala Lys Ala Gly Leu Val Cys Lys Leu
    50                  55                  60

aac act agg aca acc att ttg gca gca aca aat ccc aaa ggc caa tat      240
Asn Thr Arg Thr Thr Ile Leu Ala Ala Thr Asn Pro Lys Gly Gln Tyr
65                  70                  75                  80

gac cca gac gaa tcc atc tcg gtg aat gta gcc ctt gct agc cct ctg      288
Asp Pro Asp Glu Ser Ile Ser Val Asn Val Ala Leu Ala Ser Pro Leu
                85                  90                  95

ctc agc aga ttt gac ttg gtt cta gtt ttg ctg gat acc aaa aat gaa      336
Leu Ser Arg Phe Asp Leu Val Leu Val Leu Leu Asp Thr Lys Asn Glu
            100                 105                 110

gac tgg gac cgc att att tct tcg ttt att ttg gag agt aaa ggc tgc      384
Asp Trp Asp Arg Ile Ile Ser Ser Phe Ile Leu Glu Ser Lys Gly Cys
        115                 120                 125

cct cgt aaa tcc gat aag cta tgg agc atg gag aag atg aaa acc tat      432
Pro Arg Lys Ser Asp Lys Leu Trp Ser Met Glu Lys Met Lys Thr Tyr
```

```
    130                 135                 140

ttc tgt ctt att aag aat ctt caa ccc aaa atg tct caa gat gct aat      480
Phe Cys Leu Ile Lys Asn Leu Gln Pro Lys Met Ser Gln Asp Ala Asn
145                 150                 155                 160

gtt atc ctg gta cgt tat tac cag cta cag cgg caa agc agt tgc agg      528
Val Ile Leu Val Arg Tyr Tyr Gln Leu Gln Arg Gln Ser Ser Cys Arg
                165                 170                 175

aat gca gca cgt act act att aga ttg cta gaa agt ttg atc cgc cta      576
Asn Ala Ala Arg Thr Thr Ile Arg Leu Leu Glu Ser Leu Ile Arg Leu
            180                 185                 190

gca gaa gcc cat gct cgg ata atg tat cgg gat gtt gtg acc acc gaa      624
Ala Glu Ala His Ala Arg Ile Met Tyr Arg Asp Val Val Thr Thr Glu
        195                 200                 205

gat gcc ata acc gtg gtg tcc ata atg gag tcc tcg atg cag gga ggt      672
Asp Ala Ile Thr Val Val Ser Ile Met Glu Ser Ser Met Gln Gly Gly
    210                 215                 220

gca tta ctt ggc ggt gtc aat gca tta cac aca tcc ttt cca gaa aat      720
Ala Leu Leu Gly Gly Val Asn Ala Leu His Thr Ser Phe Pro Glu Asn
225                 230                 235                 240

cca agg gaa cag tat cgg ctt cag tgc gag ctc cta ttg gat aaa ctt      768
Pro Arg Glu Gln Tyr Arg Leu Gln Cys Glu Leu Leu Leu Asp Lys Leu
                245                 250                 255

ggg ctt cag aaa ttg cta gag gaa gag ctt caa agg cta gaa agg cag      816
Gly Leu Gln Lys Leu Leu Glu Glu Glu Leu Gln Arg Leu Glu Arg Gln
            260                 265                 270

caa agt gaa gac tcc ctt gag tct gat ctt ggg gaa agt gca aca aac      864
Gln Ser Glu Asp Ser Leu Glu Ser Asp Leu Gly Glu Ser Ala Thr Asn
        275                 280                 285

ctc gtt gga cat aaa gta gtg cac agt gag tgt gtc atg gaa gaa acc      912
Leu Val Gly His Lys Val Val His Ser Glu Cys Val Met Glu Glu Thr
    290                 295                 300

ttc agc act ttt gaa gct tct tct ttg cca gat gaa aca cac ctg gga      960
Phe Ser Thr Phe Glu Ala Ser Ser Leu Pro Asp Glu Thr His Leu Gly
305                 310                 315                 320

gta act ggc agt gct gca ttc ata cag act cct aag aaa acc atc tcc     1008
Val Thr Gly Ser Ala Ala Phe Ile Gln Thr Pro Lys Lys Thr Ile Ser
                325                 330                 335

gat atg acc aaa agt gat gac acc att agg aag ggt acc att aca cct     1056
Asp Met Thr Lys Ser Asp Asp Thr Ile Arg Lys Gly Thr Ile Thr Pro
            340                 345                 350

gct gaa caa aac aga ggt att agc aca gat gcc gag tcc tct tta aaa     1104
Ala Glu Gln Asn Arg Gly Ile Ser Thr Asp Ala Glu Ser Ser Leu Lys
        355                 360                 365

caa ggt aat gca caa cca ctc gct ggt ggg cat ctc tct gaa aat aat     1152
Gln Gly Asn Ala Gln Pro Leu Ala Gly Gly His Leu Ser Glu Asn Asn
    370                 375                 380

ctt aca aaa tgc act gat aac agt ctt ggc tgg ttt gat aca ctt caa     1200
Leu Thr Lys Cys Thr Asp Asn Ser Leu Gly Trp Phe Asp Thr Leu Gln
385                 390                 395                 400

tcc att cag atg tct ccc atc acc aaa caa aga gaa gga tgc aca gct     1248
Ser Ile Gln Met Ser Pro Ile Thr Lys Gln Arg Glu Gly Cys Thr Ala
                405                 410                 415

gaa aag ctt caa caa gaa gtc ctt cct gta tca aca gaa agt agc tgc     1296
Glu Lys Leu Gln Gln Glu Val Leu Pro Val Ser Thr Glu Ser Ser Cys
            420                 425                 430

cat cct gca gac aaa aaa gtt gta aat tta gga ggg agg aac aaa ctt     1344
His Pro Ala Asp Lys Lys Val Val Asn Leu Gly Gly Arg Asn Lys Leu
        435                 440                 445

gaa gtt ttg caa gct agt gga agc agc cct ggg gga aat gga agg gat     1392
```

```
Glu Val Leu Gln Ala Ser Gly Ser Ser Pro Gly Gly Asn Gly Arg Asp
    450                 455                 460

ttg tca aat cac aca gtg act tgt gga agc agc cct gag aga aac aaa      1440
Leu Ser Asn His Thr Val Thr Cys Gly Ser Ser Pro Glu Arg Asn Lys
465                 470                 475                 480

aga gat ttg tca aat cac ata gtg act gag cat gtt tct aaa aag tgg      1488
Arg Asp Leu Ser Asn His Ile Val Thr Glu His Val Ser Lys Lys Trp
                485                 490                 495

cgg aga ata aat aaa gat tcc ctt tgt gga aaa aat gtg cca tct ttc      1536
Arg Arg Ile Asn Lys Asp Ser Leu Cys Gly Lys Asn Val Pro Ser Phe
            500                 505                 510

cag cct cag tct gaa aat aca gat tcg gct cca gtc tgc tcc agt gtt      1584
Gln Pro Gln Ser Glu Asn Thr Asp Ser Ala Pro Val Cys Ser Ser Val
        515                 520                 525

cct ctg cat agt acc cct gat gtt gcc cag aga agg aaa aga att att      1632
Pro Leu His Ser Thr Pro Asp Val Ala Gln Arg Arg Lys Arg Ile Ile
    530                 535                 540

gcc cag gtg gaa aag caa tcg aaa gca gaa gtg gag gat cca gac aca      1680
Ala Gln Val Glu Lys Gln Ser Lys Ala Glu Val Glu Asp Pro Asp Thr
545                 550                 555                 560

aaa gca cga cta gcc cag ttg gcc aag ttt tca ttt aag cga cat tca      1728
Lys Ala Arg Leu Ala Gln Leu Ala Lys Phe Ser Phe Lys Arg His Ser
                565                 570                 575

aaa ctg gtg cat tca cct gca ggg gat act gac aca gca tca aat gca      1776
Lys Leu Val His Ser Pro Ala Gly Asp Thr Asp Thr Ala Ser Asn Ala
            580                 585                 590

cag aaa cat gat cac cca gtc cag aaa att aca cta tca gag aag ttg      1824
Gln Lys His Asp His Pro Val Gln Lys Ile Thr Leu Ser Glu Lys Leu
        595                 600                 605

aac aat tta ggt agg act gta aat aat gtg gat aaa tca agc aat tct      1872
Asn Asn Leu Gly Arg Thr Val Asn Asn Val Asp Lys Ser Ser Asn Ser
    610                 615                 620

gtt aat ggc tca aag cag caa aag cat gta gag aat aca tcc aaa cag      1920
Val Asn Gly Ser Lys Gln Gln Lys His Val Glu Asn Thr Ser Lys Gln
625                 630                 635                 640

act gta ata acg cag aag agt aac ttt gaa tcg aac aca tta aac gct      1968
Thr Val Ile Thr Gln Lys Ser Asn Phe Glu Ser Asn Thr Leu Asn Ala
                645                 650                 655

cct gtg cat gag aca aag ttg aat gag ggg tgt gac tcc aga aag gtt      2016
Pro Val His Glu Thr Lys Leu Asn Glu Gly Cys Asp Ser Arg Lys Val
            660                 665                 670

tct tct agt aca ctt gct aag tta gca cgc ttt tct ttc tca cct cct      2064
Ser Ser Ser Thr Leu Ala Lys Leu Ala Arg Phe Ser Phe Ser Pro Pro
        675                 680                 685

cct gaa aat caa gca gcg gag acc agc aag gaa acc ctg att tta cca      2112
Pro Glu Asn Gln Ala Ala Glu Thr Ser Lys Glu Thr Leu Ile Leu Pro
    690                 695                 700

aga gct gtt gct cca ggc agc aaa aga aag tgt ttt gaa ctg aat cct      2160
Arg Ala Val Ala Pro Gly Ser Lys Arg Lys Cys Phe Glu Leu Asn Pro
705                 710                 715                 720

tcc act gat aaa acc aca atg tca agt aaa tct ctt ttc tct aca aca      2208
Ser Thr Asp Lys Thr Thr Met Ser Ser Lys Ser Leu Phe Ser Thr Thr
                725                 730                 735

gac tta gat gat gaa gag tta gat gtg gat tgg gag gct gaa ata aaa      2256
Asp Leu Asp Asp Glu Glu Leu Asp Val Asp Trp Glu Ala Glu Ile Lys
            740                 745                 750

gga aat cag aga att gcc aca tga                                      2280
Gly Asn Gln Arg Ile Ala Thr
        755
```

<210> SEQ ID NO 16
<211> LENGTH: 759
<212> TYPE: PRT
<213> ORGANISM: Xenopus sp.

<400> SEQUENCE: 16

```
Gly Leu Thr Val Thr Ala Val Lys Asp Ser Gly Glu Trp Asn Leu Glu
1               5                   10                  15

Ala Gly Ala Leu Val Leu Ala Asp Gly Gly Leu Cys Cys Ile Asp Glu
            20                  25                  30

Phe Asn Ser Ile Lys Glu His Asp Arg Thr Ser Ile His Glu Ala Met
        35                  40                  45

Glu Gln Gln Thr Ile Ser Val Ala Lys Ala Gly Leu Val Cys Lys Leu
    50                  55                  60

Asn Thr Arg Thr Thr Ile Leu Ala Ala Thr Asn Pro Lys Gly Gln Tyr
65                  70                  75                  80

Asp Pro Asp Glu Ser Ile Ser Val Asn Val Ala Leu Ala Ser Pro Leu
                85                  90                  95

Leu Ser Arg Phe Asp Leu Val Leu Val Leu Leu Asp Thr Lys Asn Glu
            100                 105                 110

Asp Trp Asp Arg Ile Ile Ser Ser Phe Ile Leu Glu Ser Lys Gly Cys
        115                 120                 125

Pro Arg Lys Ser Asp Lys Leu Trp Ser Met Glu Lys Met Lys Thr Tyr
    130                 135                 140

Phe Cys Leu Ile Lys Asn Leu Gln Pro Lys Met Ser Gln Asp Ala Asn
145                 150                 155                 160

Val Ile Leu Val Arg Tyr Tyr Gln Leu Gln Arg Gln Ser Ser Cys Arg
                165                 170                 175

Asn Ala Ala Arg Thr Thr Ile Arg Leu Leu Glu Ser Leu Ile Arg Leu
            180                 185                 190

Ala Glu Ala His Ala Arg Ile Met Tyr Arg Asp Val Val Thr Thr Glu
        195                 200                 205

Asp Ala Ile Thr Val Val Ser Ile Met Glu Ser Ser Met Gln Gly Gly
    210                 215                 220

Ala Leu Leu Gly Gly Val Asn Ala Leu His Thr Ser Phe Pro Glu Asn
225                 230                 235                 240

Pro Arg Glu Gln Tyr Arg Leu Gln Cys Glu Leu Leu Leu Asp Lys Leu
                245                 250                 255

Gly Leu Gln Lys Leu Leu Glu Glu Glu Leu Gln Arg Leu Glu Arg Gln
            260                 265                 270

Gln Ser Glu Asp Ser Leu Glu Ser Asp Leu Gly Glu Ser Ala Thr Asn
        275                 280                 285

Leu Val Gly His Lys Val Val His Ser Glu Cys Val Met Glu Glu Thr
    290                 295                 300

Phe Ser Thr Phe Glu Ala Ser Ser Leu Pro Asp Glu Thr His Leu Gly
305                 310                 315                 320

Val Thr Gly Ser Ala Ala Phe Ile Gln Thr Pro Lys Lys Thr Ile Ser
                325                 330                 335

Asp Met Thr Lys Ser Asp Asp Thr Ile Arg Lys Gly Thr Ile Thr Pro
            340                 345                 350

Ala Glu Gln Asn Arg Gly Ile Ser Thr Asp Ala Glu Ser Ser Leu Lys
        355                 360                 365

Gln Gly Asn Ala Gln Pro Leu Ala Gly Gly His Leu Ser Glu Asn Asn
    370                 375                 380
```

```
Leu Thr Lys Cys Thr Asp Asn Ser Leu Gly Trp Phe Asp Thr Leu Gln
385                 390                 395                 400

Ser Ile Gln Met Ser Pro Ile Thr Lys Gln Arg Glu Gly Cys Thr Ala
                405                 410                 415

Glu Lys Leu Gln Gln Glu Val Leu Pro Val Ser Thr Glu Ser Ser Cys
            420                 425                 430

His Pro Ala Asp Lys Lys Val Val Asn Leu Gly Gly Arg Asn Lys Leu
        435                 440                 445

Glu Val Leu Gln Ala Ser Gly Ser Ser Pro Gly Gly Asn Gly Arg Asp
    450                 455                 460

Leu Ser Asn His Thr Val Thr Cys Gly Ser Ser Pro Glu Arg Asn Lys
465                 470                 475                 480

Arg Asp Leu Ser Asn His Ile Val Thr Glu His Val Ser Lys Lys Trp
                485                 490                 495

Arg Arg Ile Asn Lys Asp Ser Leu Cys Gly Lys Asn Val Pro Ser Phe
            500                 505                 510

Gln Pro Gln Ser Glu Asn Thr Asp Ser Ala Pro Val Cys Ser Ser Val
        515                 520                 525

Pro Leu His Ser Thr Pro Asp Val Ala Gln Arg Arg Lys Arg Ile Ile
    530                 535                 540

Ala Gln Val Glu Lys Gln Ser Lys Ala Glu Val Glu Asp Pro Asp Thr
545                 550                 555                 560

Lys Ala Arg Leu Ala Gln Leu Ala Lys Phe Ser Phe Lys Arg His Ser
                565                 570                 575

Lys Leu Val His Ser Pro Ala Gly Asp Thr Asp Thr Ala Ser Asn Ala
            580                 585                 590

Gln Lys His Asp His Pro Val Gln Lys Ile Thr Leu Ser Glu Lys Leu
        595                 600                 605

Asn Asn Leu Gly Arg Thr Val Asn Asn Val Asp Lys Ser Ser Asn Ser
    610                 615                 620

Val Asn Gly Ser Lys Gln Gln Lys His Val Glu Asn Thr Ser Lys Gln
625                 630                 635                 640

Thr Val Ile Thr Gln Lys Ser Asn Phe Glu Ser Asn Thr Leu Asn Ala
                645                 650                 655

Pro Val His Glu Thr Lys Leu Asn Glu Gly Cys Asp Ser Arg Lys Val
            660                 665                 670

Ser Ser Ser Thr Leu Ala Lys Leu Ala Arg Phe Ser Phe Ser Pro Pro
        675                 680                 685

Pro Glu Asn Gln Ala Ala Glu Thr Ser Lys Glu Thr Leu Ile Leu Pro
    690                 695                 700

Arg Ala Val Ala Pro Gly Ser Lys Arg Lys Cys Phe Glu Leu Asn Pro
705                 710                 715                 720

Ser Thr Asp Lys Thr Thr Met Ser Ser Lys Ser Leu Phe Ser Thr Thr
                725                 730                 735

Asp Leu Asp Asp Glu Glu Leu Asp Val Asp Trp Glu Ala Glu Ile Lys
            740                 745                 750

Gly Asn Gln Arg Ile Ala Thr
        755
```

<210> SEQ ID NO 17
<211> LENGTH: 1152
<212> TYPE: DNA
<213> ORGANISM: Xenopus sp.
<220> FEATURE:

```
<221> NAME/KEY: CDS
<222> LOCATION: (1)..(1152)

<400> SEQUENCE: 17

atg tat ctc ggt ttt gaa caa gta gcg ctg gtg ggc caa gtc ttt gaa        48
Met Tyr Leu Gly Phe Glu Gln Val Ala Leu Val Gly Gln Val Phe Glu
1               5                   10                  15

tcc ttt gtg ctg gag cac cac aaa aat gag att gcc cag ata ctt act         96
Ser Phe Val Leu Glu His His Lys Asn Glu Ile Ala Gln Ile Leu Thr
            20                  25                  30

gag aaa gaa gag cat gcc cac tac tca ctg gtt gtt aat gcc atg aca        144
Glu Lys Glu Glu His Ala His Tyr Ser Leu Val Val Asn Ala Met Thr
        35                  40                  45

ctt ttt gaa gca aac atg gag att gga gag tac ttt aat gcc ttt cca        192
Leu Phe Glu Ala Asn Met Glu Ile Gly Glu Tyr Phe Asn Ala Phe Pro
    50                  55                  60

aat gaa gtt ctg ccc gtc ttt gat aat gct ctg cgc tgt gct gcc atg        240
Asn Glu Val Leu Pro Val Phe Asp Asn Ala Leu Arg Cys Ala Ala Met
65                  70                  75                  80

agc ttt ctt cag tct tgt tca gaa aaa tac aca ttt ctt atg aag cag        288
Ser Phe Leu Gln Ser Cys Ser Glu Lys Tyr Thr Phe Leu Met Lys Gln
                85                  90                  95

aat ctt cat gca agg ata aca ggt cta cca gtg tgc cca gag tta acc        336
Asn Leu His Ala Arg Ile Thr Gly Leu Pro Val Cys Pro Glu Leu Thr
            100                 105                 110

aga gag cac ata cca cga acc aga gat gtg ggg cat ttc ctt tct gta        384
Arg Glu His Ile Pro Arg Thr Arg Asp Val Gly His Phe Leu Ser Val
        115                 120                 125

acc ggt aca gta att cgc acc agc ttg gtt aaa gtg ctc gag tat gag        432
Thr Gly Thr Val Ile Arg Thr Ser Leu Val Lys Val Leu Glu Tyr Glu
    130                 135                 140

caa gac ttc atg tgc aac aag tgt aag cat gtg gtc act gtg aaa gca        480
Gln Asp Phe Met Cys Asn Lys Cys Lys His Val Val Thr Val Lys Ala
145                 150                 155                 160

gac ttt gag cag cat tac aca ttc aag cca ccc atc gct tgc tca aat        528
Asp Phe Glu Gln His Tyr Thr Phe Lys Pro Pro Ile Ala Cys Ser Asn
                165                 170                 175

gag gaa ggc tgc aac tcc acc aaa ttc acc tgt ctg tca gat tca tcc        576
Glu Glu Gly Cys Asn Ser Thr Lys Phe Thr Cys Leu Ser Asp Ser Ser
            180                 185                 190

tct cca gcc agc tgc aga gac tat caa gag atc aag att cag gaa cag        624
Ser Pro Ala Ser Cys Arg Asp Tyr Gln Glu Ile Lys Ile Gln Glu Gln
        195                 200                 205

gtt caa agg cta tct gtt ggc agt atc cct cga tca atg att gta gtt        672
Val Gln Arg Leu Ser Val Gly Ser Ile Pro Arg Ser Met Ile Val Val
    210                 215                 220

ttg gaa gat gac ctg gtt gac agc tgc aaa tct gga gat gat ata aca        720
Leu Glu Asp Asp Leu Val Asp Ser Cys Lys Ser Gly Asp Asp Ile Thr
225                 230                 235                 240

gtc tat ggt gtg gtg atg cag cgg tgg aaa ccc ctt tat ata gac atg        768
Val Tyr Gly Val Val Met Gln Arg Trp Lys Pro Leu Tyr Ile Asp Met
                245                 250                 255

cgc tgt gac ctg gaa att gtt tta aag gcc aat tac att tca gtc aat        816
Arg Cys Asp Leu Glu Ile Val Leu Lys Ala Asn Tyr Ile Ser Val Asn
            260                 265                 270

aat gag caa cct tgt ggt gtg gtt ata aat gaa gaa gta cgc aaa gag        864
Asn Glu Gln Pro Cys Gly Val Val Ile Asn Glu Glu Val Arg Lys Glu
        275                 280                 285

tat gaa gat ttc tgg gtg aag tat agg aac aac cct tta gaa ggt agg        912
Tyr Glu Asp Phe Trp Val Lys Tyr Arg Asn Asn Pro Leu Glu Gly Arg
```

```
    290                 295                 300

aat gaa att ctg gcc agc ctg tgt ccg cag gta ttt ggt atg ttt gta      960
Asn Glu Ile Leu Ala Ser Leu Cys Pro Gln Val Phe Gly Met Phe Val
305                 310                 315                 320

gtg aag ctg gca gtg gcc atg gtg ctg gct ggt gga gtt cag aga att     1008
Val Lys Leu Ala Val Ala Met Val Leu Ala Gly Gly Val Gln Arg Ile
                325                 330                 335

gat tct gct gga aca aga gtg aga ggt gag tca cat ctt ctg cta gtt     1056
Asp Ser Ala Gly Thr Arg Val Arg Gly Glu Ser His Leu Leu Leu Val
            340                 345                 350

gga gac cct ggc acg ggg aaa tca cag ttt ctg aag tat gct gca aaa     1104
Gly Asp Pro Gly Thr Gly Lys Ser Gln Phe Leu Lys Tyr Ala Ala Lys
        355                 360                 365

att act ccg agg tct gtc ctt act gca ggc att gga tct act agt gca     1152
Ile Thr Pro Arg Ser Val Leu Thr Ala Gly Ile Gly Ser Thr Ser Ala
    370                 375                 380


<210> SEQ ID NO 18
<211> LENGTH: 384
<212> TYPE: PRT
<213> ORGANISM: Xenopus sp.

<400> SEQUENCE: 18

Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
            20                  25                  30

Glu Lys Glu Glu His Ala His Tyr Ser Leu Val Val Asn Ala Met Thr
        35                  40                  45

Leu Phe Glu Ala Asn Met Glu Ile Gly Glu Tyr Phe Asn Ala Phe Pro
    50                  55                  60

Asn Glu Val Leu Pro Val Phe Asp Asn Ala Leu Arg Cys Ala Ala Met
65                  70                  75                  80

Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125

Thr Gly Thr Val Ile Arg Thr Ser Leu Val Lys Val Leu Glu Tyr Glu
    130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                165                 170                 175

Glu Glu Gly Cys Asn Ser Thr Lys Phe Thr Cys Leu Ser Asp Ser Ser
            180                 185                 190

Ser Pro Ala Ser Cys Arg Asp Tyr Gln Glu Ile Lys Ile Gln Glu Gln
        195                 200                 205

Val Gln Arg Leu Ser Val Gly Ser Ile Pro Arg Ser Met Ile Val Val
    210                 215                 220

Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                245                 250                 255

Arg Cys Asp Leu Glu Ile Val Leu Lys Ala Asn Tyr Ile Ser Val Asn
```

```
            260                 265                 270

Asn Glu Gln Pro Cys Gly Val Val Ile Asn Glu Glu Val Arg Lys Glu
        275                 280                 285

Tyr Glu Asp Phe Trp Val Lys Tyr Arg Asn Asn Pro Leu Glu Gly Arg
    290                 295                 300

Asn Glu Ile Leu Ala Ser Leu Cys Pro Gln Val Phe Gly Met Phe Val
305                 310                 315                 320

Val Lys Leu Ala Val Ala Met Val Leu Ala Gly Gly Val Gln Arg Ile
                325                 330                 335

Asp Ser Ala Gly Thr Arg Val Arg Gly Glu Ser His Leu Leu Leu Val
            340                 345                 350

Gly Asp Pro Gly Thr Gly Lys Ser Gln Phe Leu Lys Tyr Ala Ala Lys
        355                 360                 365

Ile Thr Pro Arg Ser Val Leu Thr Ala Gly Ile Gly Ser Thr Ser Ala
    370                 375                 380


<210> SEQ ID NO 19
<211> LENGTH: 453
<212> TYPE: DNA
<213> ORGANISM: Homo sapiens
<220> FEATURE:
<221> NAME/KEY: CDS
<222> LOCATION: (1)..(453)

<400> SEQUENCE: 19

ttt gca gga agg aat gta ata ttg gct agc ttg tgc cct caa gtg ttt       48
Phe Ala Gly Arg Asn Val Ile Leu Ala Ser Leu Cys Pro Gln Val Phe
1               5                   10                  15

gga atg tat cta gta aag ctt gct gtg gcc atg gtg ctg gct ggt ggg       96
Gly Met Tyr Leu Val Lys Leu Ala Val Ala Met Val Leu Ala Gly Gly
            20                  25                  30

att caa agg act gat gct aca gga aca cgg gtc aga gga gaa tct cat      144
Ile Gln Arg Thr Asp Ala Thr Gly Thr Arg Val Arg Gly Glu Ser His
        35                  40                  45

ctt tta ttg gtt ggg gat cct ggc aca ggg aaa tct cag ttc ctc aaa      192
Leu Leu Leu Val Gly Asp Pro Gly Thr Gly Lys Ser Gln Phe Leu Lys
    50                  55                  60

tat gca gca aag att aca cca aga tct gtg ctg acc aca gga att gga      240
Tyr Ala Ala Lys Ile Thr Pro Arg Ser Val Leu Thr Thr Gly Ile Gly
65                  70                  75                  80

tct act agt gca ggt ctg acg gta act gct gta aaa gac tca gga gaa      288
Ser Thr Ser Ala Gly Leu Thr Val Thr Ala Val Lys Asp Ser Gly Glu
                85                  90                  95

tgg aat ttg gag gct ggg gca tta gtt ctt gca gat gcg ggc ctt tgc      336
Trp Asn Leu Glu Ala Gly Ala Leu Val Leu Ala Asp Ala Gly Leu Cys
            100                 105                 110

tgt att gat gag ttc aat agc ctc aaa gag cat gat agg acc agt atc      384
Cys Ile Asp Glu Phe Asn Ser Leu Lys Glu His Asp Arg Thr Ser Ile
        115                 120                 125

cat gaa gca atg gag caa caa acc ata agt gtt gct aag gct ggc ctc      432
His Glu Ala Met Glu Gln Gln Thr Ile Ser Val Ala Lys Ala Gly Leu
    130                 135                 140

gtg tgc aag ctg aac aca agg                                          453
Val Cys Lys Leu Asn Thr Arg
145                 150


<210> SEQ ID NO 20
<211> LENGTH: 151
<212> TYPE: PRT
<213> ORGANISM: Homo sapiens
```

```
<400> SEQUENCE: 20

Phe Ala Gly Arg Asn Val Ile Leu Ala Ser Leu Cys Pro Gln Val Phe
1               5                   10                  15

Gly Met Tyr Leu Val Lys Leu Ala Val Ala Met Val Leu Ala Gly Gly
            20                  25                  30

Ile Gln Arg Thr Asp Ala Thr Gly Thr Arg Val Arg Gly Glu Ser His
        35                  40                  45

Leu Leu Leu Val Gly Asp Pro Gly Thr Gly Lys Ser Gln Phe Leu Lys
    50                  55                  60

Tyr Ala Ala Lys Ile Thr Pro Arg Ser Val Leu Thr Thr Gly Ile Gly
65                  70                  75                  80

Ser Thr Ser Ala Gly Leu Thr Val Thr Ala Val Lys Asp Ser Gly Glu
                85                  90                  95

Trp Asn Leu Glu Ala Gly Ala Leu Val Leu Ala Asp Ala Gly Leu Cys
            100                 105                 110

Cys Ile Asp Glu Phe Asn Ser Leu Lys Glu His Asp Arg Thr Ser Ile
        115                 120                 125

His Glu Ala Met Glu Gln Gln Thr Ile Ser Val Ala Lys Ala Gly Leu
    130                 135                 140

Val Cys Lys Leu Asn Thr Arg
145                 150


<210> SEQ ID NO 21
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 21

ttg tgc cct caa gtg ttt gga atg tat cta gta aag ctt gct gtg gcc       48
Leu Cys Pro Gln Val Phe Gly Met Tyr Leu Val Lys Leu Ala Val Ala
1               5                   10                  15

atg gtg ctg gct ggt ggg att caa agg act gat gct aca gga aca cgg       96
Met Val Leu Ala Gly Gly Ile Gln Arg Thr Asp Ala Thr Gly Thr Arg
            20                  25                  30

gtc aga gga gaa tct cat ctt tta ttg gtt ggg gat cct ggc aca ggg      144
Val Arg Gly Glu Ser His Leu Leu Leu Val Gly Asp Pro Gly Thr Gly
        35                  40                  45

aaa tct cag ttc ctc aaa tat gca gca aag att aca cca aga tct gtg      192
Lys Ser Gln Phe Leu Lys Tyr Ala Ala Lys Ile Thr Pro Arg Ser Val
    50                  55                  60

ctg acc aca gga att gga tct act agt gca ggt ctg acg gta act gct      240
Leu Thr Thr Gly Ile Gly Ser Thr Ser Ala Gly Leu Thr Val Thr Ala
65                  70                  75                  80

gta aaa gac tca gga gaa tgg aat ttg gag gct ggg gca tta gtt ctt      288
Val Lys Asp Ser Gly Glu Trp Asn Leu Glu Ala Gly Ala Leu Val Leu
                85                  90                  95

gca gat gcg ggc ctt tgc tgt att gat gag ttc aat agc ctc aaa gag      336
Ala Asp Ala Gly Leu Cys Cys Ile Asp Glu Phe Asn Ser Leu Lys Glu
            100                 105                 110

cat gat agg acc agt atc cat gaa gca                                  363
His Asp Arg Thr Ser Ile His Glu Ala
        115                 120


<210> SEQ ID NO 22
<211> LENGTH: 121
```

```
<212> TYPE: PRT
<213> ORGANISM: Homo sapiens

<400> SEQUENCE: 22

Leu Cys Pro Gln Val Phe Gly Met Tyr Leu Val Lys Leu Ala Val Ala
1               5                   10                  15

Met Val Leu Ala Gly Gly Ile Gln Arg Thr Asp Ala Thr Gly Thr Arg
            20                  25                  30

Val Arg Gly Glu Ser His Leu Leu Leu Val Gly Asp Pro Gly Thr Gly
        35                  40                  45

Lys Ser Gln Phe Leu Lys Tyr Ala Ala Lys Ile Thr Pro Arg Ser Val
    50                  55                  60

Leu Thr Thr Gly Ile Gly Ser Thr Ser Ala Gly Leu Thr Val Thr Ala
65                  70                  75                  80

Val Lys Asp Ser Gly Glu Trp Asn Leu Glu Ala Gly Ala Leu Val Leu
                85                  90                  95

Ala Asp Ala Gly Leu Cys Cys Ile Asp Glu Phe Asn Ser Leu Lys Glu
            100                 105                 110

His Asp Arg Thr Ser Ile His Glu Ala
        115                 120


<210> SEQ ID NO 23
<211> LENGTH: 198
<212> TYPE: DNA
<213> ORGANISM: Homo sapiens
<220> FEATURE:
<221> NAME/KEY: CDS
<222> LOCATION: (1)..(198)

<400> SEQUENCE: 23

ggg gat cct ggc aca ggg aaa tct cag ttc ctc aaa tat gca gca aag       48
Gly Asp Pro Gly Thr Gly Lys Ser Gln Phe Leu Lys Tyr Ala Ala Lys
1               5                   10                  15

att aca cca aga tct gtg ctg acc aca gga att gga tct act agt gca       96
Ile Thr Pro Arg Ser Val Leu Thr Thr Gly Ile Gly Ser Thr Ser Ala
            20                  25                  30

ggt ctg acg gta act gct gta aaa gac tca gga gaa tgg aat ttg gag      144
Gly Leu Thr Val Thr Ala Val Lys Asp Ser Gly Glu Trp Asn Leu Glu
        35                  40                  45

gct ggg gca tta gtt ctt gca gat gcg ggc ctt tgc tgt att gat gag      192
Ala Gly Ala Leu Val Leu Ala Asp Ala Gly Leu Cys Cys Ile Asp Glu
    50                  55                  60

ttc aat                                                              198
Phe Asn
65


<210> SEQ ID NO 24
<211> LENGTH: 66
<212> TYPE: PRT
<213> ORGANISM: Homo sapiens

<400> SEQUENCE: 24

Gly Asp Pro Gly Thr Gly Lys Ser Gln Phe Leu Lys Tyr Ala Ala Lys
1               5                   10                  15

Ile Thr Pro Arg Ser Val Leu Thr Thr Gly Ile Gly Ser Thr Ser Ala
            20                  25                  30

Gly Leu Thr Val Thr Ala Val Lys Asp Ser Gly Glu Trp Asn Leu Glu
        35                  40                  45

Ala Gly Ala Leu Val Leu Ala Asp Ala Gly Leu Cys Cys Ile Asp Glu
    50                  55                  60
```

```
Phe Asn
65


<210> SEQ ID NO 25
<211> LENGTH: 453
<212> TYPE: DNA
<213> ORGANISM: Mus musculus
<220> FEATURE:
<221> NAME/KEY: CDS
<222> LOCATION: (4)..(453)

<400> SEQUENCE: 25

aat gaa ata ttg gcc agc ttg tgt cct caa gtt ttt ggg atg tat cta       48
    Glu Ile Leu Ala Ser Leu Cys Pro Gln Val Phe Gly Met Tyr Leu
    1               5                   10                  15

gtg aag ctt gct gtg gcc atg gta ctg gct ggt gga att caa aga act       96
Val Lys Leu Ala Val Ala Met Val Leu Ala Gly Gly Ile Gln Arg Thr
                20                  25                  30

gat gct gca gga acc agg gtt aga ggg gaa tct cac ctt tta ttg gtt      144
Asp Ala Ala Gly Thr Arg Val Arg Gly Glu Ser His Leu Leu Leu Val
            35                  40                  45

ggg gat cct ggc aca ggg aaa tca caa ttc ctt aaa tat gca gca aag      192
Gly Asp Pro Gly Thr Gly Lys Ser Gln Phe Leu Lys Tyr Ala Ala Lys
        50                  55                  60

att acc cca agg tcc gtt ttg acc aca gga att gga tct act agt gca      240
Ile Thr Pro Arg Ser Val Leu Thr Thr Gly Ile Gly Ser Thr Ser Ala
    65                  70                  75

ggt ctg acc gtg aca gct gtc aaa gac tca gga gaa tgg aat cta gag      288
Gly Leu Thr Val Thr Ala Val Lys Asp Ser Gly Glu Trp Asn Leu Glu
80                  85                  90                  95

gct ggg gct ttg gtg ctt gca gat gct ggt ctc tgc tgt att gac gaa      336
Ala Gly Ala Leu Val Leu Ala Asp Ala Gly Leu Cys Cys Ile Asp Glu
                100                 105                 110

ttt aac agc ctc aaa gaa cat gac agg aca agc atc cat gaa gca atg      384
Phe Asn Ser Leu Lys Glu His Asp Arg Thr Ser Ile His Glu Ala Met
            115                 120                 125

gag caa caa acc ata agt gtt gct aag gct ggc ctt gtt tgt aag ctg      432
Glu Gln Gln Thr Ile Ser Val Ala Lys Ala Gly Leu Val Cys Lys Leu
        130                 135                 140

aac aca agg acc acc atc ctg                                          453
Asn Thr Arg Thr Thr Ile Leu
    145                 150


<210> SEQ ID NO 26
<211> LENGTH: 150
<212> TYPE: PRT
<213> ORGANISM: Mus musculus

<400> SEQUENCE: 26

Glu Ile Leu Ala Ser Leu Cys Pro Gln Val Phe Gly Met Tyr Leu Val
1               5                   10                  15

Lys Leu Ala Val Ala Met Val Leu Ala Gly Gly Ile Gln Arg Thr Asp
            20                  25                  30

Ala Ala Gly Thr Arg Val Arg Gly Glu Ser His Leu Leu Leu Val Gly
        35                  40                  45

Asp Pro Gly Thr Gly Lys Ser Gln Phe Leu Lys Tyr Ala Ala Lys Ile
    50                  55                  60

Thr Pro Arg Ser Val Leu Thr Thr Gly Ile Gly Ser Thr Ser Ala Gly
65                  70                  75                  80

Leu Thr Val Thr Ala Val Lys Asp Ser Gly Glu Trp Asn Leu Glu Ala
```

```
                85                  90                  95

Gly Ala Leu Val Leu Ala Asp Ala Gly Leu Cys Cys Ile Asp Glu Phe
            100                 105                 110

Asn Ser Leu Lys Glu His Asp Arg Thr Ser Ile His Glu Ala Met Glu
        115                 120                 125

Gln Gln Thr Ile Ser Val Ala Lys Ala Gly Leu Val Cys Lys Leu Asn
    130                 135                 140

Thr Arg Thr Thr Ile Leu
145                 150


<210> SEQ ID NO 27
<211> LENGTH: 363
<212> TYPE: DNA
<213> ORGANISM: Mus musculus
<220> FEATURE:
<221> NAME/KEY: CDS
<222> LOCATION: (1)..(363)

<400> SEQUENCE: 27

gtt ttt ggg atg tat cta gtg aag ctt gct gtg gcc atg gta ctg gct       48
Val Phe Gly Met Tyr Leu Val Lys Leu Ala Val Ala Met Val Leu Ala
1               5                   10                  15

ggt gga att caa aga act gat gct gca gga acc agg gtt aga ggg gaa       96
Gly Gly Ile Gln Arg Thr Asp Ala Ala Gly Thr Arg Val Arg Gly Glu
            20                  25                  30

tct cac ctt tta ttg gtt ggg gat cct ggc aca ggg aaa tca caa ttc      144
Ser His Leu Leu Leu Val Gly Asp Pro Gly Thr Gly Lys Ser Gln Phe
        35                  40                  45

ctt aaa tat gca gca aag att acc cca agg tcc gtt ttg acc aca gga      192
Leu Lys Tyr Ala Ala Lys Ile Thr Pro Arg Ser Val Leu Thr Thr Gly
    50                  55                  60

att gga tct act agt gca ggt ctg acc gtg aca gct gtc aaa gac tca      240
Ile Gly Ser Thr Ser Ala Gly Leu Thr Val Thr Ala Val Lys Asp Ser
65                  70                  75                  80

gga gaa tgg aat cta gag gct ggg gct ttg gtg ctt gca gat gct ggt      288
Gly Glu Trp Asn Leu Glu Ala Gly Ala Leu Val Leu Ala Asp Ala Gly
                85                  90                  95

ctc tgc tgt att gac gaa ttt aac agc ctc aaa gaa cat gac agg aca      336
Leu Cys Cys Ile Asp Glu Phe Asn Ser Leu Lys Glu His Asp Arg Thr
            100                 105                 110

agc atc cat gaa gca atg gag caa caa                                  363
Ser Ile His Glu Ala Met Glu Gln Gln
        115                 120


<210> SEQ ID NO 28
<211> LENGTH: 121
<212> TYPE: PRT
<213> ORGANISM: Mus musculus

<400> SEQUENCE: 28

Val Phe Gly Met Tyr Leu Val Lys Leu Ala Val Ala Met Val Leu Ala
1               5                   10                  15

Gly Gly Ile Gln Arg Thr Asp Ala Ala Gly Thr Arg Val Arg Gly Glu
            20                  25                  30

Ser His Leu Leu Leu Val Gly Asp Pro Gly Thr Gly Lys Ser Gln Phe
        35                  40                  45

Leu Lys Tyr Ala Ala Lys Ile Thr Pro Arg Ser Val Leu Thr Thr Gly
    50                  55                  60

Ile Gly Ser Thr Ser Ala Gly Leu Thr Val Thr Ala Val Lys Asp Ser
65                  70                  75                  80
```

```
Gly Glu Trp Asn Leu Glu Ala Gly Ala Leu Val Leu Ala Asp Ala Gly
                85                  90                  95

Leu Cys Cys Ile Asp Glu Phe Asn Ser Leu Lys Glu His Asp Arg Thr
            100                 105                 110

Ser Ile His Glu Ala Met Glu Gln Gln
        115                 120


<210> SEQ ID NO 29
<211> LENGTH: 198
<212> TYPE: DNA
<213> ORGANISM: Mus musculus
<220> FEATURE:
<221> NAME/KEY: CDS
<222> LOCATION: (1)..(198)

<400> SEQUENCE: 29

ggg gat cct ggc aca ggg aaa tca caa ttc ctt aaa tat gca gca aag       48
Gly Asp Pro Gly Thr Gly Lys Ser Gln Phe Leu Lys Tyr Ala Ala Lys
1               5                   10                  15

att acc cca agg tcc gtt ttg acc aca gga att gga tct act agt gca       96
Ile Thr Pro Arg Ser Val Leu Thr Thr Gly Ile Gly Ser Thr Ser Ala
            20                  25                  30

ggt ctg acc gtg aca gct gtc aaa gac tca gga gaa tgg aat cta gag      144
Gly Leu Thr Val Thr Ala Val Lys Asp Ser Gly Glu Trp Asn Leu Glu
        35                  40                  45

gct ggg gct ttg gtg ctt gca gat gct ggt ctc tgc tgt att gac gaa      192
Ala Gly Ala Leu Val Leu Ala Asp Ala Gly Leu Cys Cys Ile Asp Glu
    50                  55                  60

ttt aac                                                              198
Phe Asn
65


<210> SEQ ID NO 30
<211> LENGTH: 66
<212> TYPE: PRT
<213> ORGANISM: Mus musculus

<400> SEQUENCE: 30

Gly Asp Pro Gly Thr Gly Lys Ser Gln Phe Leu Lys Tyr Ala Ala Lys
1               5                   10                  15

Ile Thr Pro Arg Ser Val Leu Thr Thr Gly Ile Gly Ser Thr Ser Ala
            20                  25                  30

Gly Leu Thr Val Thr Ala Val Lys Asp Ser Gly Glu Trp Asn Leu Glu
        35                  40                  45

Ala Gly Ala Leu Val Leu Ala Asp Ala Gly Leu Cys Cys Ile Asp Glu
    50                  55                  60

Phe Asn
65


<210> SEQ ID NO 31
<211> LENGTH: 453
<212> TYPE: DNA
<213> ORGANISM: Xenopus sp.
<220> FEATURE:
<221> NAME/KEY: CDS
<222> LOCATION: (1)..(453)

<400> SEQUENCE: 31

cct tta gaa ggt agg aat gaa att ctg gcc agc ctg tgt ccg cag gta       48
Pro Leu Glu Gly Arg Asn Glu Ile Leu Ala Ser Leu Cys Pro Gln Val
1               5                   10                  15
```

```
ttt ggt atg ttt gta gtg aag ctg gca gtg gcc atg gtg ctg gct ggt       96
Phe Gly Met Phe Val Val Lys Leu Ala Val Ala Met Val Leu Ala Gly
            20                  25                  30

gga gtt cag aga att gat tct gct gga aca aga gtg aga ggt gag tca      144
Gly Val Gln Arg Ile Asp Ser Ala Gly Thr Arg Val Arg Gly Glu Ser
        35                  40                  45

cat ctt ctg cta gtt gga gac cct ggc acg ggg aaa tca cag ttt ctg      192
His Leu Leu Leu Val Gly Asp Pro Gly Thr Gly Lys Ser Gln Phe Leu
    50                  55                  60

aag tat gct gca aaa att act ccg agg tct gtc ctt act gca ggc att      240
Lys Tyr Ala Ala Lys Ile Thr Pro Arg Ser Val Leu Thr Ala Gly Ile
65                  70                  75                  80

gga tct act agt gca ggc ttg act gtt act gca gtg aaa gac tct gga      288
Gly Ser Thr Ser Ala Gly Leu Thr Val Thr Ala Val Lys Asp Ser Gly
                85                  90                  95

gag tgg aat ctg gag gct gga gcc ttg gtg tta gct gat gga ggc ctg      336
Glu Trp Asn Leu Glu Ala Gly Ala Leu Val Leu Ala Asp Gly Gly Leu
            100                 105                 110

tgc tgc att gat gaa ttt aat agc atc aag gag cat gac aga acc agc      384
Cys Cys Ile Asp Glu Phe Asn Ser Ile Lys Glu His Asp Arg Thr Ser
        115                 120                 125

atc cat gag gca atg gag cag cag acc atc agt gtt gca aag gct ggg      432
Ile His Glu Ala Met Glu Gln Gln Thr Ile Ser Val Ala Lys Ala Gly
    130                 135                 140

tta gtg tgc aag ctg aac act                                          453
Leu Val Cys Lys Leu Asn Thr
145                 150


<210> SEQ ID NO 32
<211> LENGTH: 151
<212> TYPE: PRT
<213> ORGANISM: Xenopus sp.

<400> SEQUENCE: 32

Pro Leu Glu Gly Arg Asn Glu Ile Leu Ala Ser Leu Cys Pro Gln Val
1               5                   10                  15

Phe Gly Met Phe Val Val Lys Leu Ala Val Ala Met Val Leu Ala Gly
            20                  25                  30

Gly Val Gln Arg Ile Asp Ser Ala Gly Thr Arg Val Arg Gly Glu Ser
        35                  40                  45

His Leu Leu Leu Val Gly Asp Pro Gly Thr Gly Lys Ser Gln Phe Leu
    50                  55                  60

Lys Tyr Ala Ala Lys Ile Thr Pro Arg Ser Val Leu Thr Ala Gly Ile
65                  70                  75                  80

Gly Ser Thr Ser Ala Gly Leu Thr Val Thr Ala Val Lys Asp Ser Gly
                85                  90                  95

Glu Trp Asn Leu Glu Ala Gly Ala Leu Val Leu Ala Asp Gly Gly Leu
            100                 105                 110

Cys Cys Ile Asp Glu Phe Asn Ser Ile Lys Glu His Asp Arg Thr Ser
        115                 120                 125

Ile His Glu Ala Met Glu Gln Gln Thr Ile Ser Val Ala Lys Ala Gly
    130                 135                 140

Leu Val Cys Lys Leu Asn Thr
145                 150


<210> SEQ ID NO 33
<211> LENGTH: 363
<212> TYPE: DNA
<213> ORGANISM: Xenopus sp.
```

```
<220> FEATURE:
<221> NAME/KEY: CDS
<222> LOCATION: (1)..(363)

<400> SEQUENCE: 33

agc ctg tgt ccg cag gta ttt ggt atg ttt gta gtg aag ctg gca gtg        48
Ser Leu Cys Pro Gln Val Phe Gly Met Phe Val Val Lys Leu Ala Val
1               5                   10                  15

gcc atg gtg ctg gct ggt gga gtt cag aga att gat tct gct gga aca        96
Ala Met Val Leu Ala Gly Gly Val Gln Arg Ile Asp Ser Ala Gly Thr
            20                  25                  30

aga gtg aga ggt gag tca cat ctt ctg cta gtt gga gac cct ggc acg       144
Arg Val Arg Gly Glu Ser His Leu Leu Leu Val Gly Asp Pro Gly Thr
        35                  40                  45

ggg aaa tca cag ttt ctg aag tat gct gca aaa att act ccg agg tct       192
Gly Lys Ser Gln Phe Leu Lys Tyr Ala Ala Lys Ile Thr Pro Arg Ser
    50                  55                  60

gtc ctt act gca ggc att gga tct act agt gca ggc ttg act gtt act       240
Val Leu Thr Ala Gly Ile Gly Ser Thr Ser Ala Gly Leu Thr Val Thr
65                  70                  75                  80

gca gtg aaa gac tct gga gag tgg aat ctg gag gct gga gcc ttg gtg       288
Ala Val Lys Asp Ser Gly Glu Trp Asn Leu Glu Ala Gly Ala Leu Val
                85                  90                  95

tta gct gat gga ggc ctg tgc tgc att gat gaa ttt aat agc atc aag       336
Leu Ala Asp Gly Gly Leu Cys Cys Ile Asp Glu Phe Asn Ser Ile Lys
            100                 105                 110

gag cat gac aga acc agc atc cat gag                                   363
Glu His Asp Arg Thr Ser Ile His Glu
        115                 120


<210> SEQ ID NO 34
<211> LENGTH: 121
<212> TYPE: PRT
<213> ORGANISM: Xenopus sp.

<400> SEQUENCE: 34

Ser Leu Cys Pro Gln Val Phe Gly Met Phe Val Val Lys Leu Ala Val
1               5                   10                  15

Ala Met Val Leu Ala Gly Gly Val Gln Arg Ile Asp Ser Ala Gly Thr
            20                  25                  30

Arg Val Arg Gly Glu Ser His Leu Leu Leu Val Gly Asp Pro Gly Thr
        35                  40                  45

Gly Lys Ser Gln Phe Leu Lys Tyr Ala Ala Lys Ile Thr Pro Arg Ser
    50                  55                  60

Val Leu Thr Ala Gly Ile Gly Ser Thr Ser Ala Gly Leu Thr Val Thr
65                  70                  75                  80

Ala Val Lys Asp Ser Gly Glu Trp Asn Leu Glu Ala Gly Ala Leu Val
                85                  90                  95

Leu Ala Asp Gly Gly Leu Cys Cys Ile Asp Glu Phe Asn Ser Ile Lys
            100                 105                 110

Glu His Asp Arg Thr Ser Ile His Glu
        115                 120


<210> SEQ ID NO 35
<211> LENGTH: 198
<212> TYPE: DNA
<213> ORGANISM: Xenopus sp.
<220> FEATURE:
<221> NAME/KEY: CDS
<222> LOCATION: (1)..(198)
```

<400> SEQUENCE: 35

```
gga gac cct ggc acg ggg aaa tca cag ttt ctg aag tat gct gca aaa       48
Gly Asp Pro Gly Thr Gly Lys Ser Gln Phe Leu Lys Tyr Ala Ala Lys
1               5                   10                  15

att act ccg agg tct gtc ctt act gca ggc att gga tct act agt gca       96
Ile Thr Pro Arg Ser Val Leu Thr Ala Gly Ile Gly Ser Thr Ser Ala
            20                  25                  30

ggc ttg act gtt act gca gtg aaa gac tct gga gag tgg aat ctg gag      144
Gly Leu Thr Val Thr Ala Val Lys Asp Ser Gly Glu Trp Asn Leu Glu
        35                  40                  45

gct gga gcc ttg gtg tta gct gat gga ggc ctg tgc tgc att gat gaa      192
Ala Gly Ala Leu Val Leu Ala Asp Gly Gly Leu Cys Cys Ile Asp Glu
    50                  55                  60

ttt aat                                                              198
Phe Asn
65
```

<210> SEQ ID NO 36
<211> LENGTH: 66
<212> TYPE: PRT
<213> ORGANISM: Xenopus sp.

<400> SEQUENCE: 36

```
Gly Asp Pro Gly Thr Gly Lys Ser Gln Phe Leu Lys Tyr Ala Ala Lys
1               5                   10                  15

Ile Thr Pro Arg Ser Val Leu Thr Ala Gly Ile Gly Ser Thr Ser Ala
            20                  25                  30

Gly Leu Thr Val Thr Ala Val Lys Asp Ser Gly Glu Trp Asn Leu Glu
        35                  40                  45

Ala Gly Ala Leu Val Leu Ala Asp Gly Gly Leu Cys Cys Ile Asp Glu
    50                  55                  60

Phe Asn
65
```

<210> SEQ ID NO 37
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 37

```
ggg gat cct ggc aca ggg aaa tct                                       24
Gly Asp Pro Gly Thr Gly Lys Ser
1               5
```

<210> SEQ ID NO 38
<211> LENGTH: 8
<212> TYPE: PRT
<213> ORGANISM: Homo sapiens

<400> SEQUENCE: 38

```
Gly Asp Pro Gly Thr Gly Lys Ser
1               5
```

<210> SEQ ID NO 39
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 39

```
gat gag ttc aat                                                   12
Asp Glu Phe Asn
1
```

<210> SEQ ID NO 40
<211> LENGTH: 4
<212> TYPE: PRT
<213> ORGANISM: Homo sapiens

<400> SEQUENCE: 40

```
Asp Glu Phe Asn
1
```

<210> SEQ ID NO 41
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 41

```
ggg gat cct ggc aca ggg aaa tca                                   24
Gly Asp Pro Gly Thr Gly Lys Ser
1               5
```

<210> SEQ ID NO 42
<211> LENGTH: 8
<212> TYPE: PRT
<213> ORGANISM: Mus musculus

<400> SEQUENCE: 42

```
Gly Asp Pro Gly Thr Gly Lys Ser
1               5
```

<210> SEQ ID NO 43
<211> LENGTH: 12
<212> TYPE: DNA
<213> ORGANISM: Mus musculus
<220> FEATURE:
<221> NAME/KEY: CDS
<222> LOCATION: (1)..(12)

<400> SEQUENCE: 43

```
gac gaa ttt aac                                                   12
Asp Glu Phe Asn
1
```

<210> SEQ ID NO 44
<211> LENGTH: 4
<212> TYPE: PRT
<213> ORGANISM: Mus musculus

<400> SEQUENCE: 44

```
Asp Glu Phe Asn
1
```

<210> SEQ ID NO 45
<211> LENGTH: 24
<212> TYPE: DNA
<213> ORGANISM: Xenopus sp.
<220> FEATURE:
<221> NAME/KEY: CDS
<222> LOCATION: (1)..(24)

<400> SEQUENCE: 45

```
gga gac cct ggc acg ggg aaa tca                                        24
Gly Asp Pro Gly Thr Gly Lys Ser
1               5
```

<210> SEQ ID NO 46
<211> LENGTH: 8
<212> TYPE: PRT
<213> ORGANISM: Xenopus sp.

<400> SEQUENCE: 46

```
Gly Asp Pro Gly Thr Gly Lys Ser
1               5
```

<210> SEQ ID NO 47
<211> LENGTH: 12
<212> TYPE: DNA
<213> ORGANISM: Xenopus sp.
<220> FEATURE:
<221> NAME/KEY: CDS
<222> LOCATION: (1)..(12)

<400> SEQUENCE: 47

```
gat gaa ttt aat                                                        12
Asp Glu Phe Asn
1
```

<210> SEQ ID NO 48
<211> LENGTH: 4
<212> TYPE: PRT
<213> ORGANISM: Xenopus sp.

<400> SEQUENCE: 48

```
Asp Glu Phe Asn
1
```

<210> SEQ ID NO 49
<211> LENGTH: 624
<212> TYPE: PRT
<213> ORGANISM: Homo sapiens

<400> SEQUENCE: 49

```
Met Asn Ser Asp Gln Val Thr Leu Val Gly Gln Val Phe Glu Ser Tyr
1               5                   10                  15

Val Ser Glu Tyr His Lys Asn Asp Ile Leu Leu Ile Leu Lys Glu Arg
            20                  25                  30

Asp Glu Asp Ala His Tyr Pro Val Val Val Asn Ala Met Thr Leu Phe
        35                  40                  45

Glu Thr Asn Met Glu Ile Gly Glu Tyr Phe Asn Met Phe Pro Ser Glu
    50                  55                  60

Val Leu Thr Ile Phe Asp Ser Ala Leu Arg Arg Ser Ala Leu Thr Ile
65                  70                  75                  80

Leu Gln Ser Leu Ser Gln Pro Glu Ala Val Ser Met Lys Gln Asn Leu
                85                  90                  95

His Ala Arg Ile Ser Gly Leu Pro Val Cys Pro Glu Leu Val Arg Glu
            100                 105                 110

His Ile Pro Lys Thr Lys Asp Val Gly His Phe Leu Ser Val Thr Gly
        115                 120                 125

Thr Val Ile Arg Thr Ser Leu Val Lys Val Leu Glu Phe Glu Arg Asp
    130                 135                 140

Tyr Met Cys Asn Lys Cys Lys His Val Phe Val Ile Lys Ala Asp Phe
```

```
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
            180                 185                 190

Pro Thr Arg Cys Arg Asp Tyr Gln Glu Ile Lys Ile Gln Glu Gln Val
        195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240

Tyr Gly Ile Val Met Gln Arg Trp Lys Pro Phe Gln Gln Asp Val Arg
                245                 250                 255

Cys Glu Val Glu Ile Val Leu Lys Ala Asn Tyr Ile Gln Val Asn Asn
            260                 265                 270

Glu Gln Ser Ser Gly Ile Ile Met Asp Glu Glu Val Gln Lys Glu Phe
        275                 280                 285

Glu Asp Phe Trp Glu Tyr Tyr Lys Ser Asp Pro Phe Ala Gly Arg Asn
    290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                325                 330                 335

Ala Thr Gly Thr Arg Val Arg Gly Glu Ser His Leu Leu Leu Val Gly
            340                 345                 350

Asp Pro Gly Thr Gly Lys Ser Gln Phe Leu Lys Tyr Ala Ala Lys Ile
        355                 360                 365

Thr Pro Arg Ser Val Leu Thr Thr Gly Ile Gly Ser Thr Ser Ala Gly
    370                 375                 380

Leu Thr Val Thr Ala Val Lys Asp Ser Gly Glu Trp Asn Leu Glu Ala
385                 390                 395                 400

Gly Ala Leu Val Leu Ala Asp Ala Gly Leu Cys Cys Ile Asp Glu Phe
                405                 410                 415

Asn Ser Leu Lys Glu His Asp Arg Thr Ser Ile His Glu Ala Met Glu
            420                 425                 430

Gln Gln Thr Ile Ser Val Ala Lys Ala Gly Leu Val Cys Lys Leu Asn
        435                 440                 445

Thr Arg Thr Thr Ile Leu Ala Ala Thr Asn Pro Lys Gly Gln Tyr Asp
    450                 455                 460

Pro Gln Glu Ser Val Ser Val Asn Ile Ala Leu Gly Ser Pro Leu Leu
465                 470                 475                 480

Ser Arg Phe Asp Leu Ile Leu Val Leu Leu Asp Thr Lys Asn Glu Asp
                485                 490                 495

Trp Asp Arg Ile Ile Ser Ser Phe Ile Leu Glu Asn Lys Gly Tyr Pro
            500                 505                 510

Ser Lys Ser Glu Lys Leu Trp Ser Met Glu Lys Met Lys Thr Tyr Phe
        515                 520                 525

Cys Leu Ile Arg Asn Leu Gln Pro Thr Leu Ser Asp Val Gly Asn Gln
    530                 535                 540

Val Leu Leu Arg Tyr Tyr Gln Met Gln Arg Gln Ser Asp Cys Arg Asn
545                 550                 555                 560

Ala Ala Arg Thr Thr Ile Arg Leu Leu Glu Ser Leu Ile Arg Leu Ala
                565                 570                 575
```

```
Glu Ala His Ala Arg Leu Met Phe Arg Asp Thr Val Thr Leu Glu Asp
            580                 585                 590

Ala Ile Thr Val Val Ser Val Met Glu Ser Ser Met Gln Gly Gly Ala
        595                 600                 605

Leu Leu Gly Gly Val Asn Ala Leu His Thr Ser Phe Pro Glu Asn Pro
    610                 615                 620


<210> SEQ ID NO 50
<211> LENGTH: 780
<212> TYPE: PRT
<213> ORGANISM: Mus musculus

<400> SEQUENCE: 50

Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
            20                  25                  30

Arg Leu Val Arg Pro Lys Pro Arg Leu Gln Leu Pro Glu Ser Arg Leu
        35                  40                  45

Ser Pro Cys Ser Arg Leu Pro Leu Ala Asp Ser Ser Val Arg Pro Gly
    50                  55                  60

Ala Arg Pro Pro Ala Ser Ala Pro Gly Arg Ser Pro Ser Gly Arg Lys
65                  70                  75                  80

Val Glu Ala Val Arg Gly Ser Gly Ser Ala Gly Ser Ser Ser Pro Ser
                85                  90                  95

Glu Ala Glu Arg Glu Gln Arg Glu Glu Ala Cys Ala Pro Pro Arg Lys
            100                 105                 110

Ala Ala Pro Ser Ser Gly Arg Ala His Ala Pro Pro Pro Pro Thr Pro
        115                 120                 125

Arg Gly Ser Gly Trp Gly Asp His Gly Arg Ser Ala Val Pro Ala Thr
    130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
                165                 170                 175

His Lys Asn Asp Ile Leu Leu Ile Leu Lys Glu Arg Asp Glu Asp Ala
            180                 185                 190

His Tyr Pro Val Val Val Asn Ala Met Ser Leu Phe Glu Thr Asn Met
        195                 200                 205

Glu Ile Gly Asp Tyr Phe Thr Val Phe Pro Asn Glu Val Leu Thr Val
    210                 215                 220

Phe Asp Ser Ala Leu Arg Arg Ser Ala Leu Ala Ile Leu Gln Ser Leu
225                 230                 235                 240

Pro Glu Thr Glu Gly Leu Ser Met Lys Gln Asn Leu His Ala Arg Ile
                245                 250                 255

Ser Gly Leu Pro Val Cys Pro Glu Leu Val Arg Glu His Ile Pro Lys
            260                 265                 270

Thr Lys Asp Val Gly His Phe Leu Ser Val Thr Gly Thr Val Ile Arg
        275                 280                 285

Thr Ser Leu Val Lys Val Leu Glu Phe Glu Arg Asp Tyr Met Cys Asn
    290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
```

```
                325                 330                 335

Ser Lys Phe Ser Cys Leu Ser Asp Leu Ser Ser Ser Pro Ala Arg Cys
            340                 345                 350

Arg Asp Tyr Gln Glu Ile Lys Ile Gln Glu Gln Val Gln Arg Leu Ser
        355                 360                 365

Val Gly Ser Ile Pro Arg Ser Met Lys Val Ile Leu Glu Asp Asp Leu
    370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
                405                 410                 415

Ile Val Leu Lys Ala Asn Tyr Val Gln Val Asn Asn Glu Gln Ser Ser
            420                 425                 430

Gly Met Val Met Asp Glu Asp Thr Arg Lys Glu Phe Glu Asp Phe Trp
        435                 440                 445

Glu His Tyr Lys Ser Asp Pro Phe Ala Gly Arg Asn Glu Ile Leu Ala
    450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala Gly Leu Thr Val Thr
    530                 535                 540

Ala Val Lys Asp Ser Gly Glu Trp Asn Leu Glu Ala Gly Ala Leu Val
545                 550                 555                 560

Leu Ala Asp Ala Gly Leu Cys Cys Ile Asp Glu Phe Asn Ser Leu Lys
                565                 570                 575

Glu His Asp Arg Thr Ser Ile His Glu Ala Met Glu Gln Gln Thr Ile
            580                 585                 590

Ser Val Ala Lys Ala Gly Leu Val Cys Lys Leu Asn Thr Arg Thr Thr
        595                 600                 605

Ile Leu Ala Ala Thr Asn Pro Lys Gly Gln Tyr Asp Pro Lys Glu Ser
    610                 615                 620

Val Ser Val Asn Ile Ala Leu Gly Ser Pro Leu Leu Ser Arg Phe Asp
625                 630                 635                 640

Leu Val Leu Val Leu Leu Asp Thr Arg Asn Glu Asp Trp Asp Arg Ile
                645                 650                 655

Ile Ser Ser Phe Ile Leu Glu Asn Lys Gly Tyr Pro Ser Lys Ser Glu
            660                 665                 670

Asn Leu Trp Ser Met Glu Lys Met Lys Thr Tyr Phe Cys Leu Ile Arg
        675                 680                 685

Asn Leu His Pro Thr Leu Ser Glu Val Ser Asn Gln Val Leu Leu Arg
    690                 695                 700

Tyr Tyr Gln Met Gln Arg Gln Ser Asp Ser Arg Asn Ala Ala Arg Thr
705                 710                 715                 720

Thr Ile Arg Leu Leu Glu Ser Leu Ile Arg Leu Ala Glu Ala His Ala
                725                 730                 735

Arg Leu Met Phe Arg Ser Ala Val Thr Leu Glu Asp Ala Val Thr Ala
            740                 745                 750
```

```
Val Ser Val Met Glu Ser Ser Met Gln Gly Gly Ala Leu Leu Gly Gly
        755                 760                 765

Val Asn Ala Leu His Thr Ser Phe Pro Glu Asn Pro
    770                 775                 780


<210> SEQ ID NO 51
<211> LENGTH: 626
<212> TYPE: PRT
<213> ORGANISM: Gallus gallus

<400> SEQUENCE: 51

Met Ala Leu Arg Ala Asp Gln Val Ser Leu Ile Gly Gln Val Phe Glu
1               5                   10                  15

Ser Tyr Leu Leu Gln His His Arg Asp Asp Ile Leu Gly Ile Leu Arg
            20                  25                  30

Gln Gly Asp Asp Glu Ala His Tyr Pro Val Leu Val Asp Ala Leu Thr
        35                  40                  45

Leu Phe Glu Thr Asn Met Glu Ile Gly Glu Tyr Phe Asn Ala Phe Pro
    50                  55                  60

Ser Gln Val Leu Pro Ile Phe Asp Gly Ala Leu Arg Arg Ala Ala Met
65                  70                  75                  80

Ala Val Leu Gln Ala Ala Thr Pro Ser Pro Glu Leu Arg Met Lys Pro
                85                  90                  95

Asn Leu His Ala Arg Ile Ser Gly Leu Pro Ile Cys Pro Glu Leu Thr
            100                 105                 110

Arg Glu His Ile Pro Lys Thr Arg Asp Val Gly His Phe Leu Ser Val
        115                 120                 125

Thr Gly Thr Val Ile Arg Thr Ser Leu Val Lys Val Leu Glu Phe Glu
    130                 135                 140

Arg Ser Tyr Ile Cys Asn Lys Cys Lys His Val Phe Val Ala Lys Ala
145                 150                 155                 160

Asp Phe Glu Gln Tyr Tyr Ala Phe Cys Arg Pro Ser Ala Cys Leu Asn
                165                 170                 175

Glu Glu Gly Cys Asn Ser Thr Lys Phe Thr Cys Leu Ser Gly Thr Ser
            180                 185                 190

Ser Ser Pro Ser Ser Cys Arg Asp Tyr Gln Glu Ile Lys Ile Gln Glu
        195                 200                 205

Gln Val Gln Arg Leu Ser Val Gly Ser Ile Pro Arg Cys Met Val Val
    210                 215                 220

Val Leu Glu Asp Asp Leu Val Asp Ser Cys Lys Ser Gly Asp Asp Ile
225                 230                 235                 240

Thr Val Tyr Gly Val Val Met Gln Arg Trp Lys Pro Phe His Gln Asp
                245                 250                 255

Ala Arg Cys Asp Leu Glu Leu Val Leu Lys Ala Asn Tyr Val Lys Val
            260                 265                 270

Asn Asn Glu Gln Leu Ala Gly Val Thr Ile Asp Glu Glu Val Arg Lys
        275                 280                 285

Glu Phe Glu Asp Phe Trp Glu Lys His Arg Asn Asn Pro Leu Ala Gly
    290                 295                 300

Arg Asn Glu Ile Leu Ala Ser Leu Cys Pro Gln Val Phe Gly Leu Tyr
305                 310                 315                 320

Leu Val Lys Leu Ala Val Ala Met Val Leu Ala Gly Gly Val Gln Arg
                325                 330                 335

Ile Asp Ala Thr Gly Thr Arg Ile Arg Gly Glu Ser His Leu Leu Leu
```

```
            340                 345                 350

Val Gly Asp Pro Gly Thr Gly Lys Ser Gln Phe Leu Lys Tyr Ala Val
        355                 360                 365

Lys Ile Thr Pro Arg Ser Val Leu Thr Ala Gly Ile Gly Ser Thr Ser
    370                 375                 380

Ala Gly Leu Thr Val Thr Ala Val Lys Asp Phe Gly Glu Trp Asn Leu
385                 390                 395                 400

Glu Ala Gly Ala Leu Val Leu Ala Asp Gly Gly Leu Cys Cys Ile Asp
                405                 410                 415

Glu Phe Asn Ser Ile Lys Glu His Asp Arg Thr Ser Ile His Glu Ala
            420                 425                 430

Met Glu Gln Gln Thr Ile Ser Val Ala Lys Ala Gly Leu Val Cys Lys
        435                 440                 445

Leu Asn Thr Arg Thr Thr Ile Leu Ala Ala Thr Asn Pro Lys Gly His
    450                 455                 460

Tyr Asp Pro Ala Glu Ser Val Ser Val Asn Ile Ala Leu Gly Ser Pro
465                 470                 475                 480

Leu Leu Ser Arg Phe Asp Leu Val Leu Val Leu Leu Asp Thr Lys Asn
                485                 490                 495

Glu Glu Trp Asp Arg Ile Ile Ser Ser Phe Ile Leu Gln Asn Lys Gly
            500                 505                 510

Cys Pro Ser Lys Ser Glu Lys Leu Trp Ser Met Glu Lys Met Lys Thr
        515                 520                 525

Tyr Phe Cys Leu Ile Lys Arg Ile Gln Pro Lys Leu Ser Asp Glu Ser
    530                 535                 540

Asn Leu Ile Leu Val Arg Tyr Tyr Gln Met Gln Arg Gln Ser Asp Cys
545                 550                 555                 560

Arg Asn Ala Ala Arg Thr Thr Ile Arg Leu Leu Glu Ser Leu Ile Arg
                565                 570                 575

Leu Ala Glu Ala His Ala Arg Leu Met Phe Arg Asp Thr Val Thr Leu
            580                 585                 590

Glu Asp Ala Val Thr Val Val Ser Val Met Glu Ser Ser Met Gln Gly
        595                 600                 605

Gly Ala Leu Leu Gly Ala Ile Asn Ala Leu His Thr Ser Phe Pro Glu
    610                 615                 620

Asn Pro
625


<210> SEQ ID NO 52
<211> LENGTH: 625
<212> TYPE: PRT
<213> ORGANISM: Xenopus sp.

<400> SEQUENCE: 52

Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
            20                  25                  30

Glu Lys Glu Glu His Ala His Tyr Ser Leu Val Val Asn Ala Met Thr
        35                  40                  45

Leu Phe Glu Ala Asn Met Glu Ile Gly Glu Tyr Phe Asn Ala Phe Pro
    50                  55                  60

Asn Glu Val Leu Pro Val Phe Asp Asn Ala Leu Arg Cys Ala Ala Met
65                  70                  75                  80
```

```
Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125

Thr Gly Thr Val Ile Arg Thr Ser Leu Val Lys Val Leu Glu Tyr Glu
    130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                165                 170                 175

Glu Glu Gly Cys Asn Ser Thr Lys Phe Thr Cys Leu Ser Asp Ser Ser
            180                 185                 190

Ser Pro Ala Ser Cys Arg Asp Tyr Gln Glu Ile Lys Ile Gln Glu Gln
        195                 200                 205

Val Gln Arg Leu Ser Val Gly Ser Ile Pro Arg Ser Met Ile Val Val
    210                 215                 220

Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                245                 250                 255

Arg Cys Asp Leu Glu Ile Val Leu Lys Ala Asn Tyr Ile Ser Val Asn
            260                 265                 270

Asn Glu Gln Pro Cys Gly Val Val Ile Asn Glu Glu Val Arg Lys Glu
        275                 280                 285

Tyr Glu Asp Phe Trp Val Lys Tyr Arg Asn Asn Pro Leu Glu Gly Arg
    290                 295                 300

Asn Glu Ile Leu Ala Ser Leu Cys Pro Gln Val Phe Gly Met Phe Val
305                 310                 315                 320

Val Lys Leu Ala Val Ala Met Val Leu Ala Gly Gly Val Gln Arg Ile
                325                 330                 335

Asp Ser Ala Gly Thr Arg Val Arg Gly Glu Ser His Leu Leu Leu Val
            340                 345                 350

Gly Asp Pro Gly Thr Gly Lys Ser Gln Phe Leu Lys Tyr Ala Ala Lys
        355                 360                 365

Ile Thr Pro Arg Ser Val Leu Thr Ala Gly Ile Gly Ser Thr Ser Ala
    370                 375                 380

Gly Leu Thr Val Thr Ala Val Lys Asp Ser Gly Glu Trp Asn Leu Glu
385                 390                 395                 400

Ala Gly Ala Leu Val Leu Ala Asp Gly Gly Leu Cys Cys Ile Asp Glu
                405                 410                 415

Phe Asn Ser Ile Lys Glu His Asp Arg Thr Ser Ile His Glu Ala Met
            420                 425                 430

Glu Gln Gln Thr Ile Ser Val Ala Lys Ala Gly Leu Val Cys Lys Leu
        435                 440                 445

Asn Thr Arg Thr Thr Ile Leu Ala Ala Thr Asn Pro Lys Gly Gln Tyr
    450                 455                 460

Asp Pro Asp Glu Ser Ile Ser Val Asn Val Ala Leu Ala Ser Pro Leu
465                 470                 475                 480

Leu Ser Arg Phe Asp Leu Val Leu Val Leu Leu Asp Thr Lys Asn Glu
                485                 490                 495

Asp Trp Asp Arg Ile Ile Ser Ser Phe Ile Leu Glu Ser Lys Gly Cys
```

```
            500                 505                 510

Pro Arg Lys Ser Asp Lys Leu Trp Ser Met Glu Lys Met Lys Thr Tyr
        515                 520                 525

Phe Cys Leu Ile Lys Asn Leu Gln Pro Lys Met Ser Gln Asp Ala Asn
    530                 535                 540

Val Ile Leu Val Arg Tyr Tyr Gln Leu Gln Arg Gln Ser Ser Cys Arg
545                 550                 555                 560

Asn Ala Ala Arg Thr Thr Ile Arg Leu Leu Glu Ser Leu Ile Arg Leu
                565                 570                 575

Ala Glu Ala His Ala Arg Ile Met Tyr Arg Asp Val Val Thr Thr Glu
            580                 585                 590

Asp Ala Ile Thr Val Val Ser Ile Met Glu Ser Ser Met Gln Gly Gly
        595                 600                 605

Ala Leu Leu Gly Gly Val Asn Ala Leu His Thr Ser Phe Pro Glu Asn
    610                 615                 620

Pro
625


<210> SEQ ID NO 53
<211> LENGTH: 236
<212> TYPE: PRT
<213> ORGANISM: Xenopus sp.

<400> SEQUENCE: 53

Lys Lys Phe Cys Lys Ala His Ser Lys Asp Ile Phe Glu His Leu Ser
1               5                   10                  15

Lys Ser Leu Ala Pro Ser Ile His Gly His Glu Tyr Ile Lys Lys Ala
            20                  25                  30

Ile Leu Cys Met Leu Leu Gly Gly Asn Glu Lys Val Leu Glu Asn Gly
        35                  40                  45

Thr Arg Ile Arg Gly Asp Ile Asn Val Leu Leu Ile Gly Asp Pro Ser
    50                  55                  60

Val Ala Lys Ser Gln Leu Leu Arg Tyr Val Leu His Thr Ala Pro Arg
65                  70                  75                  80

Ala Ile Pro Thr Thr Gly Arg Gly Ser Ser Gly Val Gly Leu Thr Ala
                85                  90                  95

Ala Val Thr Thr Asp Gln Glu Thr Gly Glu Arg Arg Leu Glu Ala Gly
            100                 105                 110

Ala Met Val Leu Ala Asp Arg Gly Val Val Cys Ile Asp Glu Phe Asp
        115                 120                 125

Lys Met Ser Asp Met Asp Arg Thr Ala Ile His Glu Val Met Glu Gln
    130                 135                 140

Gly Arg Val Thr Ile Ala Lys Ala Gly Ile Gln Ala Arg Leu Asn Ala
145                 150                 155                 160

Arg Cys Ser Val Leu Ala Ala Ala Asn Pro Val Tyr Gly Arg Tyr Asp
                165                 170                 175

Gln Tyr Arg Thr Pro Met Glu Asn Ile Gly Leu Gln Asp Ser Leu Leu
            180                 185                 190

Ser Arg Phe Asp Leu Leu Phe Ile Val Leu Asp Lys Met Asp Ala Asp
        195                 200                 205

Asn Asp Gln Glu Ile Ala Asp His Val Leu Arg Met His Arg Tyr Arg
    210                 215                 220

Thr Pro Gly Glu Gln Asp Gly Tyr Ala Leu Pro Leu
225                 230                 235
```

<210> SEQ ID NO 54
<211> LENGTH: 224
<212> TYPE: PRT
<213> ORGANISM: Xenopus sp.

<400> SEQUENCE: 54

```
Glu Glu Leu Arg Gln Ile Thr Glu Glu Asp Phe Tyr Glu Lys Leu Ala
1               5                   10                  15

Ala Ser Ile Ala Pro Glu Ile Tyr Gly His Glu Asp Val Lys Lys Ala
            20                  25                  30

Leu Leu Leu Leu Leu Val Gly Gly Val Asp Asn Ser Pro Arg Gly Met
        35                  40                  45

Lys Ile Arg Gly Asn Ile Asn Ile Cys Leu Met Gly Asp Pro Gly Val
    50                  55                  60

Ala Lys Ser Gln Leu Leu Ser Tyr Ile Asp Arg Leu Ala Pro Arg Ser
65                  70                  75                  80

Gln Tyr Thr Thr Gly Arg Gly Ser Ser Gly Val Gly Leu Thr Ala Ala
                85                  90                  95

Val Met Lys Asp Pro Val Thr Gly Glu Met Thr Leu Glu Gly Gly Ala
            100                 105                 110

Leu Val Leu Ala Asp Gln Gly Val Cys Cys Ile Asp Glu Phe Asp Lys
        115                 120                 125

Met Met Asp Thr Asp Arg Thr Ala Ile His Glu Val Met Glu Gln Gln
    130                 135                 140

Thr Ile Ser Ile Ala Lys Ala Gly Ile Met Thr Thr Leu Asn Ala Arg
145                 150                 155                 160

Cys Ser Ile Leu Ala Ala Ala Asn Pro Ala Tyr Gly Arg Tyr Asn Pro
                165                 170                 175

Lys Lys Thr Val Glu Gln Asn Ile Gln Leu Pro Ala Ala Leu Leu Ser
            180                 185                 190

Arg Phe Asp Val Leu Trp Leu Ile Gln Asp Lys Pro Asp Arg Asp Asn
        195                 200                 205

Asp Leu Arg Leu Ala Gln His Ile Thr Tyr Val His Gln His Ser Lys
    210                 215                 220
```

<210> SEQ ID NO 55
<211> LENGTH: 226
<212> TYPE: PRT
<213> ORGANISM: Xenopus sp.

<400> SEQUENCE: 55

```
Glu Glu Glu Phe Arg Arg Leu Ala Ala Lys Pro Asp Ile Tyr Glu Thr
1               5                   10                  15

Val Ala Lys Ser Ile Ala Pro Ser Ile Tyr Gly Ser Ser Asp Ile Lys
            20                  25                  30

Lys Ala Ile Ala Cys Leu Leu Phe Gly Gly Ser Arg Lys Arg Leu Pro
        35                  40                  45

Asp Gly Leu Thr Arg Arg Gly Asp Val Asn Leu Leu Met Leu Gly Asp
    50                  55                  60

Pro Gly Thr Ala Lys Ser Gln Leu Leu Lys Phe Val Glu Arg Cys Ser
65                  70                  75                  80

Pro Ile Gly Val Tyr Thr Ser Gly Lys Gly Ser Ser Ala Ala Gly Leu
                85                  90                  95

Thr Ala Ser Val Met Arg Asp Pro Val Ser Arg Asn Phe Ile Met Glu
            100                 105                 110
```

```
Gly Gly Ala Met Val Leu Ala Asp Gly Gly Val Val Cys Ile Asp Glu
        115                 120                 125

Phe Asp Lys Met Arg Glu Asp Asp Arg Val Ala Ile His Glu Ala Met
    130                 135                 140

Glu Gln Gln Thr Ile Ser Ile Ala Lys Ala Gly Ile Thr Thr Thr Leu
145                 150                 155                 160

Asn Ser Arg Cys Ser Val Leu Ala Ala Ala Asn Ser Val Tyr Gly Arg
                165                 170                 175

Trp Asp Asp Thr Lys Gly Glu Glu Asn Ile Asp Phe Met Pro Thr Ile
            180                 185                 190

Leu Ser Arg Phe Asp Met Ile Phe Ile Val Lys Asp Glu His Asn Glu
        195                 200                 205

Gln Arg Asp Met Thr Leu Ala Lys His Val Met Asn Val His Leu Ser
    210                 215                 220

Ala Arg
225


<210> SEQ ID NO 56
<211> LENGTH: 225
<212> TYPE: PRT
<213> ORGANISM: Xenopus sp.

<400> SEQUENCE: 56

Ile Val Ala Leu Ser Lys Asp Glu Arg Ile Gly Glu Arg Ile Phe Ala
1               5                   10                  15

Ser Ile Ala Pro Ser Ile Tyr Gly His Glu Asp Ile Lys Arg Gly Leu
            20                  25                  30

Ala Leu Ala Leu Phe Gly Gly Glu Ala Lys Asn Pro Gly Gly Lys His
        35                  40                  45

Lys Val Arg Gly Asp Ile Asn Val Leu Leu Cys Gly Asp Pro Gly Thr
    50                  55                  60

Ala Lys Ser Gln Phe Leu Lys Tyr Val Glu Lys Val Ala Ser Arg Ala
65                  70                  75                  80

Val Phe Thr Thr Gly Gln Gly Ala Ser Ala Val Gly Leu Thr Ala Tyr
                85                  90                  95

Val Gln Arg His Pro Val Thr Lys Glu Trp Thr Leu Glu Ala Gly Ala
            100                 105                 110

Leu Val Phe Ala Asp Arg Gly Val Cys Leu Ile Asp Glu Phe Asp Lys
        115                 120                 125

Met Asn Asp Gln Asp Arg Thr Ser Ile His Glu Ala Met Glu Gln Gln
    130                 135                 140

Ser Ile Ser Ile Ser Lys Ala Gly Ile Val Thr Ser Leu Gln Ala Arg
145                 150                 155                 160

Cys Thr Val Ile Ala Ala Ser Asn Pro Ile Gly Gly Arg Tyr Asp Pro
                165                 170                 175

Ser Leu Thr Phe Ser Glu Asn Val Asp Leu Thr Glu Pro Ile Val Ser
            180                 185                 190

Arg Phe Asp Ile Leu Cys Val Val Arg Asp Thr Val Asp Pro Val Gln
        195                 200                 205

Asp Glu Met Leu Ala Arg Phe Val Val Ser Ser His Ile Lys His His
    210                 215                 220

Pro
225


<210> SEQ ID NO 57
```

```
<211> LENGTH: 230
<212> TYPE: PRT
<213> ORGANISM: Xenopus sp.

<400> SEQUENCE: 57

Val Glu Lys Ile Gln Gln Val Ser Lys Arg Asp Asp Ile Tyr Asp Ile
1               5                   10                  15

Leu Ser Arg Ser Leu Ala Pro Ser Ile Tyr Glu Met Asp Asp Val Lys
            20                  25                  30

Lys Gly Leu Leu Leu Gln Leu Phe Gly Gly Thr Asn Lys Ser Phe His
        35                  40                  45

Lys Gly Ala Ser Pro Arg Tyr Arg Gly Asp Ile Asn Ile Leu Met Cys
    50                  55                  60

Gly Asp Pro Ser Thr Ser Lys Ser Gln Ile Leu Lys Tyr Val His Lys
65                  70                  75                  80

Ile Ala Pro Arg Gly Val Tyr Thr Ser Gly Lys Gly Ser Ser Ala Val
                85                  90                  95

Gly Leu Thr Ala Tyr Ile Thr Arg Asp Gln Asp Thr Lys Gln Leu Val
            100                 105                 110

Leu Glu Ser Gly Ala Leu Val Leu Ser Asp Gly Gly Ile Cys Cys Ile
        115                 120                 125

Asp Glu Phe Asp Lys Met Ser Asp Ala Thr Arg Ser Ile Leu His Glu
    130                 135                 140

Val Met Glu Gln Gln Thr Val Thr Val Ala Lys Ala Gly Ile Ile Thr
145                 150                 155                 160

Thr Leu Asn Ala Arg Thr Ser Ile Leu Ala Ser Ala Asn Pro Ile Gly
                165                 170                 175

Ser Lys Tyr Asn Pro Asp Leu Pro Val Thr Lys Asn Ile Asp Leu Pro
            180                 185                 190

Pro Thr Leu Leu Ser Arg Phe Asp Leu Val Tyr Leu Ile Leu Asp Arg
        195                 200                 205

Val Asp Glu Thr Leu Asp Arg Lys Leu Ala Asn His Ile Val Ser Met
    210                 215                 220

Tyr Met Glu Asp Thr Pro
225                 230


<210> SEQ ID NO 58
<211> LENGTH: 228
<212> TYPE: PRT
<213> ORGANISM: Xenopus sp.

<400> SEQUENCE: 58

Trp Glu Lys Val Phe Glu Met Ser Gln Asp Lys Asn Leu Tyr His Asn
1               5                   10                  15

Leu Cys Thr Ser Leu Phe Pro Thr Ile His Gly Asn Asp Glu Ile Lys
            20                  25                  30

Arg Gly Val Leu Leu Met Leu Phe Gly Gly Val Pro Lys Thr Thr Met
        35                  40                  45

Glu Gly Thr Ser Leu Arg Gly Asp Ile Asn Val Cys Ile Val Gly Asp
    50                  55                  60

Pro Ser Thr Ser Lys Ser Gln Phe Leu Lys His Val Glu Glu Phe Ser
65                  70                  75                  80

Pro Arg Ala Val Tyr Thr Ser Gly Lys Ala Ser Ser Ala Ala Gly Leu
                85                  90                  95

Thr Ala Ala Val Val Lys Asp Glu Glu Ser His Glu Phe Val Ile Glu
            100                 105                 110
```

```
Ala Gly Ala Leu Met Leu Ala Asp Asn Gly Val Cys Cys Ile Asp Glu
        115                 120                 125

Phe Asp Lys Met Asp Leu Lys Asp Gln Val Ala Ile His Glu Ala Met
    130                 135                 140

Glu Gln Gln Thr Ile Ser Ile Thr Lys Ala Gly Val Lys Ala Thr Leu
145                 150                 155                 160

Asn Ala Arg Thr Ser Ile Leu Ala Ala Ala Asn Pro Val Gly Gly Arg
                165                 170                 175

Tyr Glu Arg Ser Lys Ser Leu Lys His Asn Val Asn Leu Ser Ala Pro
            180                 185                 190

Ile Met Ser Arg Phe Asp Leu Phe Phe Ile Leu Val Asp Glu Cys Asn
        195                 200                 205

Glu Val Thr Asp Tyr Ala Ile Ala Arg Arg Ile Val Asp Leu His Ala
    210                 215                 220

Arg Asn Glu Glu
225


<210> SEQ ID NO 59
<211> LENGTH: 239
<212> TYPE: PRT
<213> ORGANISM: Xenopus sp.

<400> SEQUENCE: 59

Leu Tyr Ala Ile Gln Glu Ile Gln Ser Gln Glu Asn Leu Phe Gln Leu
1               5                   10                  15

Ile Val Asn Ser Leu Cys Pro Thr Ile Tyr Gly His Glu Leu Val Lys
            20                  25                  30

Ala Gly Leu Ser Leu Ala Leu Phe Gly Gly Cys Gln Lys Tyr Ala Asp
        35                  40                  45

Asp Lys Asn Arg Ile Pro Ile Arg Gly Asp Pro His Ile Leu Val Val
    50                  55                  60

Gly Asp Pro Gly Leu Gly Lys Ser Gln Met Leu Gln Ala Val Cys Asn
65                  70                  75                  80

Val Ala Pro Arg Gly Val Tyr Val Cys Gly Asn Thr Thr Thr Thr Ser
                85                  90                  95

Gly Leu Thr Val Thr Leu Ser Arg Asp Thr Thr Thr Gly Asp Phe Gly
            100                 105                 110

Leu Glu Ala Gly Ala Leu Val Leu Gly Asp Gln Gly Ile Cys Gly Ile
        115                 120                 125

Asp Glu Phe Asp Lys Met Gly Asn Gln His Gln Ala Leu Leu Glu Ala
    130                 135                 140

Met Glu Gln Gln Ser Ile Ser Leu Ala Lys Ala Gly Ile Val Cys Ser
145                 150                 155                 160

Leu Pro Ala Arg Thr Ser Ile Ile Ala Ala Ala Asn Pro Val Gly Gly
                165                 170                 175

His Tyr Asn Lys Gly Lys Thr Val Ser Glu Asn Leu Lys Met Gly Ser
            180                 185                 190

Ala Leu Leu Ser Arg Phe Asp Leu Val Phe Ile Leu Val Asp Thr Pro
        195                 200                 205

Asn Glu Asp His Asp His Leu Leu Ser Glu His Val Met Ala Met Arg
    210                 215                 220

Ser Gly Ala Lys Glu Ile Gln Ser Val Asp Ile Thr Arg Ile Asn
225                 230                 235
```

```
<210> SEQ ID NO 60
<211> LENGTH: 224
<212> TYPE: PRT
<213> ORGANISM: Xenopus sp.

<400> SEQUENCE: 60

Asp Phe Trp Val Lys Tyr Arg Asn Asn Pro Leu Glu Gly Arg Asn Glu
1               5                   10                  15

Ile Leu Ala Ser Leu Cys Pro Gln Val Phe Gly Met Phe Val Val Lys
            20                  25                  30

Leu Ala Val Ala Met Val Leu Ala Gly Gly Val Gln Arg Ile Asp Ser
        35                  40                  45

Ala Gly Thr Arg Val Arg Gly Glu Ser His Leu Leu Leu Val Gly Asp
    50                  55                  60

Pro Gly Thr Gly Lys Ser Gln Phe Leu Lys Tyr Ala Ala Lys Ile Thr
65                  70                  75                  80

Pro Arg Ser Val Leu Thr Ala Gly Ile Gly Ser Thr Ser Ala Gly Leu
                85                  90                  95

Thr Val Thr Ala Val Lys Asp Ser Gly Glu Trp Asn Leu Glu Ala Gly
            100                 105                 110

Ala Leu Val Leu Ala Asp Gly Gly Leu Cys Cys Ile Asp Glu Phe Asn
        115                 120                 125

Ser Ile Lys Glu His Asp Arg Thr Ser Ile His Glu Ala Met Glu Gln
    130                 135                 140

Gln Thr Ile Ser Val Ala Lys Ala Gly Leu Val Cys Lys Leu Asn Thr
145                 150                 155                 160

Arg Thr Thr Ile Leu Ala Ala Thr Asn Pro Lys Gly Gln Tyr Asp Pro
                165                 170                 175

Asp Glu Ser Ile Ser Val Asn Val Ala Leu Ala Ser Pro Leu Leu Ser
            180                 185                 190

Arg Phe Asp Leu Val Leu Val Leu Leu Asp Thr Lys Asn Glu Asp Trp
        195                 200                 205

Asp Arg Ile Ile Ser Ser Phe Ile Leu Glu Ser Lys Gly Cys Pro Arg
    210                 215                 220


<210> SEQ ID NO 61
<211> LENGTH: 494
<212> TYPE: PRT
<213> ORGANISM: Xenopus sp.

<400> SEQUENCE: 61

Leu Gln Arg Leu Glu Arg Gln Gln Ser Glu Asp Ser Leu Glu Ser Asp
1               5                   10                  15

Leu Gly Glu Ser Ala Thr Asn Leu Val Gly His Lys Val Val His Ser
            20                  25                  30

Glu Cys Val Met Glu Glu Thr Phe Ser Thr Phe Glu Ala Ser Ser Leu
        35                  40                  45

Pro Asp Glu Thr His Leu Gly Val Thr Gly Ser Ala Ala Phe Ile Gln
    50                  55                  60

Thr Pro Lys Lys Thr Ile Ser Asp Met Thr Lys Ser Asp Asp Thr Ile
65                  70                  75                  80

Arg Lys Gly Thr Ile Thr Pro Ala Glu Gln Asn Arg Gly Ile Ser Thr
                85                  90                  95

Asp Ala Glu Ser Ser Leu Lys Gln Gly Asn Ala Gln Pro Leu Ala Gly
            100                 105                 110

Gly His Leu Ser Glu Asn Asn Leu Thr Lys Cys Thr Asp Asn Ser Leu
```

```
        115                 120                 125

Gly Trp Phe Asp Thr Leu Gln Ser Ile Gln Met Ser Pro Ile Thr Lys
    130                 135                 140

Gln Arg Glu Gly Cys Thr Ala Glu Lys Leu Gln Gln Glu Val Leu Pro
145                 150                 155                 160

Val Ser Thr Glu Ser Ser Cys His Pro Ala Asp Lys Lys Val Val Asn
                165                 170                 175

Leu Gly Gly Arg Asn Lys Leu Glu Val Leu Gln Ala Ser Gly Ser Ser
            180                 185                 190

Pro Gly Gly Asn Gly Arg Asp Leu Ser Asn His Thr Val Thr Cys Gly
        195                 200                 205

Ser Ser Pro Glu Arg Asn Lys Arg Asp Leu Ser Asn His Ile Val Thr
    210                 215                 220

Glu His Val Ser Lys Lys Trp Arg Arg Ile Asn Lys Asp Ser Leu Cys
225                 230                 235                 240

Gly Lys Asn Val Pro Ser Phe Gln Pro Gln Ser Glu Asn Thr Asp Ser
                245                 250                 255

Ala Pro Val Cys Ser Ser Val Pro Leu His Ser Thr Pro Asp Val Ala
            260                 265                 270

Gln Arg Arg Lys Arg Ile Ile Ala Gln Val Glu Lys Gln Ser Lys Ala
        275                 280                 285

Glu Val Glu Asp Pro Asp Thr Lys Ala Arg Leu Ala Gln Leu Ala Lys
    290                 295                 300

Phe Ser Phe Lys Arg His Ser Lys Leu Val His Ser Pro Ala Gly Asp
305                 310                 315                 320

Thr Asp Thr Ala Ser Asn Ala Gln Lys His Asp His Pro Val Gln Lys
                325                 330                 335

Ile Thr Leu Ser Glu Lys Leu Asn Asn Leu Gly Arg Thr Val Asn Asn
            340                 345                 350

Val Asp Lys Ser Ser Asn Ser Val Asn Gly Ser Lys Gln Gln Lys His
        355                 360                 365

Val Glu Asn Thr Ser Lys Gln Thr Val Ile Thr Gln Lys Ser Asn Phe
    370                 375                 380

Glu Ser Asn Thr Leu Asn Ala Pro Val His Glu Thr Lys Leu Asn Glu
385                 390                 395                 400

Gly Cys Asp Ser Arg Lys Val Ser Ser Ser Thr Leu Ala Lys Leu Ala
                405                 410                 415

Arg Phe Ser Phe Ser Pro Pro Pro Glu Asn Gln Ala Ala Glu Thr Ser
            420                 425                 430

Lys Glu Thr Leu Ile Leu Pro Arg Ala Val Ala Pro Gly Ser Lys Arg
        435                 440                 445

Lys Cys Phe Glu Leu Asn Pro Ser Thr Asp Lys Thr Thr Met Ser Ser
    450                 455                 460

Lys Ser Leu Phe Ser Thr Thr Asp Leu Asp Asp Glu Glu Leu Asp Val
465                 470                 475                 480

Asp Trp Glu Ala Glu Ile Lys Gly Asn Gln Arg Ile Ala Thr
                485                 490


<210> SEQ ID NO 62
<211> LENGTH: 520
<212> TYPE: PRT
<213> ORGANISM: Gallus gallus

<400> SEQUENCE: 62
```

```
Glu Leu Gln Arg Leu Asp Arg Leu Gln Lys Glu Thr Tyr Cys Gln Leu
1               5                   10                  15

Gln Pro Glu Glu Thr Ser Phe Ser Thr Ile Thr Gly Cys Leu Asn Lys
            20                  25                  30

Asn Thr Phe Glu Ser Lys Gln Lys Ser Gln Ser Glu Pro Ser Asp Gln
        35                  40                  45

Gln Lys Ile Asn Ser Tyr Pro Gln Pro Ser Leu Pro Lys Ser Asn Cys
    50                  55                  60

Glu Gly Asp Lys His Pro Glu Ala Leu Arg Asn Pro Thr Pro Gly Asn
65                  70                  75                  80

Asn Ile Ser Thr Lys Arg Leu Ser Arg Leu Asn Lys Arg Ser Asp Asp
                85                  90                  95

Gly Ser Leu Gly Trp Phe Asp Arg Leu Glu Asp Arg Asn Thr Asp Ala
            100                 105                 110

Glu Glu Thr Phe Trp Lys Thr Ser Pro Leu Pro Lys Thr Ser Pro Asp
        115                 120                 125

Asn Met Ala Leu Lys Thr Met Ser Lys Ser Ser Cys Ser Glu Glu Gly
    130                 135                 140

Asn Ser Ser Val Pro Arg Lys Glu Asp Gly Met Arg Gly Ser Leu Arg
145                 150                 155                 160

Thr Val Thr Leu Cys Ala Pro Leu Glu Gln Asp Lys Val Ser Glu Ile
                165                 170                 175

Ser Ser Lys Arg Thr Glu Glu Arg Lys Cys Phe Ser Ser Glu Ala Asn
            180                 185                 190

Ile Gln Asp Pro Thr Ser Ala Ser Ala Ser Val Gln Glu Ser Val Ile
        195                 200                 205

Thr Gln Arg Val Ser Lys Ser Leu Gln Arg Leu His Thr Glu Lys Ser
    210                 215                 220

His Arg Phe Phe Thr Ser Thr Gln Asn Ser Glu Ala Asn Ala Leu Pro
225                 230                 235                 240

Ser Val Leu Pro Val Ser Gly Leu Leu Asp Leu Ser Ser Asp Thr Asp
                245                 250                 255

Ser Val Val Gly Asp Glu Ser Asn Ser Ala Ser Ala Ala Val Lys His
            260                 265                 270

Ala Val Ile Ser Met Arg Lys Arg Ser Lys Gly Gln Ala Glu Lys Glu
        275                 280                 285

Ala Lys Ala Val Ser Ser His Glu Pro Glu Ile Thr Asp Gly Glu Ser
    290                 295                 300

Pro Pro Ala Ala Lys Leu Ala Lys Phe Ser Phe Arg Pro Arg Thr Lys
305                 310                 315                 320

Leu Asp Asp Ser Ser Glu Lys Lys Asn Ala Glu Phe Pro Leu Phe Pro
                325                 330                 335

Ser Glu Asn Thr Val Lys Pro Gly Glu Gln Pro Gln Gly Glu Gln Leu
            340                 345                 350

Gln Lys Asp Cys Cys Pro Pro Glu Lys Arg Lys Met Thr Leu Thr Cys
        355                 360                 365

Leu Gly Arg Lys Gly Leu Glu Lys Gln Ser Ile Gly Ser Lys Gly Asn
    370                 375                 380

Glu Glu Gln Leu Ser Gln Ala Leu Gly Lys Glu Met Gly Gly Asn Ala
385                 390                 395                 400

Leu Ile His Ser Asp Val Thr Leu Asp Val Val Ser Pro Pro Pro Thr
                405                 410                 415

Glu Lys Arg Arg Glu Gly Glu Glu Lys Leu Gly Gly Pro Ser Thr Val
```

```
            420                 425                 430

Arg Val Cys Ser Ser Thr Leu Glu Asn Leu Ser Lys Phe Cys Phe Ala
        435                 440                 445

Ser Arg Pro Asp Ser Lys Ser Glu Ala Pro Pro Thr Ile Lys Thr Asp
    450                 455                 460

Thr Asn Asn Lys Glu Ser His Ser Pro Leu Leu Lys Val His Val Ser
465                 470                 475                 480

Asn Pro Asn Lys Arg Lys Ser Phe Ala Leu Gly Asn Ala Ser Lys Asp
                485                 490                 495

Ser Val Val Thr Arg Lys Ser Leu Phe Ser Ile Ala Glu Leu Asp Asp
            500                 505                 510

Ala Thr Leu Asp Phe Asp Trp Asp
        515                 520


<210> SEQ ID NO 63
<211> LENGTH: 491
<212> TYPE: PRT
<213> ORGANISM: Mus musculus

<400> SEQUENCE: 63

Leu Leu Gln Glu Glu Leu Arg Arg Leu Glu Arg Leu Gln Asn Glu Ser
1               5                   10                  15

Val His Gln Cys Gln Ser His Ser Leu Glu Glu Glu Val Ala Pro Gly
            20                  25                  30

Ser Cys Arg Asn Asp Pro Arg Asp Lys Pro Arg Leu Arg Thr Ser Thr
        35                  40                  45

Gln Gln Glu Gln Ser Cys Ser Trp Ser Ser Thr Glu Arg Ser Gly Ala
    50                  55                  60

Asp Ser Pro Pro Gly Pro Gly Leu Asn Arg Pro Thr Ser Cys Asn Asn
65                  70                  75                  80

Ser Ala Glu Asn Arg Asp Gly Arg Gly Asp Gly Leu Asp Trp Leu Asp
                85                  90                  95

Pro Thr Ser Ser Pro Glu Ile Ala Pro Glu Ser Thr Ile Val Ser Pro
            100                 105                 110

Asn Val Lys Thr Thr Glu Lys Asn Val Asn Leu Lys Ile Ser Asn Asn
        115                 120                 125

Lys Ser Gln Gly Lys Glu Lys His Gly Pro Gln Gln Arg Ser Lys Leu
    130                 135                 140

Leu Glu Ala Gly His Leu Pro Ser Ser Gly Ala Met Asn Ala Pro Leu
145                 150                 155                 160

Arg Ser His Gly Val Lys Arg Thr Lys Ala Ser Gln Ala Val Val Val
                165                 170                 175

Ser Glu Ala Gly Arg Gly Asp Glu Glu Asp Ser Val Pro Arg Arg Leu
            180                 185                 190

Pro Lys Leu Leu Lys Glu Gly Ser Gln Asn Val Cys Arg Ser Thr Thr
        195                 200                 205

Arg Val Arg Pro Leu Pro Pro Thr Val Pro Leu Ser Leu Ser Ile Pro
    210                 215                 220

Ser Pro Gly Ser Gly Lys Arg Ser Gly Thr Pro Lys Arg Lys Arg Arg
225                 230                 235                 240

Lys Ser Ala Gln Val Glu Glu Pro Glu Pro Glu Gly Met Glu Thr Pro
                245                 250                 255

Thr Val Lys Leu Ala Lys Phe Thr Phe Lys Gln Lys Thr Lys Leu Thr
            260                 265                 270
```

```
His Ser Pro Glu Gly Gln Gly Pro Ile Pro Pro Ser Ala Ser Glu Ile
        275                 280                 285

Ala Val Asp Ser Ser Lys Ile Pro Gln Gln Arg Thr Arg Arg Glu Ala
    290                 295                 300

Ala Val Pro Val Val Ala Pro Gly Lys Ser Thr Ser Thr Ser Gly Asp
305                 310                 315                 320

Arg Cys Ser Asp Gln Leu His Gly Lys Thr Lys Glu Leu Ser Arg Gln
                325                 330                 335

Pro Pro Asp Ser Asn Pro Pro Arg Glu Glu Arg Glu Gln Gly Pro Lys
            340                 345                 350

Arg Arg Val Ile Gln Pro Lys Pro Glu Leu Gly Asn Gln Ala Gly His
        355                 360                 365

Ser His Leu Ala Cys Glu Lys Asp Arg Lys Glu Gly Val Ser Cys Gly
    370                 375                 380

Asn Lys Ser Ser Lys Val His Ala Gly Thr Ile Ala Arg Leu Ala Ser
385                 390                 395                 400

Phe Ser Phe Thr Ser Pro Ser Glu Ser Lys Ser Glu Ser Leu Pro Pro
                405                 410                 415

Glu Arg Lys Asp Ser Arg Asp Ser Arg Asp Ser Arg Asp Ser Arg Asp
            420                 425                 430

Arg Cys His Ser Pro Pro Ala Thr Thr Ala Pro Val Leu Gly Gln Gln
        435                 440                 445

Arg Gln Thr Phe Gln Leu Gln Gln Pro Thr Glu Arg Ala Asn Leu Ser
    450                 455                 460

Thr Leu Ser Leu Phe Thr Leu Ser Glu Leu Asp Asp Glu Ala Leu Asp
465                 470                 475                 480

Phe Asp Trp Glu Glu Glu Met Arg Lys Lys Pro
                485                 490


<210> SEQ ID NO 64
<211> LENGTH: 494
<212> TYPE: PRT
<213> ORGANISM: Homo sapiens

<400> SEQUENCE: 64

Arg Arg Leu Glu Arg Leu Gln Asn Gln Ser Val His Gln Ser Gln Pro
1               5                   10                  15

Arg Val Leu Glu Val Glu Thr Thr Pro Gly Ser Leu Arg Asn Gly Pro
            20                  25                  30

Gly Glu Glu Ser Asn Phe Arg Thr Ser Ser Gln Gln Glu Ile Asn Tyr
        35                  40                  45

Ser Thr His Ile Phe Ser Pro Gly Gly Ser Pro Glu Gly Ser Pro Val
    50                  55                  60

Leu Asp Pro Pro Pro His Leu Glu Pro Asn Arg Ser Thr Ser Arg Lys
65                  70                  75                  80

His Ser Ala Gln His Lys Asn Asn Arg Asp Asp Ser Leu Asp Trp Phe
                85                  90                  95

Asp Phe Met Ala Thr His Gln Ser Glu Pro Lys Asn Thr Val Val Val
            100                 105                 110

Ser Pro His Pro Lys Thr Ser Gly Glu Asn Met Ala Ser Lys Ile Ser
        115                 120                 125

Asn Ser Thr Ser Gln Gly Lys Glu Lys Ser Glu Pro Gly Gln Arg Ser
    130                 135                 140

Lys Val Asp Ile Gly Leu Leu Pro Ser Pro Gly Glu Thr Gly Val Pro
145                 150                 155                 160
```

```
Trp Arg Ala Asp Asn Val Glu Ser Asn Lys Lys Lys Arg Leu Ala Leu
                165                 170                 175

Asp Ser Glu Ala Ala Val Ser Ala Asp Lys Pro Asp Ser Val Leu Thr
            180                 185                 190

His His Val Pro Arg Asn Leu Gln Lys Leu Cys Lys Glu Arg Ala Gln
        195                 200                 205

Lys Leu Cys Arg Asn Ser Thr Arg Val Pro Ala Gln Cys Thr Val Pro
    210                 215                 220

Ser His Pro Gln Ser Thr Pro Val His Ser Pro Asp Arg Arg Leu Asp
225                 230                 235                 240

Ser Pro Lys Arg Lys Arg Pro Lys Ser Leu Ala Gln Val Glu Glu Pro
                245                 250                 255

Ala Ile Glu Asn Val Lys Pro Pro Gly Ser Pro Val Ala Lys Leu Ala
            260                 265                 270

Lys Phe Thr Phe Lys Gln Lys Ser Lys Leu Ile His Ser Phe Glu Asp
        275                 280                 285

His Ser His Val Ser Pro Gly Ala Thr Lys Ile Ala Val His Ser Pro
    290                 295                 300

Lys Ile Ser Gln Arg Arg Thr Arg Arg Asp Ala Ala Leu Pro Val Lys
305                 310                 315                 320

Arg Pro Gly Lys Leu Thr Ser Thr Pro Gly Asn Gln Ile Ser Ser Gln
                325                 330                 335

Pro Gln Gly Glu Thr Lys Glu Val Ser Gln Gln Pro Pro Glu Lys His
            340                 345                 350

Gly Pro Arg Glu Lys Val Met Cys Ala Pro Glu Lys Arg Ile Ile Gln
        355                 360                 365

Pro Glu Leu Glu Leu Gly Asn Glu Thr Gly Cys Ala His Leu Thr Cys
    370                 375                 380

Glu Gly Asp Lys Lys Glu Glu Val Ser Gly Ser Asn Lys Ser Gly Lys
385                 390                 395                 400

Val His Ala Cys Thr Leu Ala Arg Leu Ala Asn Phe Cys Phe Thr Pro
                405                 410                 415

Pro Ser Glu Ser Lys Ser Lys Ser Pro Pro Pro Glu Arg Lys Asn Arg
            420                 425                 430

Gly Glu Arg Gly Pro Ser Ser Pro Pro Thr Thr Thr Ala Pro Met Arg
        435                 440                 445

Val Ser Lys Arg Lys Ser Phe Gln Leu Arg Gly Ser Thr Glu Lys Leu
    450                 455                 460

Ile Val Ser Lys Glu Ser Leu Phe Thr Leu Pro Glu Leu Gly Asp Glu
465                 470                 475                 480

Ala Phe Asp Cys Asp Trp Asp Glu Glu Met Arg Lys Lys Ser
                485                 490
```

<210> SEQ ID NO 65
<211> LENGTH: 20
<212> TYPE: PRT
<213> ORGANISM: Homo sapiens

<400> SEQUENCE: 65

```
Glu Thr Lys Glu Val Ser Gln Gln Pro Pro Glu Lys His Gly Pro Arg
1               5                   10                  15

Glu Lys Val Met
            20
```

<210> SEQ ID NO 66
<211> LENGTH: 20
<212> TYPE: PRT
<213> ORGANISM: Homo sapiens

<400> SEQUENCE: 66

Pro Trp Arg Ala Asp Asn Val Glu Ser Asn Lys Lys Lys Arg Leu Ala
1               5                   10                  15

Leu Asp Ser Glu
            20

<210> SEQ ID NO 67
<211> LENGTH: 18
<212> TYPE: DNA
<213> ORGANISM: Artificial Sequence
<220> FEATURE:
<223> OTHER INFORMATION: Synthetic primer

<400> SEQUENCE: 67
tacaggaaca cgggtcag 18

<210> SEQ ID NO 68
<211> LENGTH: 18
<212> TYPE: DNA
<213> ORGANISM: Artificial Sequence
<220> FEATURE:
<223> OTHER INFORMATION: Sythetic primer

<400> SEQUENCE: 68
gaaacatcag gcgagcat 18

<210> SEQ ID NO 69
<211> LENGTH: 18
<212> TYPE: DNA
<213> ORGANISM: Artificial Sequence
<220> FEATURE:
<223> OTHER INFORMATION: Synthetic primer

<400> SEQUENCE: 69
tacaggaaca cgggtcag 18

<210> SEQ ID NO 70
<211> LENGTH: 21
<212> TYPE: DNA
<213> ORGANISM: Artificial Sequence
<220> FEATURE:
<223> OTHER INFORMATION: Synthetic primer

<400> SEQUENCE: 70
tgccatgaaa tcaaaccaat c 21

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
tttgatttca tggcaactca t 21

<210> SEQ ID NO 72
<211> LENGTH: 21
<212> TYPE: DNA
<213> ORGANISM: Artificial Sequence
<220> FEATURE:

<223> OTHER INFORMATION: Synthetic primer

<400> SEQUENCE: 72
cgcattggag ctgtggttgt a 21

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
ttgatagtgc actgcgaagg t 21

<210> SEQ ID NO 74
<211> LENGTH: 19
<212> TYPE: DNA
<213> ORGANISM: Artificial Sequence
<220> FEATURE:
<223> OTHER INFORMATION: Synthetic primer

<400> SEQUENCE: 74
tgcattacaa tcccgtaaa 19

<210> SEQ ID NO 75
<211> LENGTH: 33
<212> TYPE: DNA
<213> ORGANISM: Artificial Sequence
<220> FEATURE:
<223> OTHER INFORMATION: Synthetic primer

<400> SEQUENCE: 75
gggggggtcg accagccatt acctagattc aag 33

<210> SEQ ID NO 76
<211> LENGTH: 32
<212> TYPE: DNA
<213> ORGANISM: Artificial Sequence
<220> FEATURE:
<223> OTHER INFORMATION: Synthetic primer

<400> SEQUENCE: 76
ggggggctcg agcagaaagc ttttcccaac ta 32